(12) United States Patent  
Williams et al.

(10) Patent No.: US 7,899,554 B2  
(45) Date of Patent: *Mar. 1, 2011

(54) INTRAVASCULAR SYSTEM AND METHOD

(75) Inventors: Michael S. Williams, Santa Rosa, CA (US); Terrance Ransbury, Chapel Hill, NC (US); Richard A. Glenn, Santa Rosa, CA (US); Daniel W. Fifer, Windsor, CA (US); Kevin Holbrook, Chapel Hill, NC (US)

(73) Assignee: Synecor LLC, Durham, NC (US)

( * ) Notice: Subject to any disclaimer, the term of this patent is extended or adjusted under 35 U.S.C. 154(b) by 614 days.

This patent is subject to a terminal disclaimer.

(21) Appl. No.: 11/980,006

(22) Filed: Oct. 30, 2007

(65) Prior Publication Data

US 2008/0077219 A1 Mar. 27, 2008

Related U.S. Application Data

(60) Division of application No. 10/862,113, filed on Jun. 4, 2004, now Pat. No. 7,529,589, which is a continuation-in-part of application No. 10/454,223, filed on Jun. 4, 2003, now Pat. No. 7,082,336.

(60) Provisional application No. 60/515,746, filed on Oct. 30, 2003, provisional application No. 60/516,026, filed on Oct. 31, 2003, provisional application No. 60/525,332, filed on Nov. 26, 2003, provisional application No. 60/525,336, filed on Nov. 26, 2003, provisional application No. 60/543,260, filed on Feb. 10, 2004.

(51) Int. Cl.  
*A61N 1/02* (2006.01)

(52) U.S. Cl. ............................................ 607/126; 607/2

(58) Field of Classification Search .................. 607/2, 5, 607/9, 14, 115, 116, 126  
See application file for complete search history.

(56) References Cited

U.S. PATENT DOCUMENTS

| | | | |
|---|---|---|---|
| 3,211,154 A | 10/1965 | Becker et al. | 128/421 |
| 3,236,239 A | 2/1966 | Berkovits | 128/419 |
| 3,258,013 A | 6/1966 | Druz | 128/419 |
| 3,389,704 A | 6/1968 | Buchowski et al. | 128/419 |
| 3,835,864 A | 9/1974 | Rasor et al. | |
| 3,865,101 A | 2/1975 | Saper et al. | 128/2.06 R |

(Continued)

FOREIGN PATENT DOCUMENTS

EP 0 030 953 B1 7/1981

(Continued)

OTHER PUBLICATIONS

U.S. Appl. No. 10/453,971, Ransbury et al., Device and Method for Retaining a Medical Device within a Vessel; Filed: Jun. 4, 2003.*

(Continued)

*Primary Examiner* — Carl H Layno  
*Assistant Examiner* — Brian T Gedeon

(57) ABSTRACT

The present application describes an intravascular implantable pacing and/or defibrillation system. The described system includes a pulse generator that is implantable within a blood vessel and proportioned to blood flow through the blood vessel, and at least one electrode attachable to the pulse generator. During implantation, the pulse generator is introduced into a patient's vasculature, advanced to a desired vessel and anchored in place within the vessel. The electrode or electrodes are placed within the heart or surrounding vessels as needed to deliver electrical pulses to the appropriate location.

16 Claims, 42 Drawing Sheets

U.S. PATENT DOCUMENTS

| | | | |
|---|---|---|---|
| 3,906,960 A | 9/1975 | Lehr | 128/419 PG |
| 3,959,706 A | 5/1976 | Mabuchi et al. | 320/103 |
| 4,025,860 A | 5/1977 | Shibata et al. | 320/3 |
| 4,030,509 A | 6/1977 | Heilman et al. | 128/419 D |
| 4,041,956 A | 8/1977 | Purdy et al. | 607/36 |
| 4,096,856 A | 6/1978 | Smith et al. | 128/4.19 D |
| 4,096,866 A | 6/1978 | Fischell | 607/34 |
| 4,168,711 A | 9/1979 | Cannon, III et al. | 607/5 |
| RE30,366 E | 8/1980 | Rasor et al. | |
| 4,323,075 A | 4/1982 | Langer | 607/5 |
| 4,326,532 A | 4/1982 | Hammar | |
| 4,332,259 A | 6/1982 | McCorkle, Jr. | 607/123 |
| 4,414,986 A | 11/1983 | Dickhudt et al. | 607/117 |
| 4,485,813 A | 12/1984 | Anderson et al. | |
| 4,510,551 A | 4/1985 | Brainard, II | |
| 4,530,550 A | 7/1985 | Kondo | 315/241 P |
| 4,559,951 A | 12/1985 | Dahl et al. | 600/374 |
| 4,628,944 A | 12/1986 | MacGregor et al. | |
| 4,635,639 A | 1/1987 | Hakala et al. | 607/4 |
| 4,637,397 A | 1/1987 | Jones et al. | 607/5 |
| 4,662,377 A | 5/1987 | Heilman et al. | 607/4 |
| 4,687,482 A | 8/1987 | Hanson | |
| 4,708,145 A | 11/1987 | Tacker, Jr. et al. | 607/5 |
| 4,722,353 A | 2/1988 | Sluetz | 607/128 |
| 4,727,877 A | 3/1988 | Kallok | 607/5 |
| 4,736,150 A | 4/1988 | Wagner | 320/139 |
| 4,825,871 A | 5/1989 | Cansell | 607/2 |
| 4,827,936 A | 5/1989 | Pless et al. | 607/4 |
| 4,850,357 A | 7/1989 | Bach, Jr. | 607/7 |
| 4,892,102 A | 1/1990 | Astrinsky | 600/374 |
| 4,900,303 A | 2/1990 | Lemelson | |
| 4,931,947 A | 6/1990 | Werth et al. | 700/297 |
| 4,953,551 A | 9/1990 | Mehra et al. | 607/5 |
| 4,969,463 A | 11/1990 | Dahl et al. | 607/5 |
| 4,991,603 A | 2/1991 | Cohen et al. | 607/125 |
| 4,996,984 A | 3/1991 | Sweeney | 607/5 |
| 4,998,531 A | 3/1991 | Bocchi et al. | 607/5 |
| 4,998,975 A | 3/1991 | Cohen et al. | 607/5 |
| 5,010,894 A | 4/1991 | Edhag | 607/128 |
| 5,014,696 A | 5/1991 | Mehra | 607/5 |
| 5,044,375 A | 9/1991 | Bach, Jr. et al. | 607/122 |
| 5,099,838 A | 3/1992 | Bardy | 607/2 |
| 5,105,810 A | 4/1992 | Collins et al. | 607/9 |
| 5,107,834 A | 4/1992 | Ideker et al. | 607/5 |
| 5,129,392 A | 7/1992 | Bardy et al. | 607/2 |
| 5,131,388 A | 7/1992 | Pless et al. | 607/5 |
| 5,133,353 A | 7/1992 | Hauser | 607/4 |
| 5,144,946 A | 9/1992 | Weinberg et al. | 607/2 |
| 5,163,427 A | 11/1992 | Keimel | 607/5 |
| 5,170,784 A | 12/1992 | Ramon et al. | 607/9 |
| 5,170,802 A | 12/1992 | Mehra | 607/126 |
| 5,174,288 A | 12/1992 | Bardy et al. | 607/2 |
| 5,193,540 A | 3/1993 | Schulman et al. | |
| 5,199,429 A | 4/1993 | Kroll et al. | 607/5 |
| 5,221,261 A | 6/1993 | Termin et al. | 604/104 |
| 5,231,996 A | 8/1993 | Bardy et al. | 607/126 |
| 5,235,977 A | 8/1993 | Hirschberg et al. | 607/5 |
| 5,235,978 A | 8/1993 | Hirschberg et al. | 607/5 |
| 5,235,979 A | 8/1993 | Adams | 607/5 |
| 5,241,960 A | 9/1993 | Anderson et al. | 607/5 |
| 5,261,400 A | 11/1993 | Bardy | 607/5 |
| 5,282,785 A | 2/1994 | Shapland et al. | |
| 5,292,338 A | 3/1994 | Bardy | 607/5 |
| 5,306,291 A | 4/1994 | Kroll et al. | 607/5 |
| 5,314,430 A | 5/1994 | Bardy | 607/5 |
| 5,324,309 A | 6/1994 | Kallok | 607/5 |
| 5,334,221 A | 8/1994 | Bardy | 607/14 |
| 5,342,399 A | 8/1994 | Kroll | 607/5 |
| 5,356,425 A | 10/1994 | Bardy et al. | 607/14 |
| 5,358,514 A | 10/1994 | Schulman et al. | |
| 5,368,588 A | 11/1994 | Bettinger | |
| 5,372,585 A | 12/1994 | Tiefenbrun et al. | |
| 5,383,907 A | 1/1995 | Kroll | 607/5 |
| 5,407,444 A | 4/1995 | Kroll | 607/5 |
| 5,411,546 A | 5/1995 | Bowald et al. | 607/126 |
| 5,423,865 A | 6/1995 | Bowald et al. | 607/5 |
| 5,423,885 A | 6/1995 | Williams | |
| 5,431,686 A | 7/1995 | Kroll et al. | 607/7 |
| 5,468,254 A | 11/1995 | Hahn et al. | 607/5 |
| 5,483,165 A | 1/1996 | Cameron et al. | 324/427 |
| 5,487,760 A | 1/1996 | Villafana | |
| 5,509,411 A | 4/1996 | Littmann et al. | 600/381 |
| 5,531,779 A | 7/1996 | Dahl et al. | |
| 5,534,015 A | 7/1996 | Kroll et al. | 607/7 |
| 5,545,205 A | 8/1996 | Schulte et al. | 607/123 |
| 5,551,954 A | 9/1996 | Buscemi et al. | |
| 5,591,211 A | 1/1997 | Meltzer | 607/5 |
| 5,591,213 A | 1/1997 | Morgan | 607/5 |
| 5,593,427 A | 1/1997 | Gliner et al. | 607/7 |
| 5,593,434 A | 1/1997 | Williams | |
| 5,601,612 A | 2/1997 | Gliner et al. | 607/7 |
| 5,607,454 A | 3/1997 | Cameron et al. | 607/5 |
| 5,613,935 A | 3/1997 | Jarvik | |
| 5,617,853 A | 4/1997 | Morgan | 600/386 |
| 5,620,470 A | 4/1997 | Gliner et al. | 607/7 |
| 5,645,586 A | 7/1997 | Meltzer | |
| 5,699,796 A | 12/1997 | Littmann et al. | 600/374 |
| 5,704,910 A | 1/1998 | Humes | |
| 5,716,391 A | 2/1998 | Grandjean | |
| 5,735,879 A | 4/1998 | Gliner et al. | 607/7 |
| 5,735,887 A | 4/1998 | Barreras, Sr. et al. | |
| 5,735,897 A | 4/1998 | Buirge | |
| 5,749,904 A | 5/1998 | Gliner et al. | 607/7 |
| 5,749,905 A | 5/1998 | Gliner et al. | 607/7 |
| 5,769,077 A | 6/1998 | Lindegren | |
| 5,776,166 A | 7/1998 | Gliner et al. | 607/7 |
| 5,800,460 A | 9/1998 | Powers et al. | 607/5 |
| 5,803,927 A | 9/1998 | Cameron et al. | 607/5 |
| 5,807,399 A | 9/1998 | Laske et al. | |
| 5,814,089 A | 9/1998 | Stokes et al. | 607/32 |
| 5,827,326 A | 10/1998 | Kroll et al. | 607/5 |
| 5,833,603 A | 11/1998 | Kovacs et al. | |
| 5,836,978 A | 11/1998 | Gliner et al. | 607/7 |
| 5,843,132 A | 12/1998 | Ilvento | 607/10 |
| 5,849,033 A | 12/1998 | Mehmanesh et al. | |
| 5,868,792 A | 2/1999 | Ochs et al. | 607/5 |
| 5,879,374 A | 3/1999 | Powers et al. | 607/5 |
| 5,891,046 A | 4/1999 | Cyrus et al. | 600/510 |
| 5,891,049 A | 4/1999 | Cyrus et al. | 600/523 |
| 5,904,707 A | 5/1999 | Ochs et al. | 607/6 |
| 5,908,447 A | 6/1999 | Schroeppel et al. | |
| 5,911,704 A | 6/1999 | Humes | |
| 5,919,210 A | 7/1999 | Lurie et al. | 607/3 |
| 5,951,485 A | 9/1999 | Cyrus et al. | 600/523 |
| 5,954,761 A | 9/1999 | Machek et al. | 67/126 |
| 5,957,842 A | 9/1999 | Littmann et al. | 600/381 |
| 5,957,956 A | 9/1999 | Kroll et al. | 607/5 |
| 6,016,059 A | 1/2000 | Morgan | 324/556 |
| 6,045,568 A | 4/2000 | Igaki et al. | |
| 6,047,212 A | 4/2000 | Gliner et al. | 607/7 |
| 6,053,873 A | 4/2000 | Govari et al. | |
| 6,088,610 A | 7/2000 | Littmann et al. | 600/381 |
| 6,119,039 A | 9/2000 | Leyde | 607/5 |
| 6,141,576 A | 10/2000 | Littmann et al. | 600/381 |
| 6,141,588 A | 10/2000 | Cox et al. | 607/9 |
| 6,161,029 A | 12/2000 | Spreigl et al. | 600/381 |
| 6,214,032 B1 | 4/2001 | Loeb et al. | |
| 6,219,581 B1 | 4/2001 | Schaldach et al. | 607/122 |
| 6,230,061 B1 | 5/2001 | Hartung | 607/122 |
| 6,231,516 B1 | 5/2001 | Keilman et al. | |
| 6,256,534 B1 | 7/2001 | Dahl | 607/5 |
| 6,256,541 B1 | 7/2001 | Heil et al. | |
| 6,304,786 B1 | 10/2001 | Heil, Jr. et al. | |
| 6,330,481 B1 | 12/2001 | Van Wijk et al. | |
| 6,383,171 B1 | 5/2002 | Gifford et al. | |
| 6,419,692 B1 | 7/2002 | Yang et al. | 623/1.15 |
| 6,436,068 B1 | 8/2002 | Bardy | 604/57 |
| 6,442,413 B1 | 8/2002 | Silver | 600/345 |
| 6,445,953 B1 | 9/2002 | Bulkes et al. | |
| 6,509,104 B2 | 1/2003 | Huang et al. | |
| 6,516,231 B1 | 2/2003 | Flammang | 607/122 |
| 6,522,926 B1 | 2/2003 | Kieval et al. | |
| 6,561,975 B1 | 5/2003 | Pool et al. | 600/300 |
| 6,564,807 B1 | 5/2003 | Schulman et al. | |
| 6,572,605 B1 | 6/2003 | Humes | |
| 6,584,362 B1 | 6/2003 | Scheiner et al. | 607/122 |
| 6,671,547 B2 | 12/2003 | Lyster et al. | 607/6 |

| | | |
|---|---|---|
| 6,716,208 B2 | 4/2004 | Humes |
| 6,723,121 B1 | 4/2004 | Zhong |
| 6,726,714 B2 | 4/2004 | DiCaprio et al. |
| 6,733,485 B1 | 5/2004 | Whitehurst et al. ........ 604/500 |
| 6,735,474 B1 | 5/2004 | Loeb et al. ................. 607/41 |
| 6,735,475 B1 | 5/2004 | Whitehurst et al. ......... 607/46 |
| 6,754,528 B2 | 6/2004 | Bardy et al. ................ 607/5 |
| 6,760,622 B2 | 7/2004 | Helland et al. ............. 607/9 |
| 6,776,784 B2 | 8/2004 | Ginn ...................... 606/151 |
| 6,778,860 B2 | 8/2004 | Ostroff et al. ............. 607/7 |
| 6,783,499 B2 | 8/2004 | Schwartz |
| 6,783,543 B2 | 8/2004 | Jang |
| 6,788,974 B2 | 9/2004 | Bardy et al. ............... 607/36 |
| 6,829,504 B1 | 12/2004 | Chen et al. |
| 6,834,204 B2 | 12/2004 | Ostroff et al. ............. 607/2 |
| 6,845,267 B2 | 1/2005 | Harrison et al. |
| 6,866,044 B2 | 3/2005 | Bardy et al. ............. 128/898 |
| 6,885,895 B1 | 4/2005 | Whitehurst et al. ......... 607/39 |
| 6,907,285 B2 | 6/2005 | Denker et al. ............. 607/5 |
| 6,932,930 B2 | 8/2005 | DeSimone et al. |
| 6,933,822 B2 | 8/2005 | Haugs et al. |
| 6,941,169 B2 | 9/2005 | Pappu |
| 7,003,350 B2 | 2/2006 | Denker et al. |
| 7,006,858 B2 | 2/2006 | Silver et al. |
| 7,054,692 B1 | 5/2006 | Whitehurst et al. |
| 7,072,171 B1 | 7/2006 | Muffoletto et al. |
| 7,082,336 B2 * | 7/2006 | Ransbury et al. .......... 607/126 |
| 7,097,665 B2 | 8/2006 | Stack et al. |
| 7,114,502 B2 | 10/2006 | Schulman et al. |
| 7,236,821 B2 | 6/2007 | Cates et al. |
| 7,239,921 B2 | 7/2007 | Canfield et al. |
| 7,363,082 B2 | 4/2008 | Ransbury et al. |
| 7,529,589 B2 * | 5/2009 | Williams et al. ........... 607/119 |
| 7,617,007 B2 * | 11/2009 | Williams et al. ........... 607/126 |
| 7,747,335 B2 * | 6/2010 | Williams .................. 607/126 |
| 2001/0021840 A1 | 9/2001 | Suresh et al. |
| 2001/0041930 A1 | 11/2001 | Globerman et al. |
| 2002/0026228 A1 | 2/2002 | Schauerte ................. 607/122 |
| 2002/0042630 A1 | 4/2002 | Bardy et al. ............... 607/5 |
| 2002/0042634 A1 | 4/2002 | Bardy et al. ............... 607/36 |
| 2002/0052636 A1 | 5/2002 | Bardy et al. ............... 607/129 |
| 2002/0072773 A1 | 6/2002 | Bardy et al. ............... 607/5 |
| 2002/0090388 A1 | 7/2002 | Humes et al. |
| 2002/0090389 A1 | 7/2002 | Humes et al. .............. 424/422 |
| 2002/0103510 A1 | 8/2002 | Bardy et al. ............... 607/5 |
| 2002/0107545 A1 | 8/2002 | Rissmann et al. ........... 607/5 |
| 2002/0107546 A1 | 8/2002 | Ostroff et al. ............. 607/4 |
| 2002/0107547 A1 | 8/2002 | Erlinger et al. ............ 607/5 |
| 2002/0107548 A1 | 8/2002 | Bardy et al. ............... 607/5 |
| 2002/0107549 A1 | 8/2002 | Bardy et al. ............... 607/5 |
| 2002/0107559 A1 | 8/2002 | Sanders et al. ............. 607/129 |
| 2002/0111585 A1 | 8/2002 | Lafontaine |
| 2002/0120299 A1 | 8/2002 | Ostroff et al. ............. 607/5 |
| 2002/0128546 A1 | 9/2002 | Silver |
| 2002/0133224 A1 | 9/2002 | Bajgar et al. .............. 623/1.39 |
| 2002/0143379 A1 | 10/2002 | Morgan et al. |
| 2002/0147486 A1 | 10/2002 | Soukup et al. |
| 2002/0183791 A1 | 12/2002 | Denker et al. ............. 607/5 |
| 2002/0188252 A1 | 12/2002 | Bardy et al. ............... 604/93.01 |
| 2003/0023177 A1 | 1/2003 | Bardy et al. ............... 600/510 |
| 2003/0032892 A1 | 2/2003 | Erlach et al. .............. 600/547 |
| 2003/0032998 A1 | 2/2003 | Altman |
| 2003/0036778 A1 | 2/2003 | Ostroff et al. ............. 607/9 |
| 2003/0045904 A1 | 3/2003 | Bardy et al. ............... 607/4 |
| 2003/0060863 A1 | 3/2003 | Dobak, III |
| 2003/0088278 A1 | 5/2003 | Bardy et al. ............... 607/5 |
| 2003/0097051 A1 | 5/2003 | Kolberg et al. ............. 600/381 |
| 2003/0114905 A1 | 6/2003 | Kuzma |
| 2003/0158584 A1 | 8/2003 | Cates et al. ............... 607/2 |
| 2004/0073190 A1 | 4/2004 | Deem et al. |
| 2004/0116992 A1 | 6/2004 | Wardle et al. |
| 2004/0147993 A1 | 7/2004 | Westlund et al. |
| 2004/0172090 A1 | 9/2004 | Janzig et al. |
| 2004/0207503 A1 | 10/2004 | Flanders et al. |
| 2004/0249417 A1 | 12/2004 | Ransbury et al. |
| 2004/0249431 A1 | 12/2004 | Ransbury et al. |
| 2005/0004639 A1 | 1/2005 | Erickson |
| 2005/0019370 A1 | 1/2005 | Humes |
| 2005/0043765 A1 | 2/2005 | Williams et al. |
| 2005/0043789 A1 | 2/2005 | Widenhouse et al. |
| 2005/0080472 A1 | 4/2005 | Atkinson et al. .............. 607/126 |
| 2005/0119718 A1 | 6/2005 | Coe et al. |
| 2005/0147647 A1 | 7/2005 | Glauser et al. |
| 2005/0228471 A1 | 10/2005 | Williams et al. |
| 2005/0234431 A1 | 10/2005 | Williams et al. |
| 2006/0095078 A1 | 5/2006 | Tronnes |
| 2006/0129050 A1 | 6/2006 | Martinson et al. |
| 2006/0224225 A1 | 10/2006 | Ransbury et al. |
| 2006/0241732 A1 | 10/2006 | Denker et al. |
| 2008/0077219 A1 | 3/2008 | Williams et al. |
| 2008/0154327 A1 | 6/2008 | Ransbury et al. |

FOREIGN PATENT DOCUMENTS

| | | |
|---|---|---|
| EP | 0 057 448 B1 | 8/1982 |
| EP | 0 281 219 B1 | 9/1988 |
| EP | 0 373 953 A2 | 6/1990 |
| EP | 0 373 953 A3 | 6/1990 |
| EP | 0 424 379 B1 | 5/1991 |
| EP | 0 426 089 A2 | 5/1991 |
| EP | 0 426 089 A3 | 5/1991 |
| EP | 0 453 761 A1 | 10/1991 |
| EP | 0 526 671 A1 | 2/1993 |
| EP | 0 526 671 B1 | 2/1993 |
| EP | 0 559 932 A1 | 9/1993 |
| EP | 0 559 933 A1 | 9/1993 |
| EP | 0 570 712 A1 | 11/1993 |
| EP | 0 570 712 B1 | 11/1993 |
| EP | 0 578 748 B1 | 1/1994 |
| EP | 0 601 338 A1 | 6/1994 |
| EP | 0 601 338 B1 | 6/1994 |
| EP | 0 601 338 B2 | 6/1994 |
| EP | 0 601 339 B1 | 6/1994 |
| EP | 0 601 340 A1 | 6/1994 |
| EP | 0 601 340 B1 | 6/1994 |
| EP | 0 646 391 A1 | 4/1995 |
| EP | 0 646 391 B1 | 4/1995 |
| EP | 0 669 839 B2 | 9/1995 |
| EP | 0 799 628 A3 | 4/1996 |
| EP | 0 779 080 B1 | 6/1997 |
| EP | 0 799 628 A2 | 10/1997 |
| EP | 0 813 886 A2 | 12/1997 |
| EP | 0 892 653 B1 | 1/1999 |
| EP | 1 106 202 A2 | 6/2001 |
| EP | 1 106 202 A3 | 3/2004 |
| EP | 0 813 886 A3 | 9/2004 |
| EP | 0 813 886 B1 | 9/2004 |
| GB | 2 157 178 A | 10/1985 |
| WO | WO 92/11898 | 7/1992 |
| WO | WO 92/17240 | 10/1992 |
| WO | WO 92/20401 | 11/1992 |
| WO | WO 94/07564 | 4/1994 |
| WO | WO 96/39098 | 12/1996 |
| WO | WO 97/31678 | 9/1997 |
| WO | WO 98/52641 | 11/1998 |
| WO | WO 99/34731 | 7/1999 |
| WO | WO 00/74557 A1 | 12/2000 |
| WO | WO 02/15824 A2 | 2/2002 |
| WO | WO 02/22208 | 3/2002 |
| WO | WO 02/055136 A3 | 7/2002 |
| WO | WO 02/056796 A1 | 7/2002 |
| WO | WO 02/064206 A2 | 8/2002 |
| WO | WO 2004/004603 A1 | 1/2004 |
| WO | WO 2004/028348 A2 | 4/2004 |
| WO | WO 2004/049919 A2 | 6/2004 |
| WO | WO 2004/058100 A2 | 7/2004 |
| WO | WO 2005/000398 A2 | 1/2005 |

OTHER PUBLICATIONS

File wrapper for U.S. Appl. No. 10/862,113 (U.S. Patent No. 7,529,589).

File wrapper for U.S. Appl. No. 10/454,223 (U.S. Patent No. 7,082,336).

File wrapper for U.S. Appl. No. 10/453,971 (U.S. Publication No. 2004/0249431).

File wrapper for U.S. Appl. No. 10/977,060 (U.S. Publication No. 2005/0228471).

File wrapper for U.S. Appl. No. 12/074,621 (U.S. Publication No. 2008/0154327).
File wrapper for U.S. Appl. No. 12/506,232 (U.S. Publication No. 2009/0281521).
File wrapper for U.S. Appl. No. 11/443,841 (U.S. Publication No. 2006/0224225).

* cited by examiner

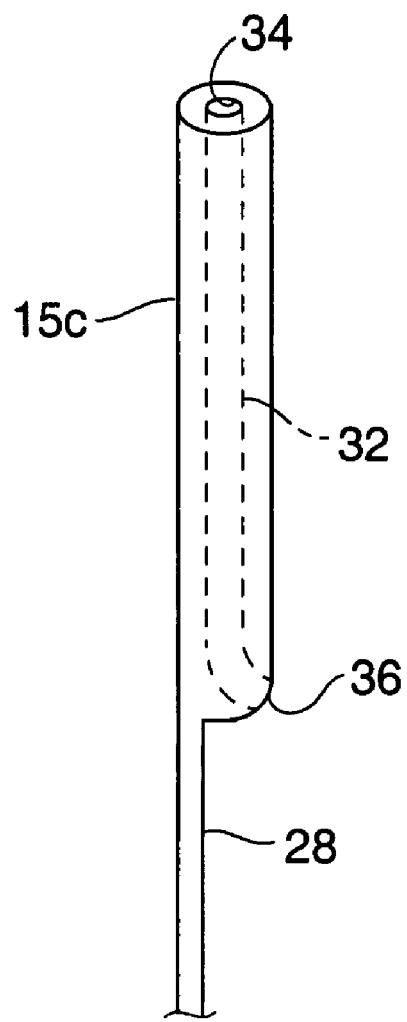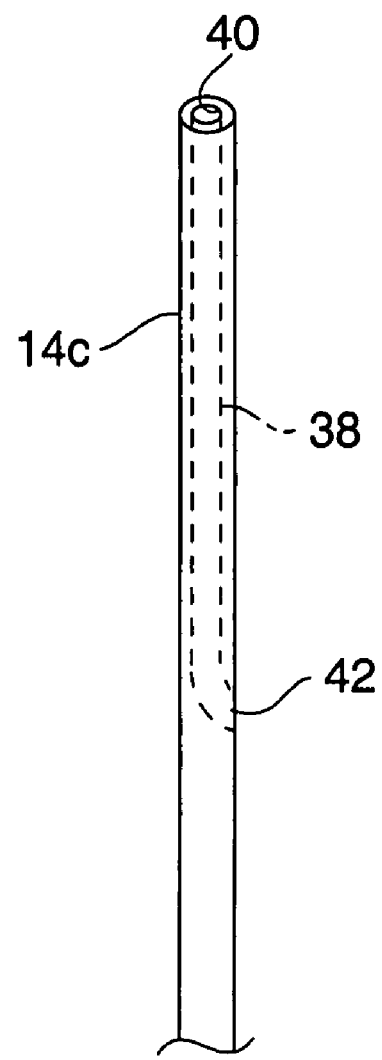
FIG. 2D  FIG. 2E

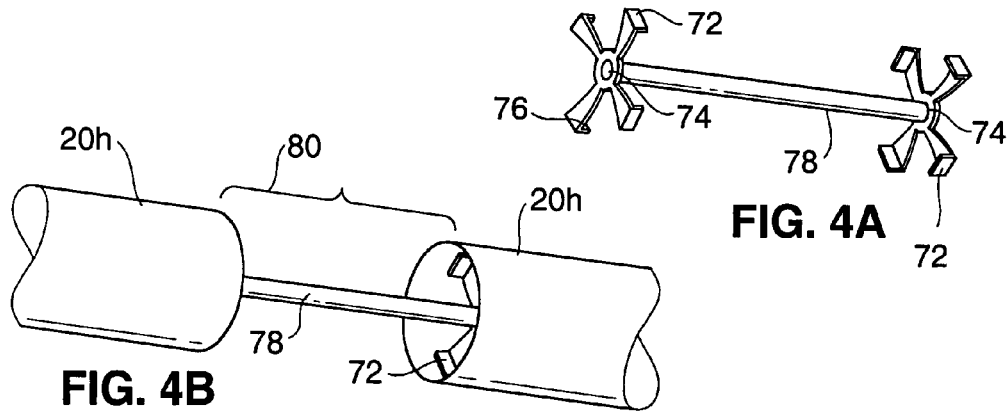
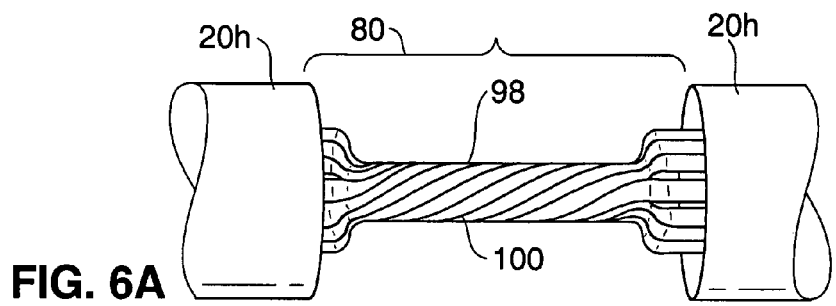
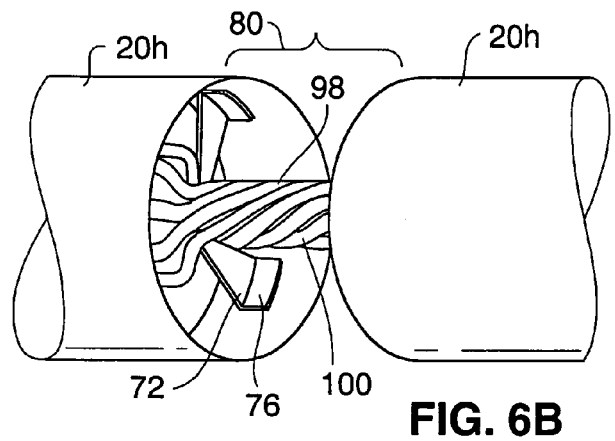
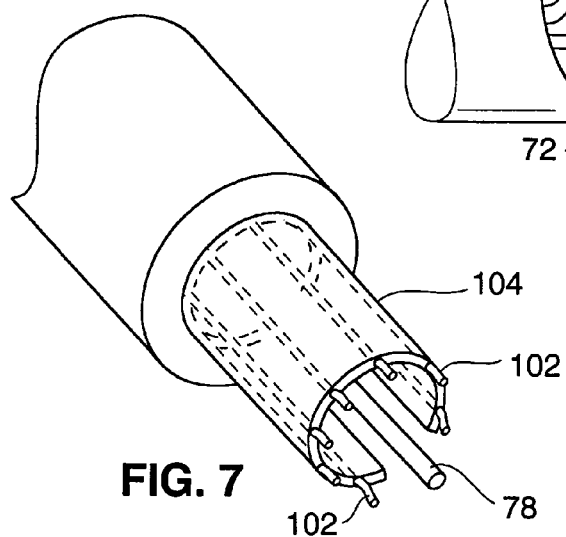

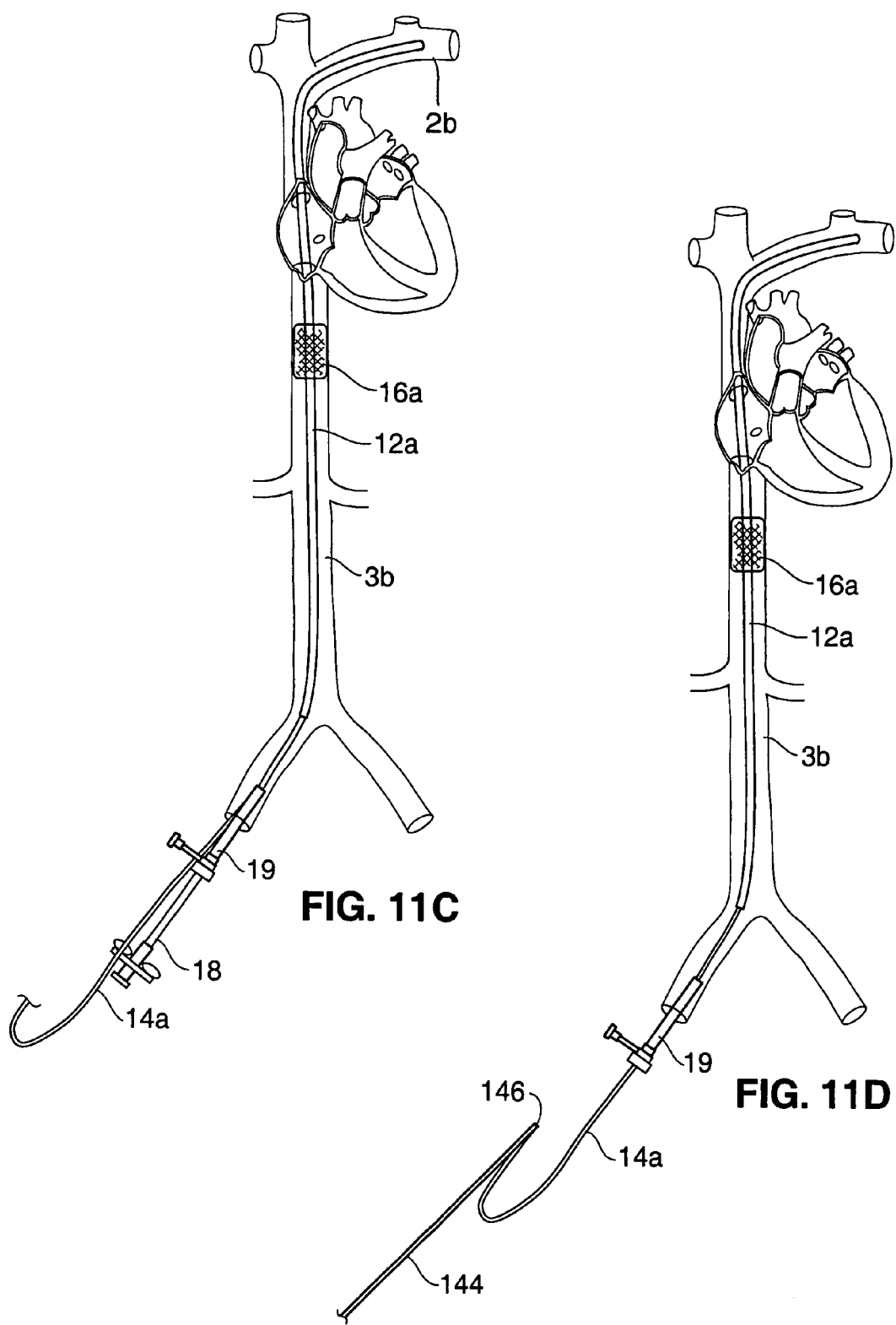

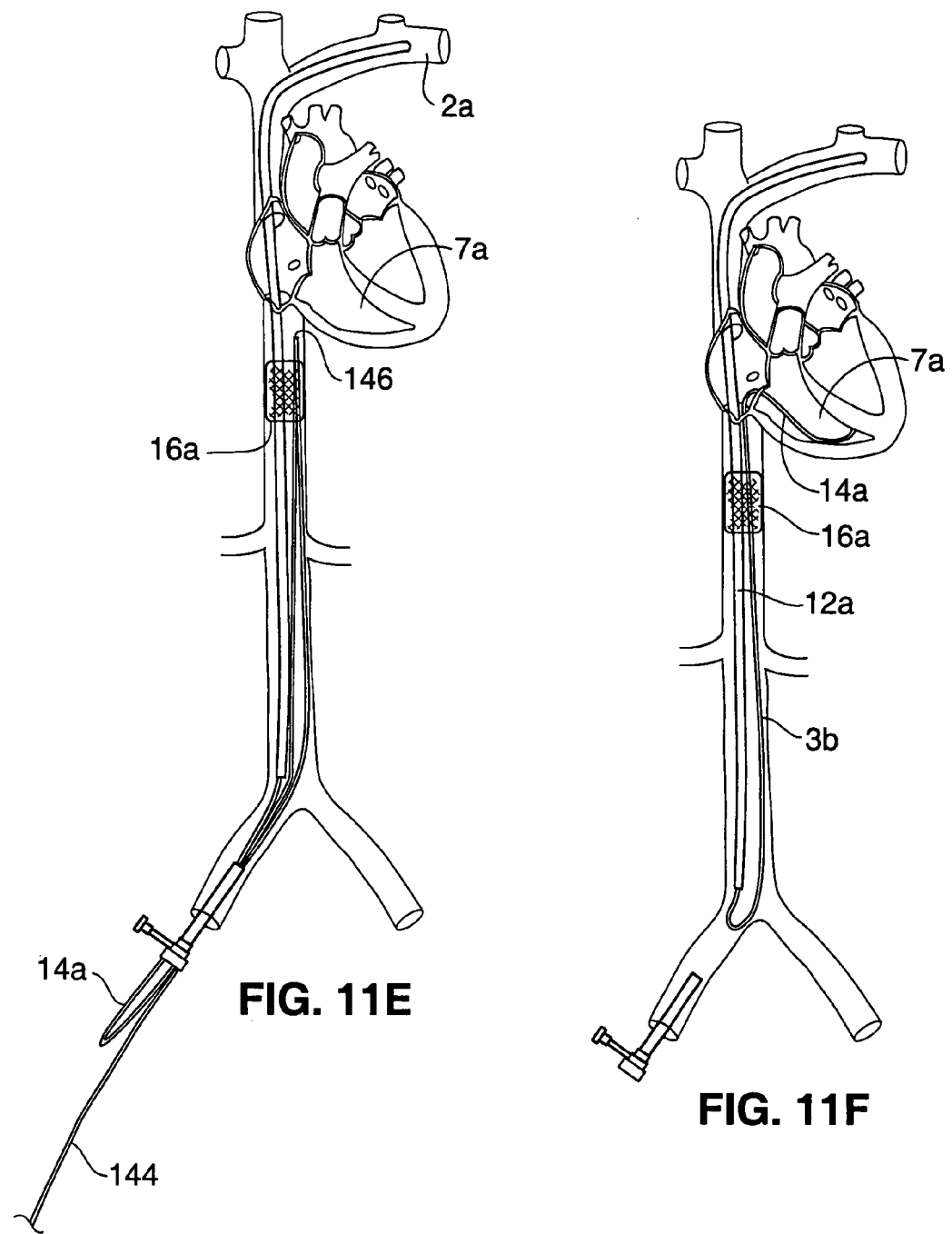

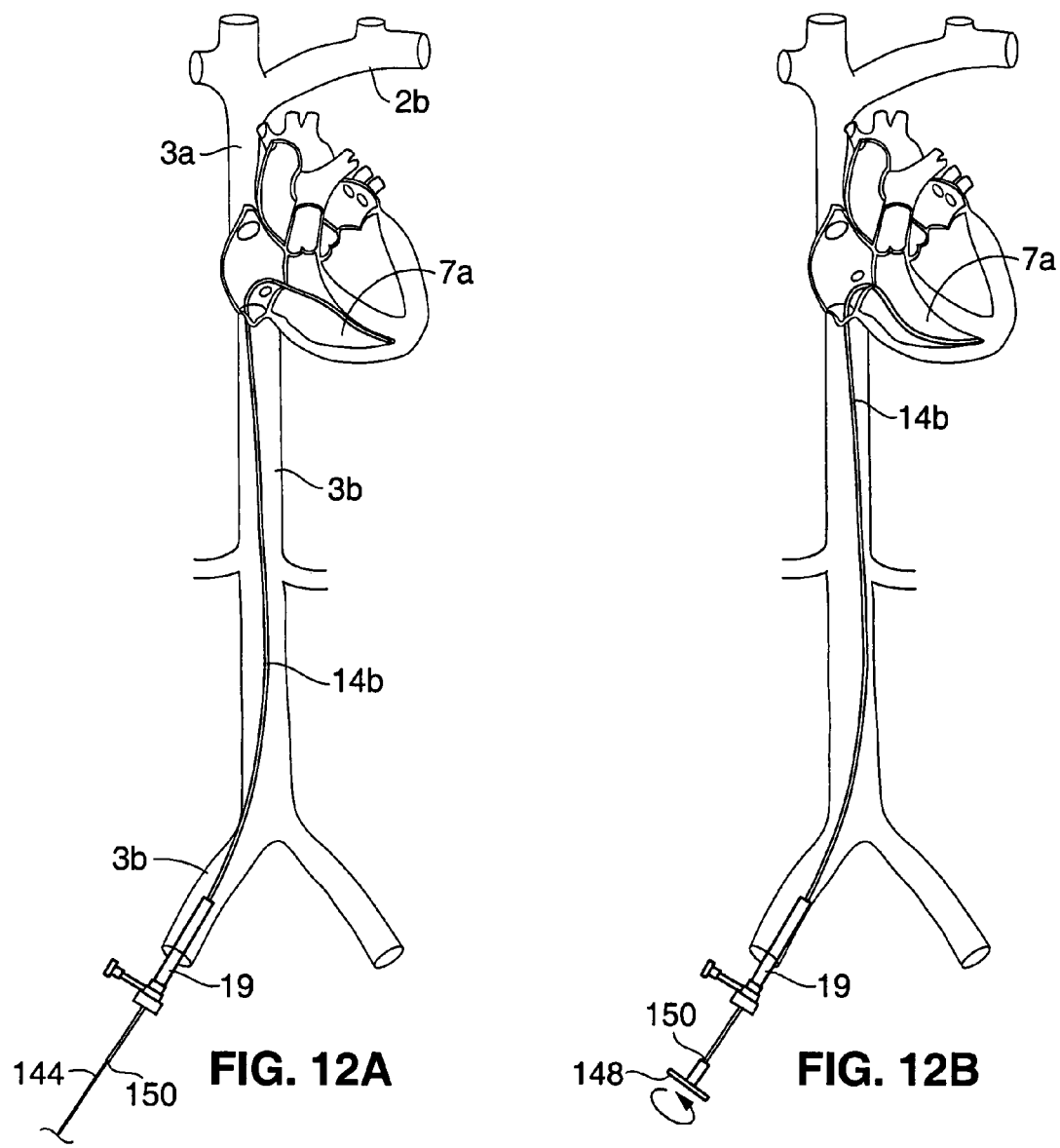

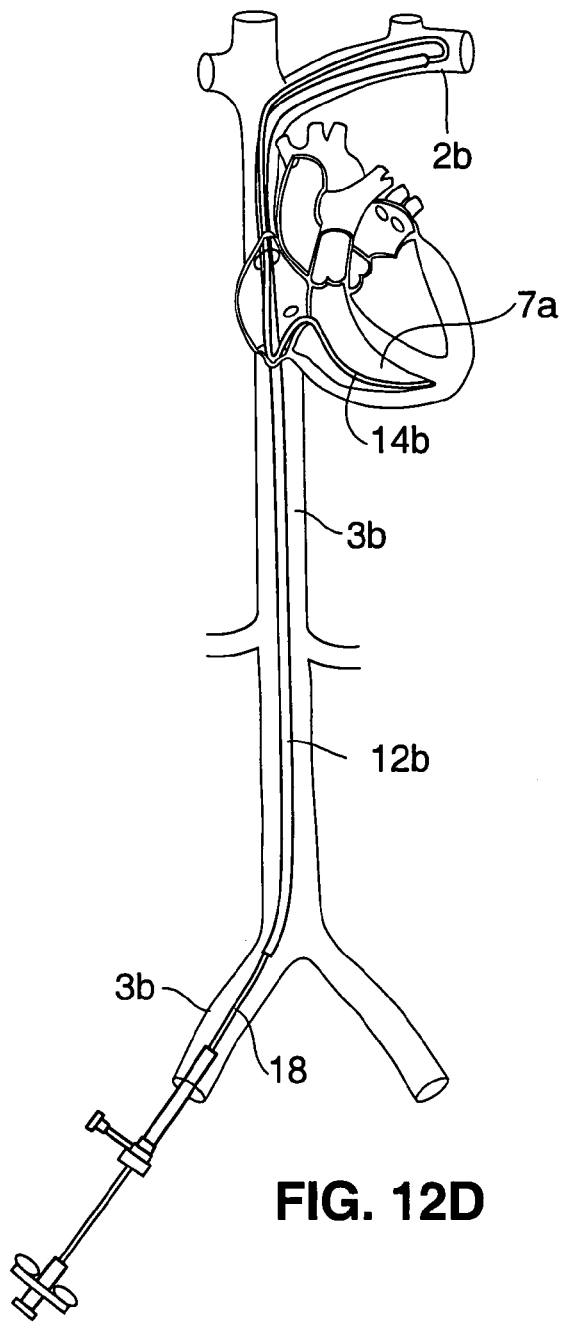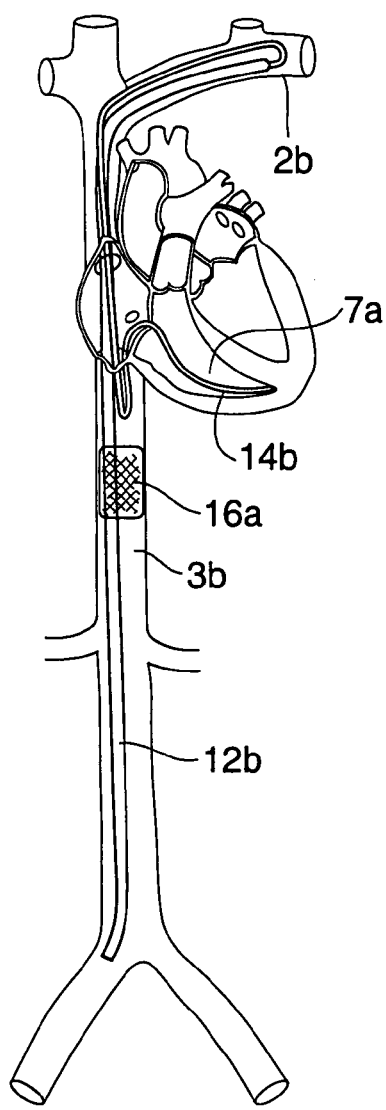
FIG. 12D
FIG. 12E

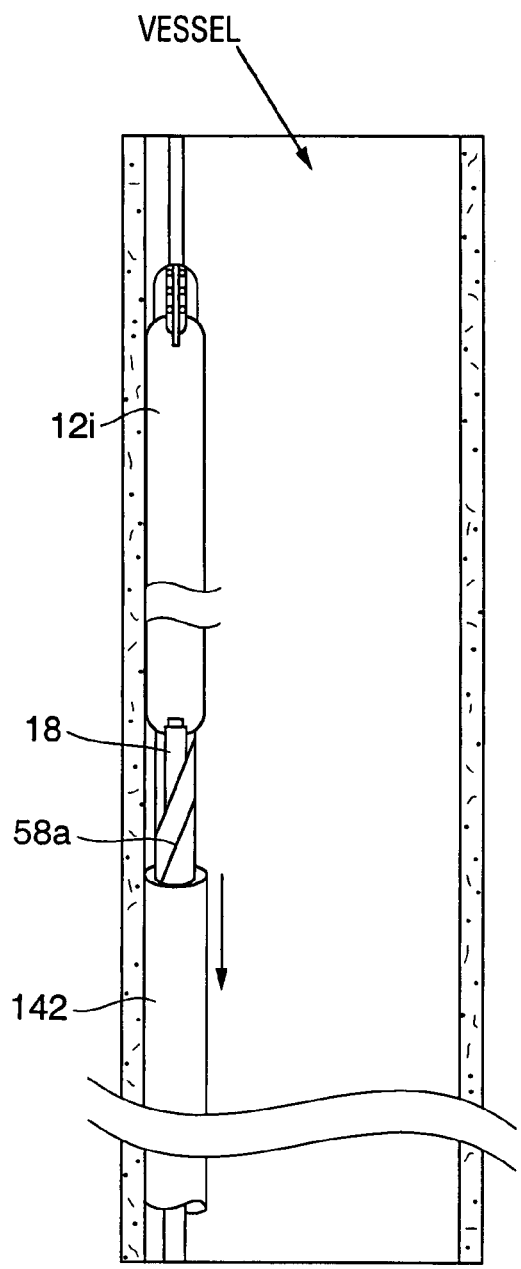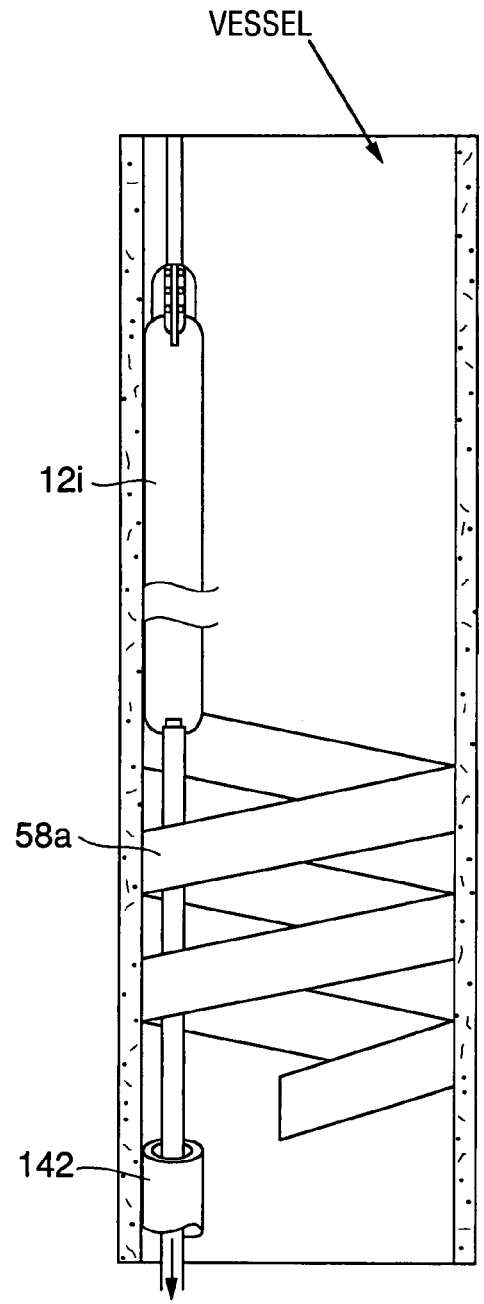
FIG. 14A
FIG. 14B

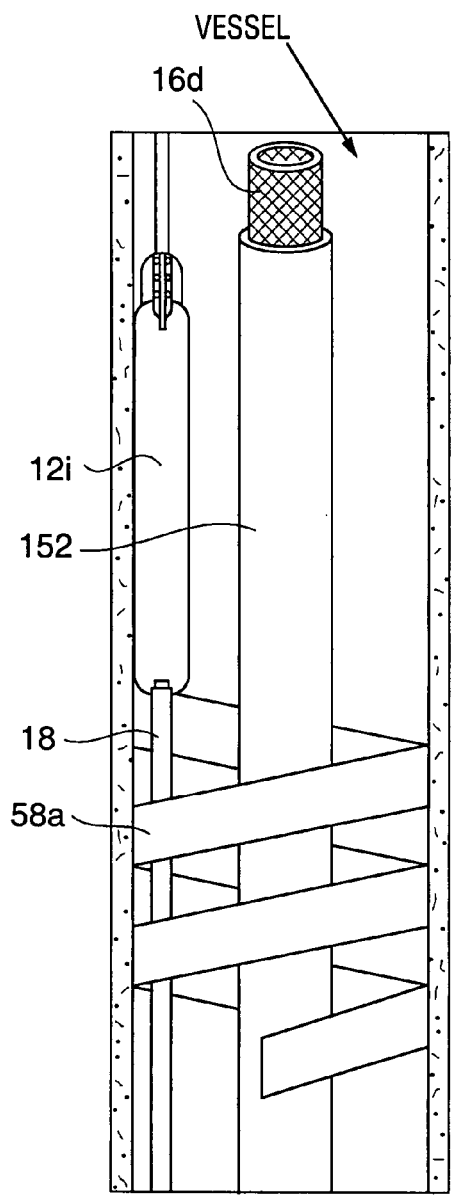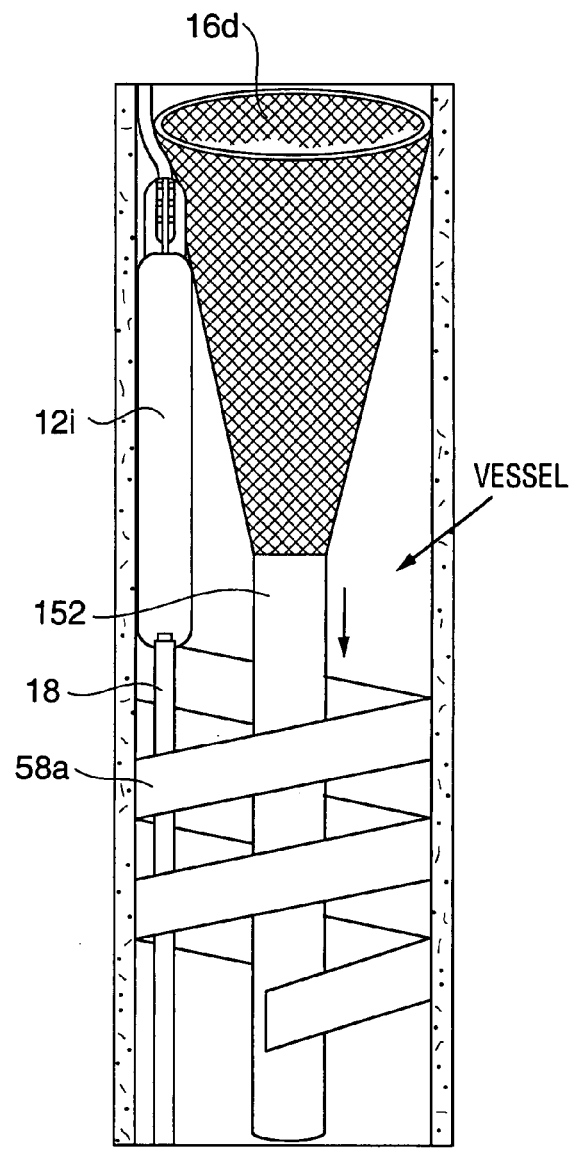
FIG. 14C  FIG. 14D

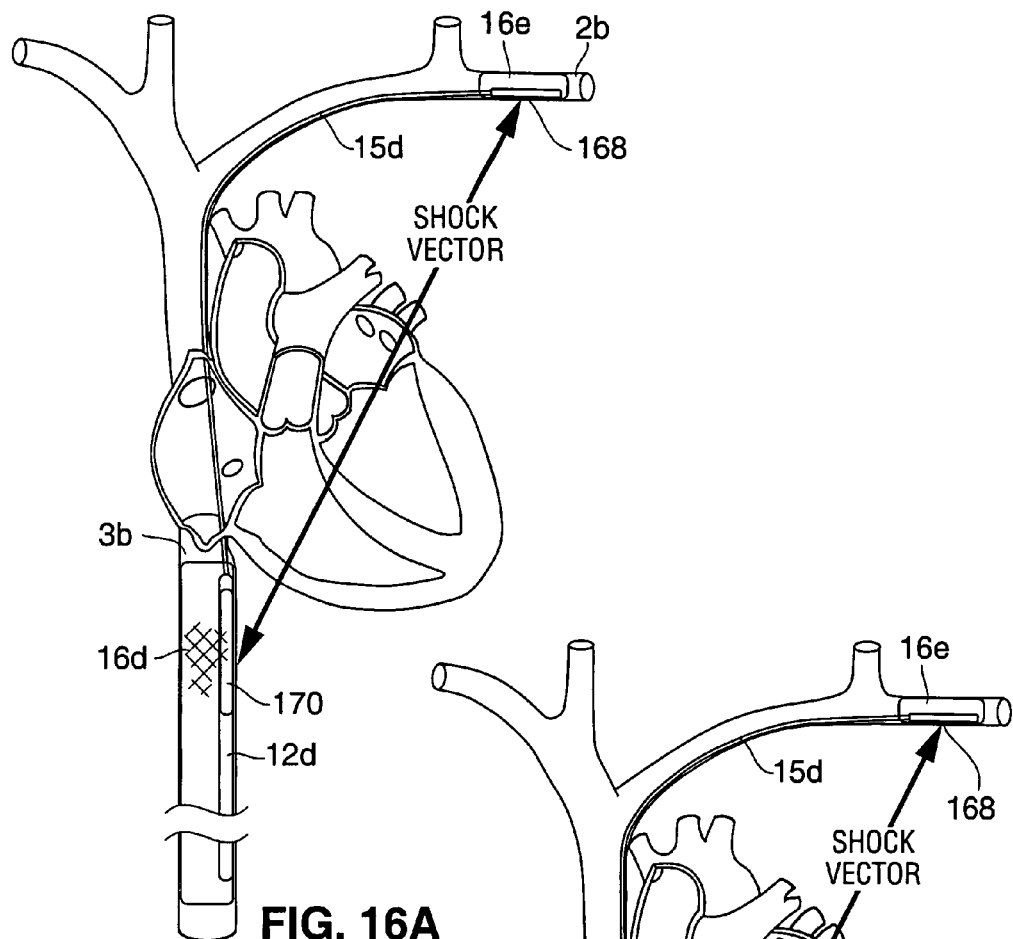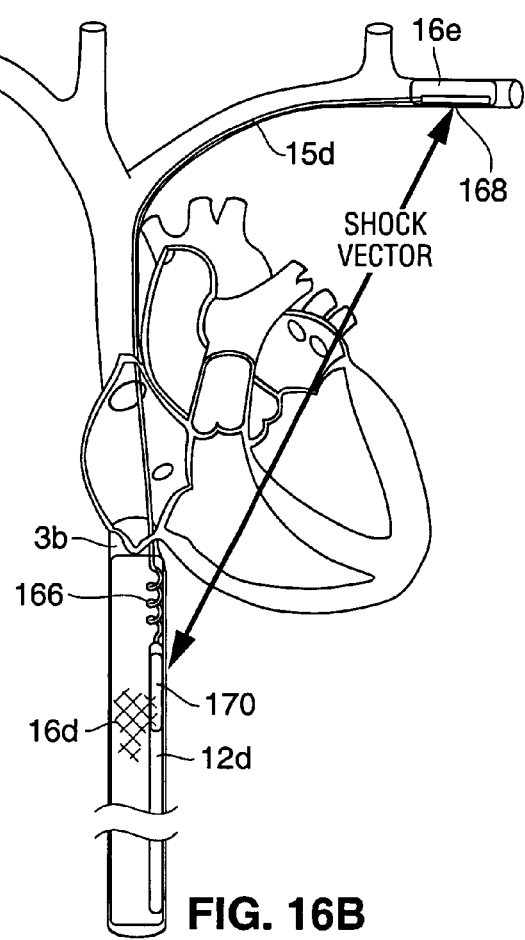
FIG. 16A
FIG. 16B

INTRAVASCULAR SYSTEM AND METHOD

PRIORITY

This is a divisional of U.S. application Ser. No. 10/862,113 now U.S. Pat. No. 7,529,589, filed Jun. 4, 2004, which is a continuation-in-part of U.S. application Ser. No. 10/454,223 now U.S. Pat. No. 7,082,336, filed Jun. 4, 2003, and claims the benefit of U.S. Provisional Application No. 60/515,746, filed Oct. 30, 2003, U.S. Provisional Application No. 60/516,026, filed Oct. 31, 2003, U.S. Provisional Application No. 60/525,332, filed Nov. 26, 2003, U.S. Provisional Application No. 60/525,336, filed Nov. 26, 2003, and U.S. Provisional Application No. 60/543,260, filed Feb. 10, 2004.

FIELD OF THE INVENTION

The present invention generally relates to devices, systems, and methods for diagnosing and treating the heart. In particular, the invention provides methods and systems for implanting medical devices into the patient's vasculature and using the devices for sensing electrical activity and/or electrically stimulating the heart

BACKGROUND OF THE INVENTION

Pacemakers, defibrillators and implanted cardioverter defibrillators ("ICDs") have been successfully implanted for years for treatment of heart rhythm conditions.

Pacemakers are implanted in patients who have bradycardia (slow heart rate). The pacemakers detect periods of bradycardia and deliver electrical stimuli to increase the heartbeat to an appropriate rate.

ICDs are implanted in patients who may suffer from episodes of fast and irregular heart rhythms called tachyarrhythmias. An ICD can cardiovert the heart by delivering electrical current directly to the heart to terminate an atrial or ventricular tachyarrhythmia, other than ventricular fibrillation. An ICD may alternatively defibrillate the heart in a patient who may suffer ventricular fibrillation (VF), a fast and irregular heart rhythm in the ventricles. During a VF episode, the heart quivers and can pump little or no blood to the body, potentially causing sudden death. An ICD implanted for correction of ventricular fibrillation will detect a VF episode and deliver an electrical shock to the heart to restore the heart's electrical coordination.

Another type of implantable defibrillation device treats patients who may suffer from atrial fibrillation (AF), which is a loss of electrical coordination in the heart's upper chambers (atria). During AF, blood in the atria may pool and clot, placing the patient at risk for stroke. An electrophysiological device implanted for correction of atrial fibrillation will detect an AF episode and deliver an electrical shock to the atria to restore electrical coordination.

Pacemakers and ICDs are routinely implanted in the pectoral region either under the skin (subcutaneous) or under the pectoral muscle. The leads are placed at appropriate locations within or on the heart. Because of this complexity, a cardiologist identifying a heart rhythm condition may be required to refer his or her patient to sub-specialists or surgeons for implantation of a pacemaker or ICD—thus delaying implantation of the device in a patient who urgently needs it. It is thus desirable to simplify these devices and the procedures for implanting them so as to permit their implantation by a broader range of physicians.

SUMMARY OF THE INVENTION

The present application describes an intravascular implantable electrophysiological system that may carry out cardioversion, pacing and/or defibrillation of a human heart. The described system includes a pulse generator that is implantable within a blood vessel and/or the heart and electrodes coupled to the pulse generator. During implantation, the pulse generator is introduced into a patient's vasculature, advanced to a desired vessel and anchored in place within the vessel. The electrode(s) are positioned within the heart or surrounding vessels as needed to deliver electrical pulses to the appropriate location.

BRIEF DESCRIPTION OF THE DRAWINGS

FIGS. 2D and 2E are side elevation views of distal portions of the leads of the system of FIG. 2C.

FIG. 4A is a perspective view illustrating the coupler and rod of the embodiment of FIG. 3E. FIG. 4B is a perspective view illustrating the coupler and rod assembly of FIG. 4A in combination with a pair of device enclosures.

FIG. 5A is an end view showing a device component and end cap, and FIG. 5B is a cross-sectional side view taken along the plane designated 5B-5B in FIG. 5A. FIGS. 5C and 5D are similar to FIGS. 5A and 5B, respectively, but show the component and end cap combined with a flex circuit, enclosure and coupler. FIG. 5E is similar to FIG. 5D but adds the conductor assembly, rod and elastomer.

FIGS. 6A and 6B are perspective views showing a pair of enclosures with a conductor assembly extending between them.

FIG. 7 is a perspective end view of an enclosure showing an alternate conductor assembly extending from the enclosure for coupling to associated components in a second enclosure.

FIGS. 11A-11F are a sequence of drawings schematically illustrating implantation of the system of FIG. 2A.

FIGS. 12A-12E are a sequence of drawings schematically illustrating implantation of the system of FIG. 2B.

FIGS. 14A-F are a sequence of drawings schematically illustrating implantation of the system of FIG. 8A.

DETAILED DESCRIPTION OF THE DRAWINGS

Cardiac Anatomy

Figure 1:
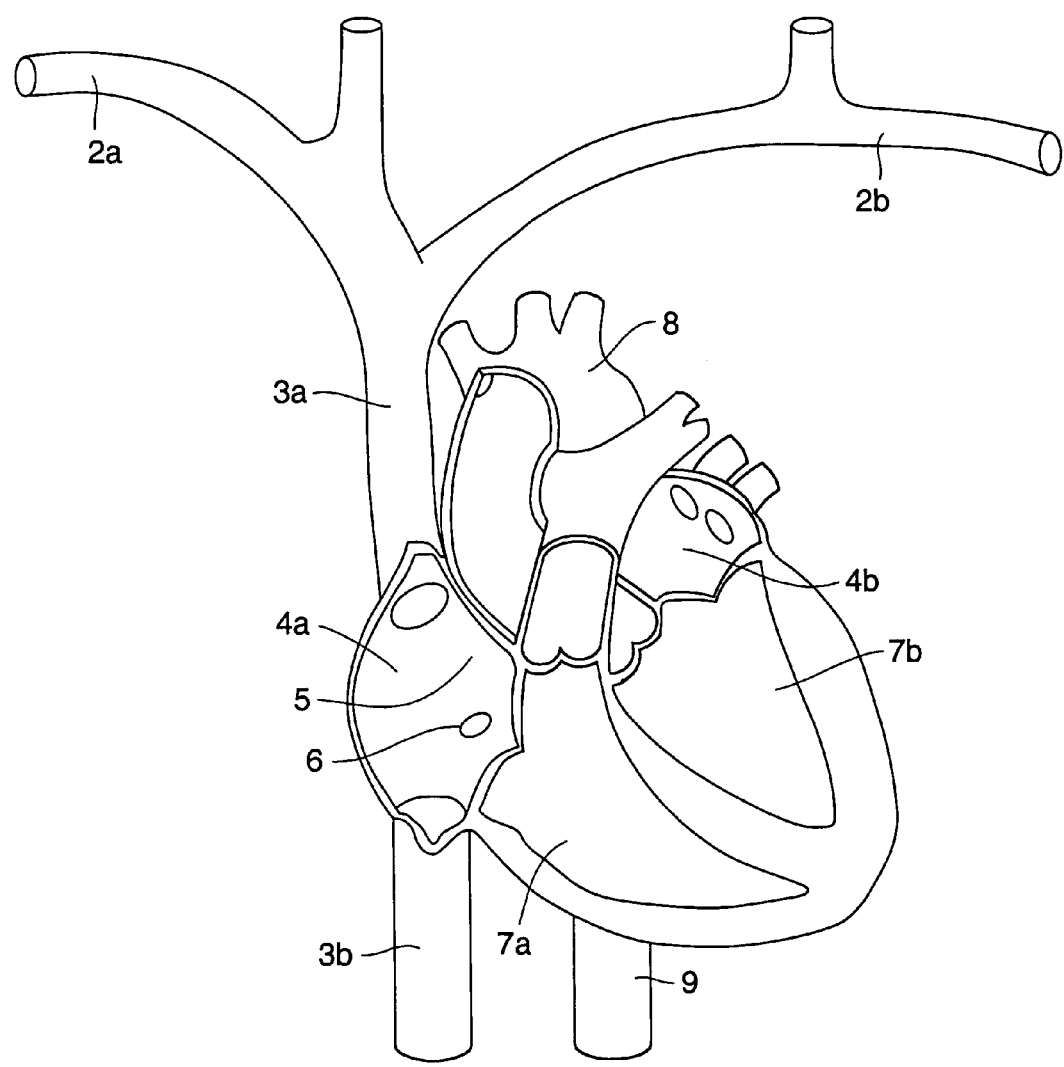
FIG. 1 is a perspective illustration showing human cardiac anatomy.

FIG. 1 shows the cardiac anatomy of a human, including the heart and major vessels. The following anatomic locations are shown and identified by the listed reference numerals:

| | |
|---|---|
| Right Subclavian | 2a |
| Left Subclavian | 2b |
| Superior Vena Cava (SVC) | 3a |
| Inferior Vena Cava (IVC) | 3b |
| Right Atrium (RA) | 4a |
| Left Atrium (LA) | 4b |
| Right Atrial Appendage (RAA) | 5 |

-continued

| | |
|---|---|
| Coronary Sinus Ostium (CS Os) | 6 |
| Right Ventricle (RV) | 7a |
| Left Ventricle (LV) | 7b |
| Aortic Arch | 8 |
| Descending Aorta | 9 |

System Components

Generally speaking, the present disclosure describes intravascular electrophysiological systems that may be used for a variety of functions. These functions include defibrillation, pacing, and/or cardioversion. In general, the elements of the systems described below include at least one device body and typically, but optionally, at least one lead coupled to the body. One or more retention devices may facilitate retention of the device body and/or leads or other elements within the vasculature. Also described are components such as mandrels, stylets and/or guidewires used to facilitate implantation of the system.

FIGS. 2A through 2F illustrate systems well suited for use as defibrillators used in the treatment of tachyarrhythmias. Although the description of these systems focuses on their use in the treatment of ventricular tachycardia, systems such as these, or modifications thereof, may be used for various other electophysiologic applications, some of which are described in connection with FIGS. 16A through 19.

Figure 2A:
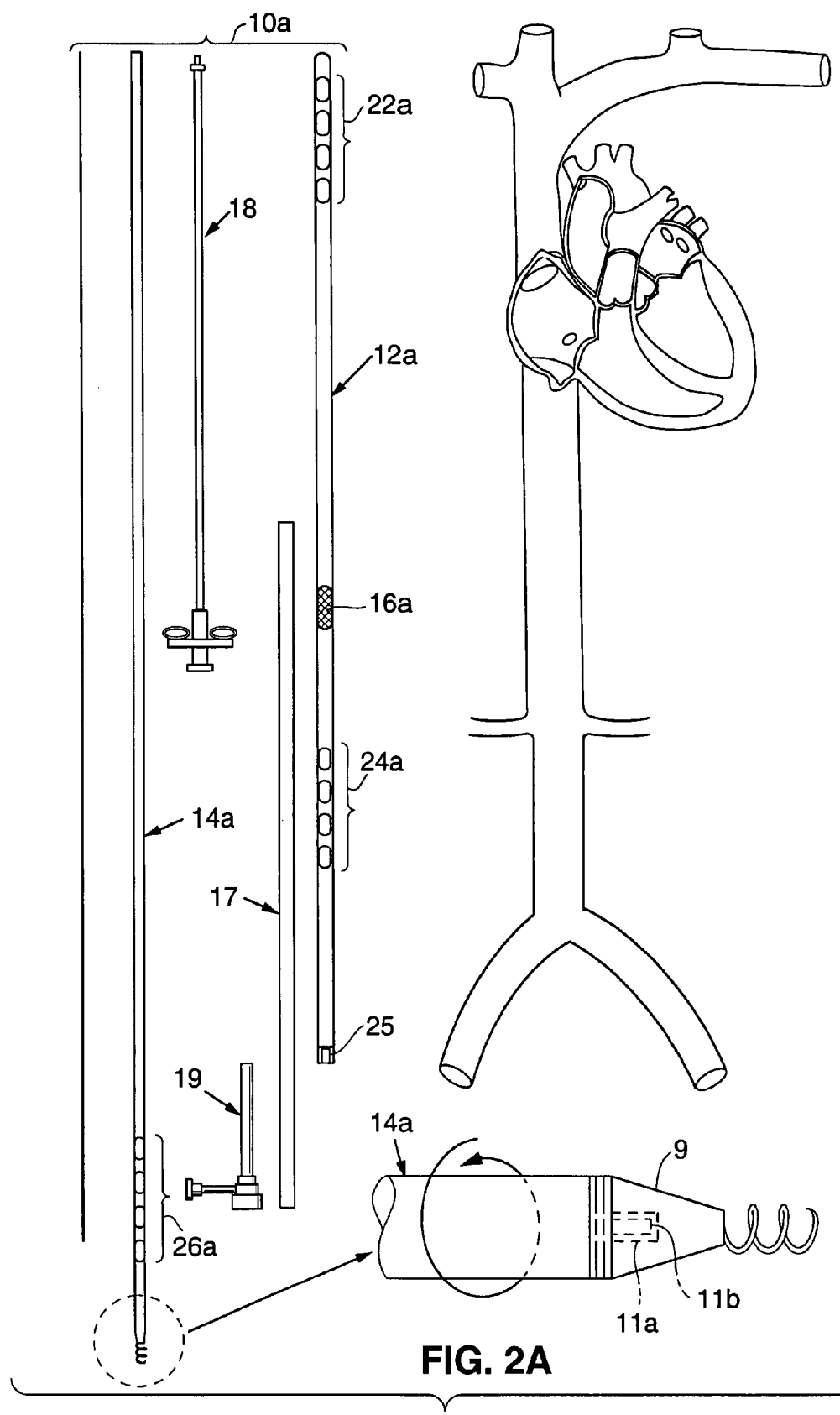
FIG. 2A is a plan view generally showing components of one form of intravascular electrophysiological system which utilizes a lead on the inferior portion of the device body.

One configuration of an electrophysiological system 10a is shown in FIG. 2A. The elements of the FIG. 2A system 10a include an elongate device body 12a, lead 14a, retention device 16a, a sleeve 17, a positioning mandrel 18 and an introducer sheath 19. It should be understood that certain of these elements may be eliminated, or others added to the system, without departing from the spirit of the invention.

Device 12a houses components known in the art to be necessary to carry out the system functions. For example, device 12a may include one or more pulse generators, including associated batteries, capacitors, microprocessors, and circuitry for generating electrophysiological pulses for defibrillation, cardioversion and/or pacing. Device also includes detection circuitry for detecting arrhythmias or other abnormal activity of the heart. The specific components to be provided in the device will depend upon the application for the device, and specifically whether the device is intended to perform defibrillation, cardioversion and/or pacing along with its sensing functions.

The device 12a is proportioned to be passed into the vasculature and to be anchored within the patient's vasculature with minimal obstruction to blood flow. Suitable sites for the device 12a may include, but are not limited to the venous system using access through the right or left femoral vein or the subclavian or brachiocephalic veins, or the arterial system using access through one of the femoral arteries. Thus, the housing of device 12a preferably has a streamlined maximum cross sectional diameter which may be in the range of 3-15 mm or less, with a most preferred maximum cross-sectional diameter of 3-8 mm or less. The cross-sectional area of the device in the transverse direction (i.e. transecting the longitudinal axis) should be as small as possible while still accommodating the required components. This area is preferably in the range of approximately 79 mm$^2$ or less, and more preferably in the range of approximately 40 mm$^2$ or less, or most preferably between 12.5-40 mm$^2$.

The cross-section of the device (transecting the longitudinal axis) may have a circular cross-section, although other cross-sections including crescent, flattened, or elliptical cross-sections may also be used. It is highly desirable to provide the device with a smooth continuous contour so as to avoid voids or recesses that could encourage thrombus formation on the device.

A first array of electrodes 22a is positioned on a superior region of the device body 22a, and a second array of electrodes 24a is positioned on an inferior region. Individual electrodes may be used in place of the arrays. Electrodes 22a, 24a are preferably positioned on the surface of the device 12a. For example, electrodes 22a, 24a may take the form of conductive elements attached to the non-conductive housing of the device 12a. Alternatively, if the device includes a conductive housing to which an insulating material is to be applied, the electrodes may be formed by selectively applying the coating or removing portions of the coating to leave one or more exposed electrode regions on the surface of the device 12a. As yet another alternative, the retention device 16a in this and the other embodiments may include conductive elements and function as an electrode.

A proximal portion of the device includes a connector 25 for receiving the distal end of positioning mandrel 18, which may be used to steer the device 12a (by pushing, pulling and/or torquing) through the patient's vasculature as described below. The connector 25 may take the form of a threaded bore for receiving a threaded screw member at the distal end of the mandrel 18, or it may have any other type of configuration for detachably engaging the distal end of the mandrel.

Mandrel 18 may serve purely mechanical purposes, or it may also be a "smart mandrel" that provides electrical and/or fluid connections. Such connections can be used to couple the device (via an instrument cable) for electrical, electronic, and/or fluid communication between the device and instrumentation located outside the body. This communication may be used several purposes, including device testing, initiation and/or programming during implantation, and/or recharging of the device battery. If the device is to be used for drug delivery, the mandrel may be used for re-filling a reservoir in the device with pharmaceutical agents that may be deliverable by the device to a patient.

Lead 14a is attachable to the inferior end of device 12a as will be described in detail in the "Implantation" section, although the lead 14a may be instead integrally connected to device. Lead 14a includes one or more defibrillation and/or pacing electrodes 26a and may also be equipped to sense electrical activity of the heart. Monitoring of the heart's electrical activity is needed to detect the onset of an arrhythmia. Activity sensed by the sensing electrode(s) is used by the device electronics to trigger delivery of a defibrillation shock. Additional leads may be provided if desired.

The lead 14a may be a conventional defibrillation/pacing lead, although alternative lead configurations may be desirable if warranted by the desired placement of the device 12a and lead within the body. For example, the physician will preferably want to select a location for the device within a chosen vessel (e.g. the inferior or superior vena cava) that will prevent the device from blocking significant peripheral vessels extending from that vessel. An optimal lead will preferably give the physician implanting the device flexibility to position the device at an appropriate location in the chosen vessel without concern that the leads extending from the device will not reach their intended location. Thus, for some patients it may be necessary to use a lead that is slightly longer than conventional leads, or the lead may include a coiled section (see coiled section 166 of FIG. 16B) that is similar to the configuration of a coiled telephone cord. A coiled section can allow elongation of the effective length of the lead when tension is applied to the coil. The coiled section or any alternate type of yieldable lead section may be a plastically deformable metal or polymer that will retain its extended configuration after it has been stretched to that configuration Other configurations that will allow additional lead length to pay out from the device if needed may also be used.

For leads that are to be positioned within a chamber of the heart, the leads may be the helical screw-in or tined variety for fixation to the cardiac tissue, and/or they may have steroid-eluding tips to facilitate tissue in-growth for fixation purposes. As illustrated in FIG. 2A, a detachable screw-in lead tip 9 may be detachable from the lead 14a. This allows the lead tip 9 to be left within the chamber of the heart when the remainder of the lead 14a, so as to prevent damage to the heart tissue as could occur upon extraction of the helical tip. Tip 9 preferably includes a torque socket 11a which mates with a corresponding wire torque element 11b on the lead body 14a to optimize torque transmission when the lead tip 9 is screwed into the heart tissue.

The leads may include non-thrombogenic and/or non-proliferative surfaces or coatings as also described above in connection with the Device Configuration section below. For example, the leads may include a coating that is anti-thrombogenic (e.g. perfluorocarbon coatings applied using super-critical carbon dioxide) so as to prevent thrombus formation on the lead. It is also beneficial for the coating to have anti-proliferative properties so as to minimize endothelialization or cellular ingrowth, since minimizing growth into or onto the lead will help minimize vascular trauma when the device is explanted. The coating may thus also be one which elutes anti-thrombogenic compositions (e.g. heparin sulfate) and/or compositions that inhibit cellular in-growth and/or immuno-suppressive agents.

It should also be noted that the lead may be attachable to the device 12a in situ or prior to implantation, or it may be permanently attached to the device, or it may be integral with the device as an elongate extension of the device itself. Thus it should be appreciated that in this disclosure the term "lead" is used to mean an element that includes conductors and electrodes and that thus may be positioned somewhat remotely from the circuitry that energizes the electrodes. Thus, leads may include elements that are simply extensions or tapers of the device 12a itself (such as the portion of the device 12a at which electrodes 22a are located) as well as more conventional leads.

Figure 2B:
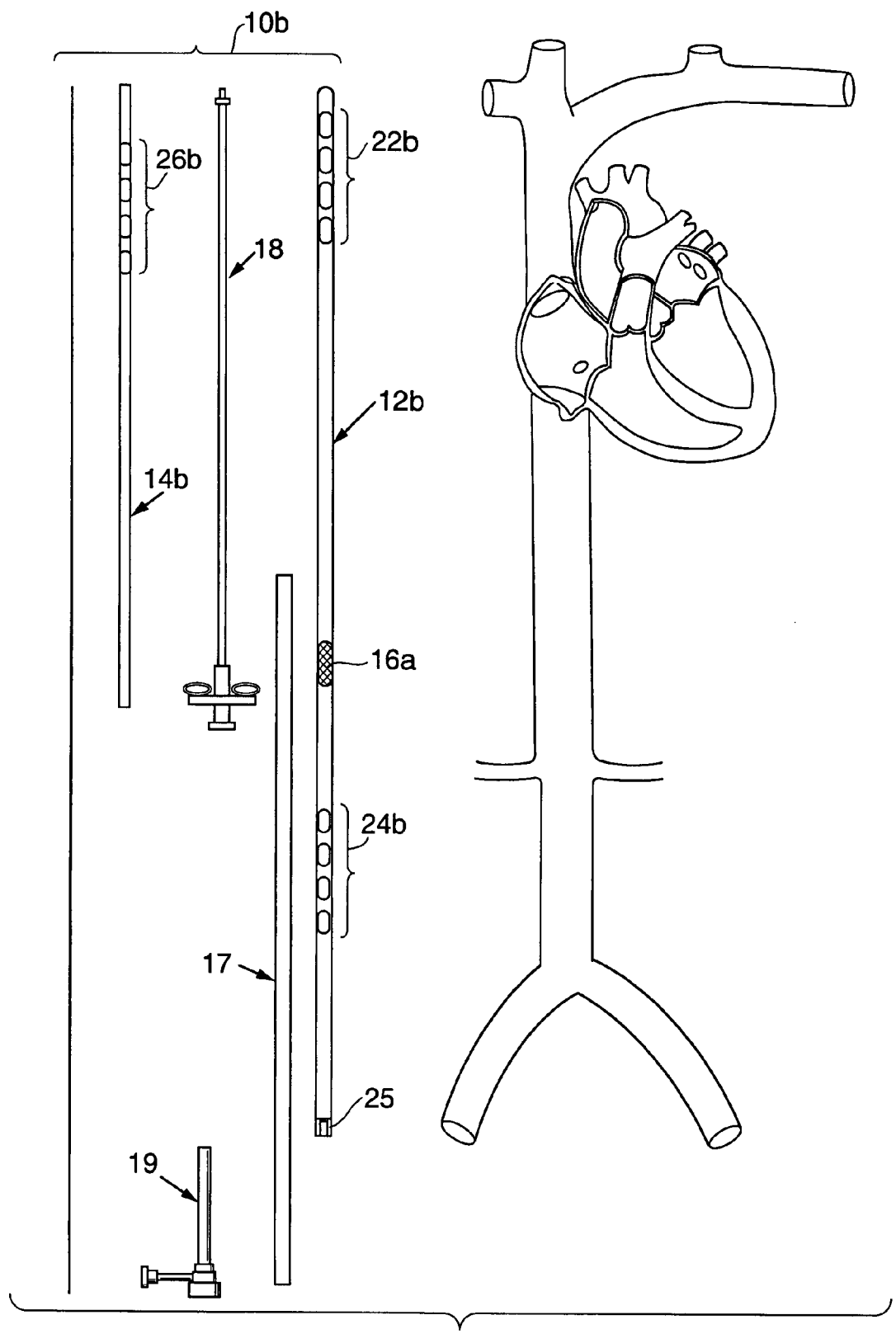
FIG. 2B is a plan view generally showing components of a second form of intravascular electrophysiological system, which utilizes a lead on the superior portion of the device body.

A second embodiment of a system 10b is shown in FIG. 2B and differs from the FIG. 2A embodiment primarily in that its lead 14b is attachable (or integrally attached) to the superior end of device 12b.

Figure 2C:
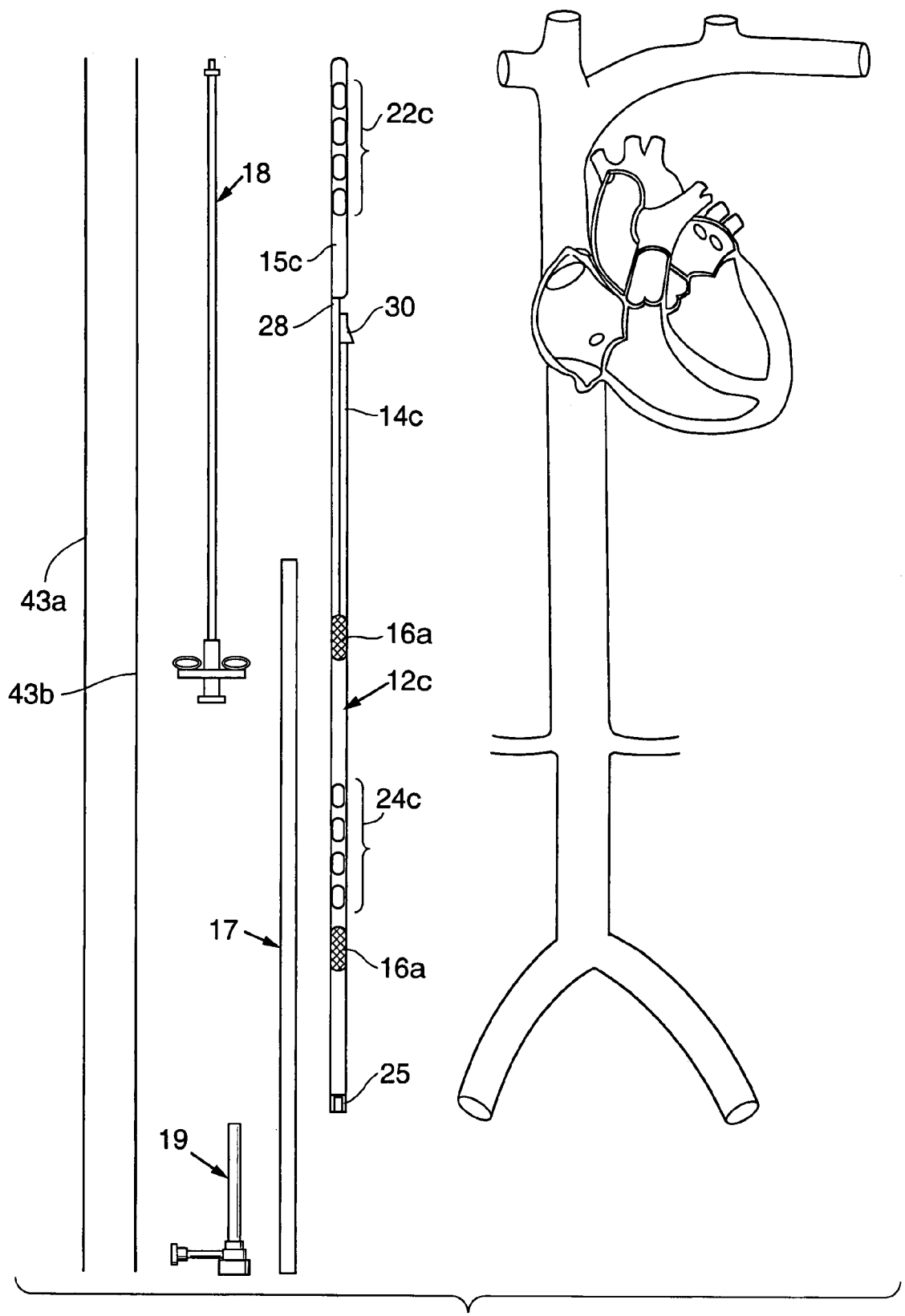
FIG. 2C is a plan view generally showing components of a third form of intravascular electrophysiological system, which has a bifurcated configuration.

The third embodiment of FIG. 2C includes two leads 14c, 15c, both extending from the superior end of the device 12c. Either or both of the leads may be attachable or detachable from the device 12c, permanently attached to the device, or integral with the device as an elongate extension of the device itself. Lead 15c preferably includes one or more defibrillation electrodes 22c and lead 14c preferably includes at least one defibrillation electrode (not shown). Either or both of the leads may also be equipped to sense electrical activity of the heart so as to identify onset of an arrhythmia.

Because the leads extend from one end of device 12c, the leads 14c, 15c will be positioned side-by-side within a blood vessel at some point, at least during implantation of the system. Thus, the diameters of the leads are proportioned to permit continued blood flow through the vessel even when the leads are side-by-side. In the shown embodiment, lead 15c is longer than lead 14c, and includes a narrow section 28 along the portion of the lead 15c that is adjacent to lead 14c. Thus, the combined diameters of narrow section 28 and lead 14c must be small enough to fit through the vessels through which they will be passed, and preferably do not exceed the maximum diameter of device 12c. In one example, lead 15c includes a diameter of 1-10.0 mm except at narrow section 28 which has a diameter of 0.5-9.5 mm; lead 14c has a diameter of 1-10 mm; and device 12c has a diameter of 3-15 mm. It should also be noted that a breakaway retention means 30 might be provided for coupling the narrow section 28 of lead 15c with the lead 14c during advancement of the device 12c through the vasculature.

The leads may include non-thrombogenic, non-proliferative and/or anti-inflammatory surfaces or coatings as also described above in connection with the device 12a.

Each lead 14c, 15c includes a guidewire lumen to aid in implantation of the lead. Referring to FIG. 2D, lead 15c includes guidewire lumen 32 which extends between opening 34 and opening 36. Likewise, as shown in FIG. 2E, a guidewire lumen 38 in lead 14c extends between openings 40 and 42. Naturally, the leads may be provided with alternative ways of receiving guidewires, many of which are known in the art and/or described below. As shown in FIG. 2C, the system may include guidewires 43a, 43b for use in implanting the leads 14c, 15c.

Figure 2F:
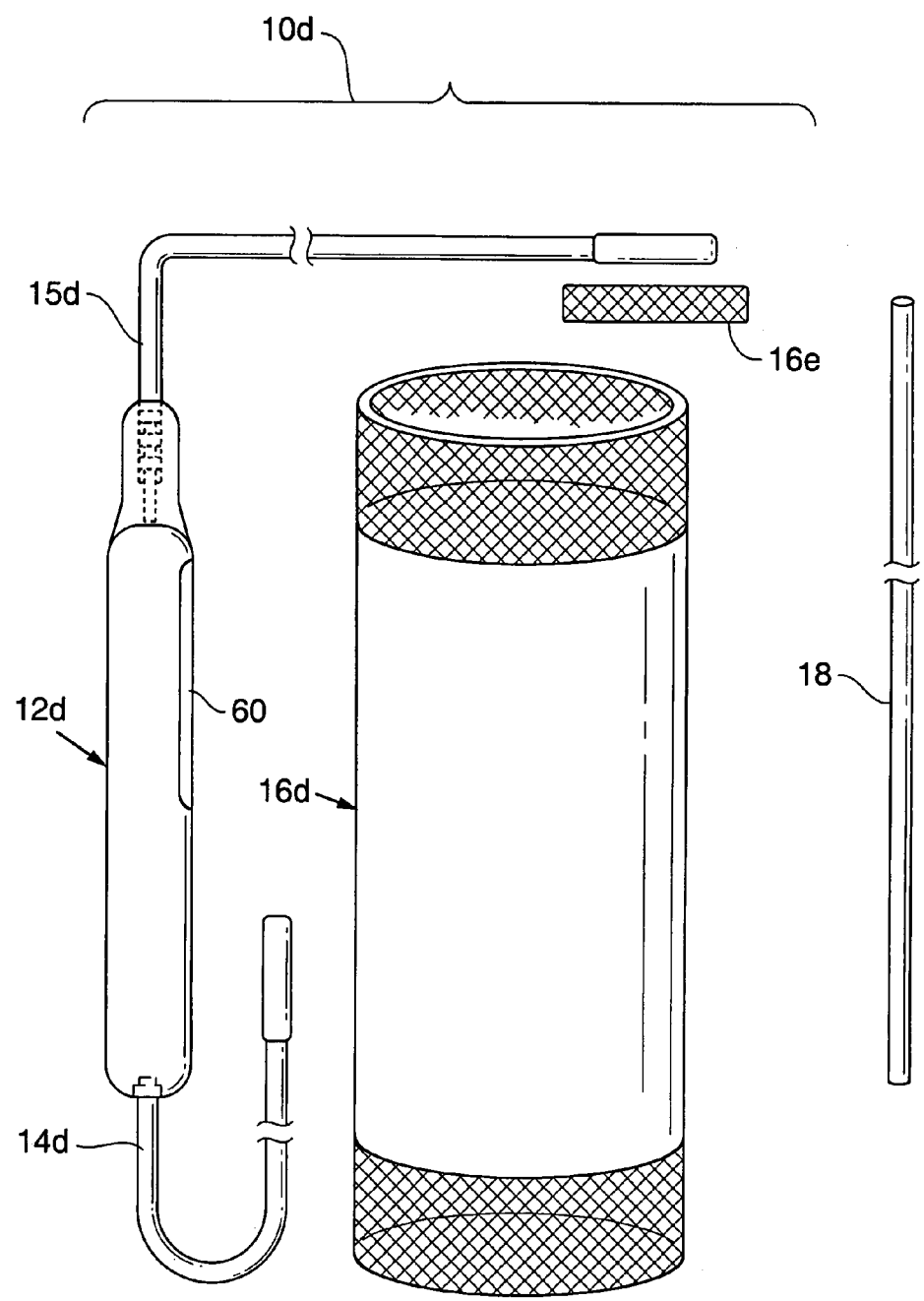
FIG. 2F is a plan view generally showing components of a fourth form of intravascular electrophysiological system which utilizes leads on the inferior and superior portions of the device body.

FIG. 2F shows a fourth embodiment of a system 10d, which also includes a pair of leads 14d, 15d but which differs from the system 10c of FIG. 2C in that the leads extend from opposite ends of the device 12d. As with the previous embodiments, the leads may be attachable/detachable to/from the device 12d, permanently attached to the device, or integral with the device as an elongate extension of the device itself. The retention device 16d differs from the retention devices 16 of the systems of FIGS. 2A, 2B and 2C in that it is provided as a separate component rather than being integral with the device 12d. Moreover, an additional retention device 16e is provided for anchoring the lead 15d. Details concerning the retention devices are set forth below in the section entitled "Retention Devices" describing FIGS. 9A-10E.

Device Configuration

Given the minimal space allowed for components, it is desirable to arrange the device components so as to make efficient use of the available space. Examples of devices having space efficient arrangements of their contents are shown in FIGS. 3A, 3B, 3C, 3E, and 8A. The features of these devices are applicable to any of the systems described herein.

Figure 3A:
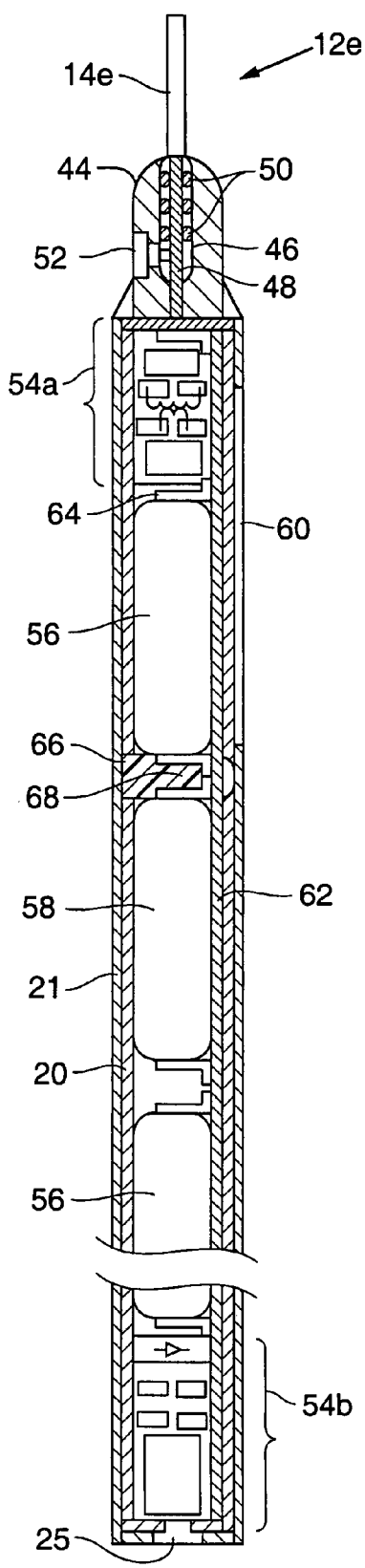
FIG. 3A is a plan view showing a first embodiment of an intravascular electrophysiological device of a type which may be used with the systems shown in FIGS. 2A-2F.

A first example is identified by reference numeral 12e in FIG. 3A. Device 12e includes an elongate enclosure 20 shown in cross-section in FIG. 3A to allow the components housed within it to be seen. Enclosure 20 is a rigid, semi-rigid or flexible housing preferably formed of a material that is biocompatible, capable of sterilization and capable of hermetically sealing the components contained within the enclosure 20. The housing may be formed of a molded compound. Alternatively, a conductive material such as titanium, stainless steel, or other materials may be used.

The housing is preferably covered by a layer or coating 21, which may be electrically insulative particularly if the enclosure 20 is conductive. One example of such a coating is ePTFE. It is desirable to provide a coating that is anti-thrombogenic (e.g. perfluorocarbon coatings applied using supercritical carbon dioxide) so as to prevent thrombus formation on the device. It is also beneficial for the coating to have anti-proliferative properties so as to minimize endothelialization or cellular ingrowth, since minimizing growth into or onto the device will help minimize vascular trauma when the device is explanted. The coating may thus also be one which elutes anti-thrombogenic compositions (e.g. heparin sulfate) and/or compositions that inhibit cellular in-growth and/or immunosuppressive agents. If the enclosure 20 is conductive, this layer or coating may be selectively applied or removed to leave an exposed electrode region 60 on the surface of the enclosure 20.

FIG. 3A illustrates one means for detachably connecting a lead 14e to the device 12e. In this embodiment, device 12e includes a header 44 having a socket 46. To attach lead 14e to the device 12e, a pin 48 at the proximal end of lead 14e is inserted into socket 46. A series of o-ring seals 50 surround the pin 48 within the socket 46 to prevent body fluids from passing into the device 12e. A set screw 52 tightens against the pin 48 to secure the pin within the socket.

Within the enclosure 20 are the electronic components 54a, 54b that govern operation of the device 12e. For example, in the FIG. 3A embodiment, components 54a are associated with delivery of a defibrillation pulse via lead 14, whereas components 54b are associated with the sensing function performed using sensing electrodes on the defibrillation lead or on a separate lead (not shown). Isolating components 54a from components 54b may be desirable if noise generated by the high voltage defibrillation circuitry 54a during charging might interfere with performance of the sensing circuitry 54b.

Device 12e further includes one or more batteries 56 for supplying power to the device, and one or more capacitors 58 for storing an electrical charge and for delivering stored charge to the defibrillation lead(s) 14e and/or exposed electrode 60 on the enclosure 20. A circuit interconnect 62 provides the electrical coupling between the electronic components 36a, 36b, lead 14e, electrode 60, batteries 56 and capacitors 58. Contacts 64 couple these components to the interconnect 62.

As shown in FIG. 3A, the components of device 12e may be arranged in series with one another to give the device 12e a streamlined profile. Because the device 12e is intended for implantation within the patient's vasculature, some flexibility may be desired so as to allow the elongate device to be easily passed through the vasculature. Flexibility may be added by segmenting the device, such as by forming one or more breaks 66 in the enclosure 20, and by forming one or more articulations 68 at each break 23 by connecting the segments using silicone rubber filler. The articulations 68 thus form living hinges, which bend in response to passage of the device 12e though curved regions of the vasculature. It should be noted that in this embodiment it is desirable to form interconnect 62 as a flex circuit so that it will not prevent bending at the articulations.

As discussed previously, the proximal portion of the device 12e may include a connector 25 for receiving the distal end of positioning mandrel 18 (FIG. 2A), which may optionally be used to push the device 12e through the patient's vasculature as described below. The connector 25 may take the form of a threaded bore for receiving a threaded screw member at the distal end of the mandrel 18, or it may have any other type of configuration for detachably engaging the distal end of the mandrel.

Figure 3B:
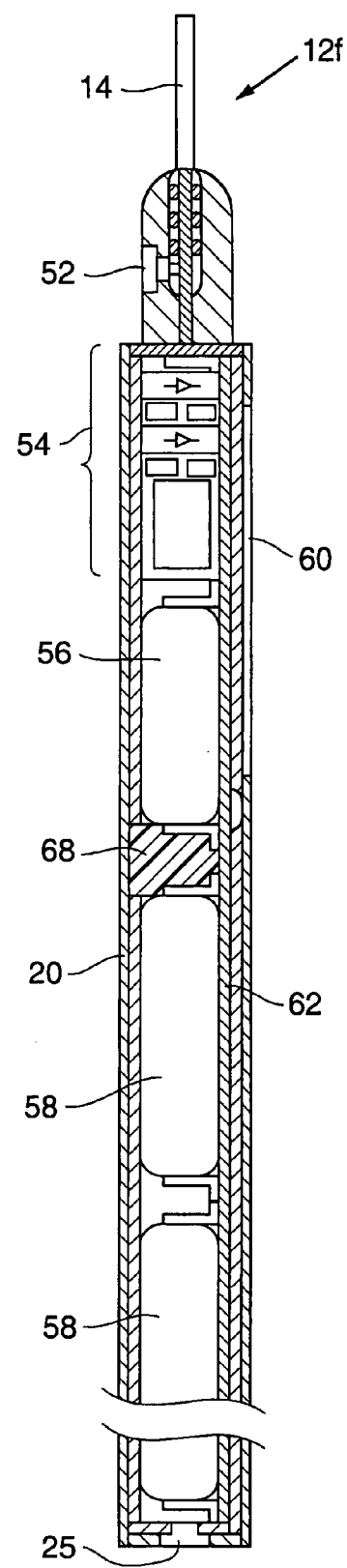
FIG. 3B is a plan view similar to FIG. 3A showing a second embodiment of an intravascular electrophysiological device of a type which may be used with the system shown in FIGS. 2A-2F.

A second example of an arrangement of components for the intravascular electrophysiological device is shown in the device identified by reference numeral 12f in FIG. 3B. Many of the components are the same as those shown in the FIG. 3A embodiment and will not be discussed again in connection with FIG. 3B. This second embodiment differs from the first embodiment primarily in that the electronic components 54 are included within a single area of the enclosure 20. This configuration may be used, for example, when the device is intended only for performing pacing functions (and thus lacks the relatively noisy charging circuitry found in the defibrillation circuitry), or if isolation of the type shown in the FIG. 3A embodiment is not necessary to prevent noise from the charging circuit from interfering with the sensing circuits.

Figure 3C:
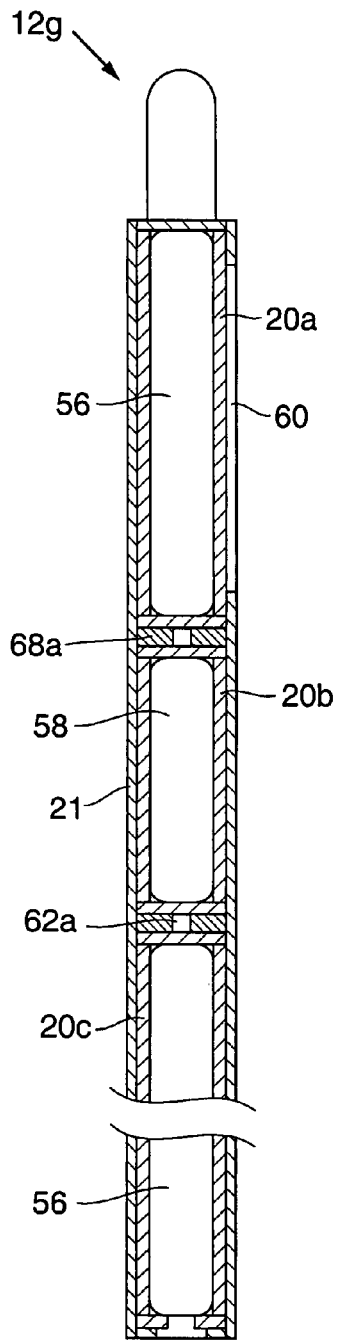
FIG. 3C is a plan view showing a third embodiment of an intravascular electrophysiological device of a type which may be used with the system shown in FIGS. 2A-2F.
Figure 3D:
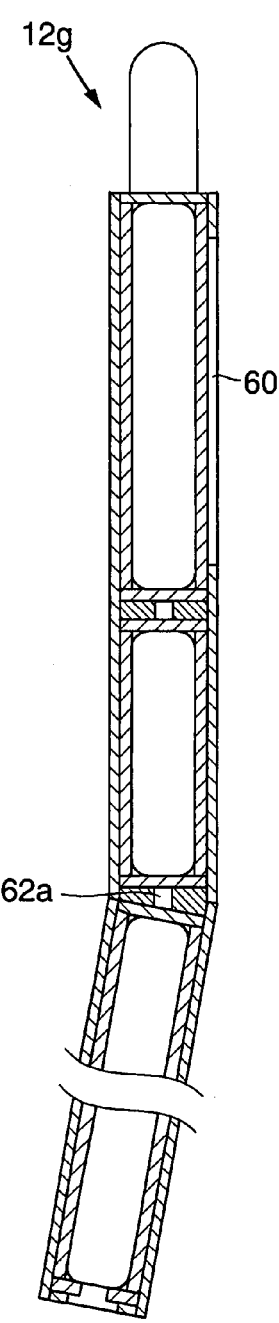
FIG. 3D is a plan view similar to FIG. 3C illustrating bending of the device.

One variation on the FIGS. 3A and 3B embodiments is the device 12g shown in FIGS. 3C and 3D. In device 12g, each segment may be separately enclosed by its own enclosure 20a, 20b, 20c or partial enclosure formed of titanium or other suitable material. The components within the enclosures 20a, 20b, and 20c are electrically connected by flex circuits 62a, and the enclosures are connected using a flexible material such as silicone rubber filler to form articulations 68a. FIG. 3D illustrates bending of the device 12g at one of the articulations. Many of these enclosures may be "strung together" to form the device body. This configuration is particularly desirable for embodiments incorporating particularly long device bodies, such as the devices of the FIGS. 2A and 2B embodiments. For these embodiments, which may have device bodies of approximately 10-60 cm in length with individual segments ranging from approximately 2-28 cm in length, flexibility of the device may be essential for movement and positioning of the device within the vasculature with minimal damage to the blood vessels.

Figure 3E:
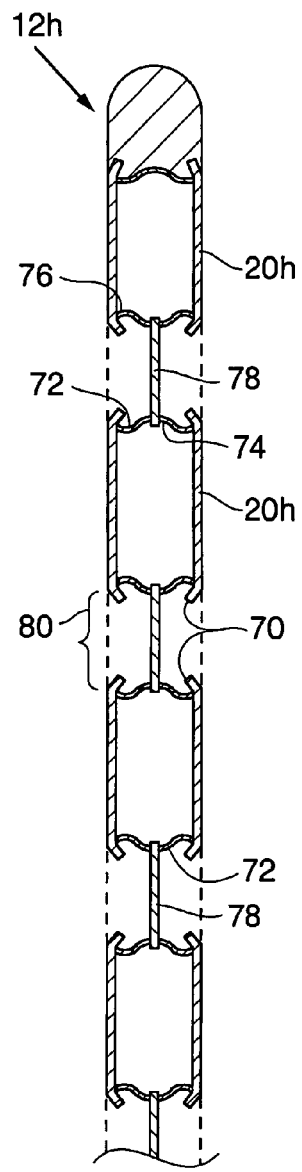
FIG. 3E a plan view showing the mechanical features of a fourth embodiment of an intravascular electrophysiological device of a type which may be used with the system shown in FIGS. 2A-2F.

FIG. 3E illustrates an alternative mechanical assembly of individual segments to form a device 12h. The mechanical components used to connect the segments are optimally designed such that axial, flexural and torsional forces imparted to the device 12h are transmitted by the mechanical components rather than by the electrical conductors that extend between the segments and the associated pins and feed-through components that collectively provide electrical coupling between the components in the device's segments.

The drawing shows the device 12h in partially-constructed form and without the electrical and electronic components, so that the mechanical elements can more easily be seen. Each segment comprises a tubular enclosure 20h, which may take the form of a hollow tube having open ends 70 as shown. Enclosures 20h may vary between 2 mm and 13 cm in length, depending on the nature of the elements to be housed within the enclosures. Collectively, a device 12h may range in length from 10-60 cm, and in most instances between 25-55 cm.

Couplers 72 are secured (e.g. by welding or similar techniques) within the enclosures 20h, near the ends 70. Hinge regions 80 lie between the enclosures 20h and are filled with elastomer to seal the enclosures against body fluids.

FIG. 4A shows the couplers 72 separate from the tubular enclosures. Each coupler 72 includes a central bridge 74 and may include radial spokes 76 or an alternative structure that leaves open spaces for passage of conductors around the coupler as described in greater detail with respect to FIG. 5E. One or more stiffening rods 78 are joined to the coupler 72. Each such rod 78 extends between two couplers 72 as shown in FIG. 4A to form a mechanical assembly that mechanically links a pair of adjacent enclosures 20h as shown in FIGS. 3E and 4B. In the embodiment shown, rod 78 is coupled to the central bridge 74 of the coupler 72 and is secured in place using welding techniques or alternative methods.

The rod and coupler materials may be selected from materials that will transmit axial, flexural and torsional forces imparted to the device 12h, but that will allow flexion of the device at hinge regions 80. The rod 78 may thus be formed of a solid core wire, tubing, coil, or mesh braid of materials such as titanium, nitinol, stainless steel, or polymers such as nylon or polyurethane. Exemplary materials for the coupler 72 include titanium, nitinol, stainless steel, polymers, and Kevlar. Forming all or a portion coupler 72 of a flexible material or a spring-like material may also provide the needed flexibility. Alternatively, the coupler 72 may be fairly rigid and the rod 78 may be somewhat flexible. As another alternative, both the coupler 72 and the rod 78 may have some flexibility. It should be mentioned at this point that the coupler/rod assembly are but one example of assemblies that may be used for mechanically linking the enclosures 20h.

FIGS. 5A through 5E illustrate one example of a sequence of steps that may be used for assembling components into the segments 20h and for electrically coupling components between segments 20h of FIG. 3E.

Figure 5A:
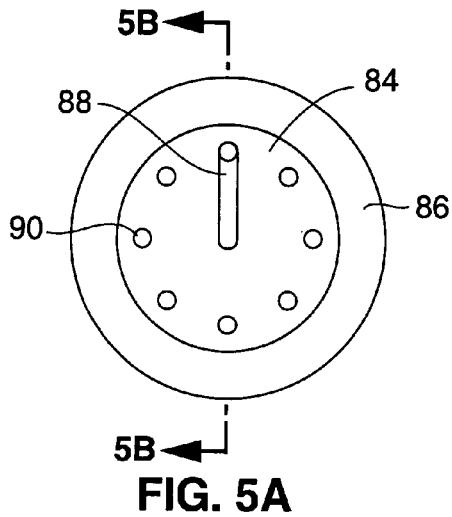
FIGS. 5A-5E are a sequence of figures illustrating formation of the electrical and mechanical connections within a device enclosure of the type shown in FIG. 3E.
Figure 5B:
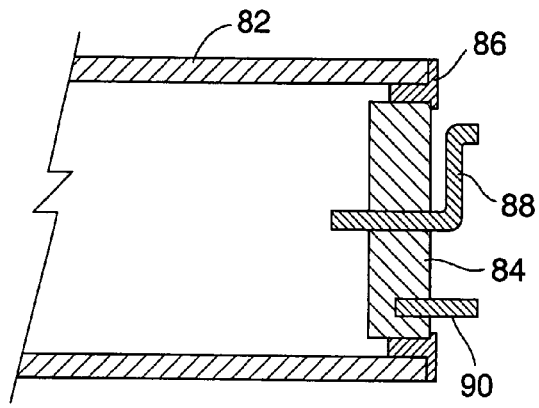
Figure 5C:
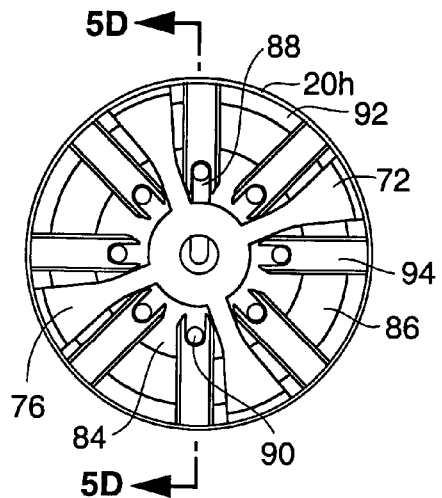

FIG. 5B shows a component 82 that is to be housed within a segment 20h (FIG. 3E) of the device 12h. Components 82 will include batteries, capacitors, circuitry, electronics, etc. The components may have the cylindrical shape as shown, or any other shape that can be inserted into the enclosure 20h. Component 82 is fitted with a cap 84 formed of ceramic or other insulative material. Cap 84 may include ring 86 that seats against the component 82 as shown. A connector pin 88 extends through a bore hole in the cap 84 and is electrically coupled to the component 82. One or more conductive pins 90 (seven are shown) are isolated within blind holes in the cap 84. Cap 84 and pins 88, 90 may be integral with the component 82, or they may be a separate component that is positioned in contact with the component 82 such that pin 88 is in registration with a corresponding contact on the component. The connector pin 88 may be angular as shown such that its free end is within the circumferential arrangement of the other pins 90 as best shown in FIG. 5A.

Figure 5D:
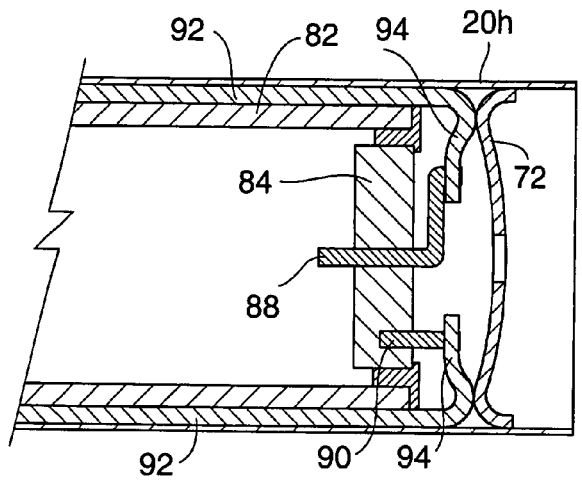

Referring to FIG. 5D, the component 82/cap 84 assembly of FIG. 5B is positioned within the segment enclosure 20h, with a flex circuit 92 wrapped at least partially around the component 82 as shown. Other conductive elements may be used in place of the flex circuit, including an array of conductors embedded in polymer and molded into a sheet or extruded into a tube.

Figure 5E:
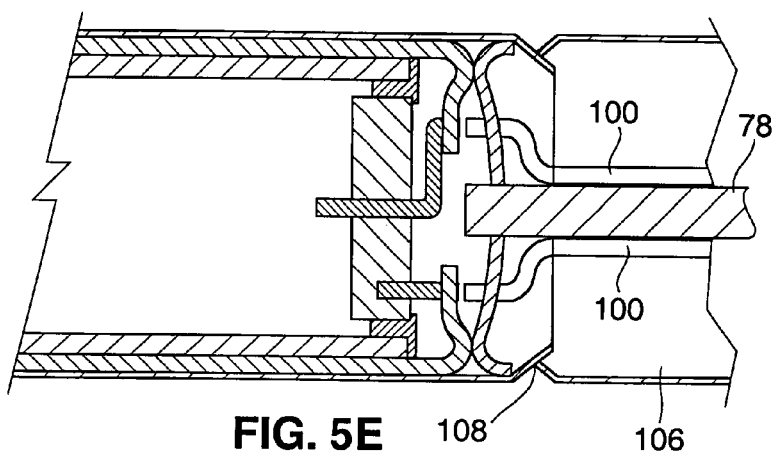

Flex circuit 92 includes conductor tabs 94 folded over into contact with the pins 88, 90 as shown. After the tabs 94 are positioned in contact with the pins 88, 90, coupler 72 (also shown separately in FIG. 4A) is introduced into the enclosure 20h and is secured in place using, for example, welding or a mechanical interlock. Although the rod 78 (also shown separately in FIG. 4A) is not shown in FIGS. 5C and 5D, the rod 78 may be integral with coupler or it may be pre-connected (by welding or mechanical connection) to the coupler before or after the coupler 72 is placed in the enclosure 20h. FIG. 5E shows the assembly with the rod 78 in place. Referring again to FIG. 4B, the rod 78 extends between adjacent segment enclosures 20h, each of which is assembled as described above.

Referring to FIG. 6A, a conductor assembly 98 completes the electrical connection between the segments 20h. The conductor assembly may comprise wires 100 arranged in a configuration (such as the illustrated helical configuration) that will prevent damage to or disconnection of the conductors when the device flexes at the hinge regions 80. As another alternative, the conductor assembly may be comprised of wires 102 extending through a flexible insulated ribbon 104 positioned around the rod 78 as shown in FIG. 7. In other embodiments, flexibility may be added to the conductor assembly by incorporating loops, coils, or sinusoidal bends into the wires to allow slight elongation of the net length of the wires when the device 12h is flexed.

Referring again to FIG. 5E, the ends of the wires 100 are coupled to corresponding ones of the pins 88, 90. This connection may be made by various methods, including soldering or employment of a mechanical jack-type connector (not shown) with corresponding mating components on the wires 100 and conductors 88, 90. Once electrical coupling is achieved between wires 100 and conductors 88, 90, the gap 80 (FIGS. 4B and 6A) between neighboring enclosures 20h is filled with an elastomeric material such as silicone, polyurethane, perfluoroethers, or epoxies to create a sealed barrier 106 (FIG. 5E). The barrier 106 prevents body fluids from entering the enclosures 20h. Application of the barrier 106 may be preceded by application of a paralene pre-coating or other redundant barrier to the conductors and other components within and extending between the enclosures 20h.

The elastomeric barrier material preferably fills the ends of the enclosures 20h as well as the space between the enclosures. As shown in FIG. 5E, the ends 108 of the enclosure 20h may be swaged into the elastomeric barrier 106 to facilitate retention of the barrier 106, to improve sealing, and to minimize the chance for delamination of the elastomeric material. It may also be desirable to roughen the interior surface of the enclosure 20h, or to form holes around the end circumference of the enclosure 20h to create a mechanical or interference fit between the enclosure and the elastomer.

The method described in connection with FIGS. 5A through 7 is but one example of the many methods available for connecting the enclosures 20h.

Figures 8A, 8B:
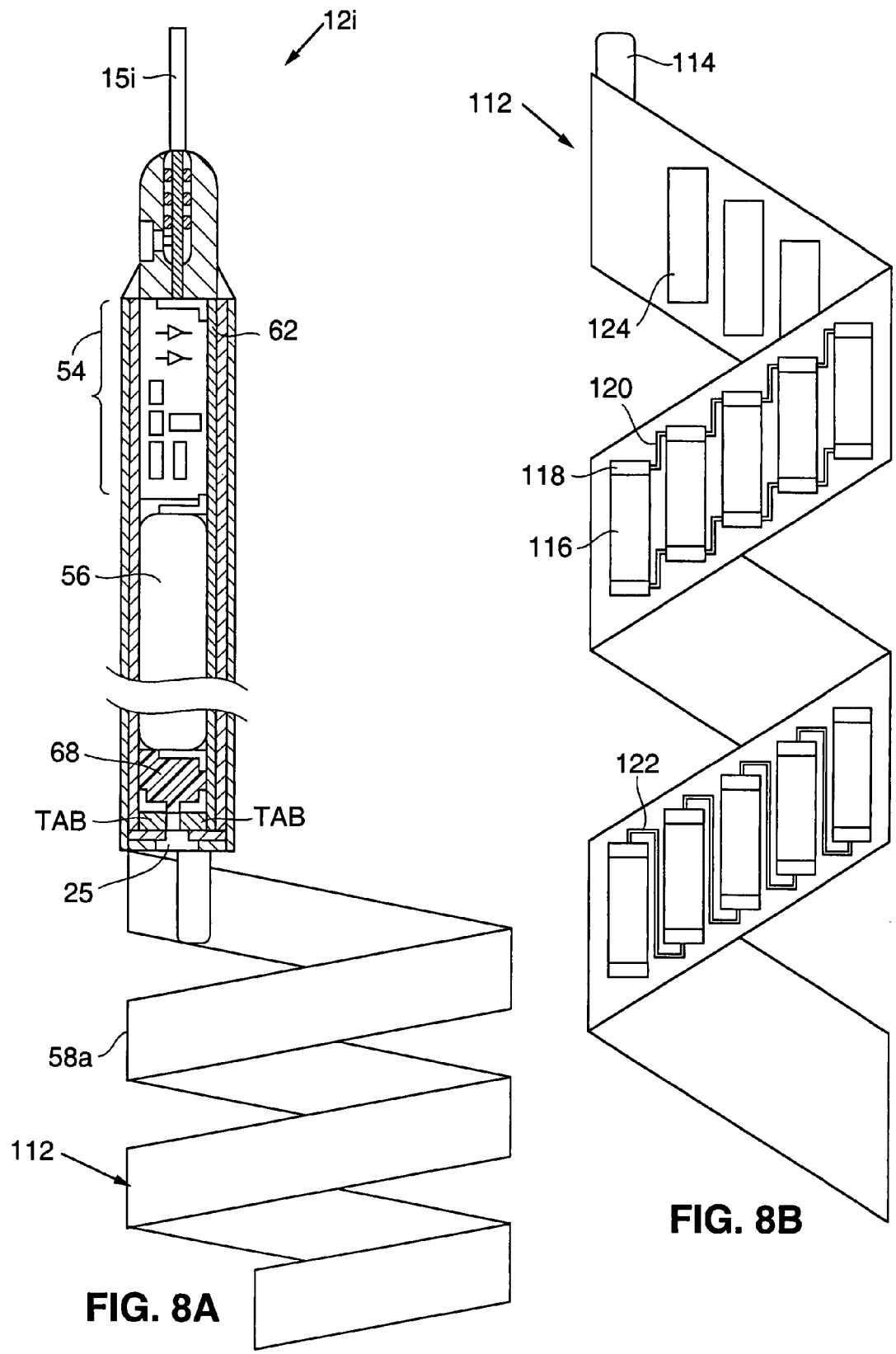
FIG. 8A is a plan view showing a fifth embodiment of an intravascular electrophysiological device of a type that may be used with the systems shown in FIGS. 2A-2F.
FIG. 8B is a plan view showing the ribbon portion of the fifth embodiment.

Another arrangement of device components is found in the intravascular device identified by reference numeral 12i and shown in FIG. 8A. Many of the components are the same as those shown in the FIGS. 3A and 3B embodiments and will not be discussed again. The FIG. 8A embodiment differs from the prior embodiments largely in the configuration of the capacitor 58a, which takes the form of a coiled ribbon 112 mechanically coupled to the proximal end of the device 12i (or to a more distal location) and electrically coupled to the circuit interconnect 62. The coiled ribbon may take the form of a flex circuit of the type described in connection with FIG. 5B below, or it may be formed of layers of capacitor material overlaying one another to form the ribbon itself.

Prior to implantation, the ribbon 112 is compressible to a streamlined condition for introduction into the body. For example, it may be placed within a delivery sheath or it may be retained in a streamlined position by winding the ribbon against the mandrel and retaining it with a shorter sleeve, suture or wire etc. As yet another example, proximal tension may be imparted on the ribbon by pulling the ribbon in the longitudinal direction, thereby elongating the ribbon while reducing its overall width, much like pulling on a coiled telephone wire. Once positioned within the vessel at the appropriate site for implantation, the capacitor is released from the compressed position and springs to an expanded position within the vessel, as further discussed in the section entitled "System Implantation" below.

Although the ribbon is described as being a capacitor, it should be appreciated that a different subset of the device components may be provided in the form of a ribbon-like structure or circuit. For example, the capacitor may be similar to the capacitors 58 shown in FIGS. 3A and 3B, and the device's battery may instead be formed in the coiled ribbon configuration. In yet another variation, the coiled ribbon may instead be an antenna for transmitting signals alerting a physician to the occurrence of an arrhythmia, and both the capacitor and battery may take the forms shown in FIGS. 3A and 3B, or some alternate form.

FIG. 8B is an enlarged view of the ribbon 112 used for capacitor 58a of FIG. 8A. The ribbon 112 is a coiled flex circuit electrically connected to the rest of the device 12i by tab 114. Discrete capacitor segments 116 are preferably arranged in a stepped pattern on the ribbon surface and may be applied using spray-on/lithographic techniques or other means. Segments 116 have terminals 118 that may be connected in parallel using parallel connections 120, or in series using series connections 122 as needed. The segments 116 may be on the exterior surface of the ribbon 112, and/or there may be additional segments or related components 124 (including integrated circuit components, passive circuitry components, microprocessor components etc.) on the interior surface of the coil.

It should also be noted that the entire device (including the capacitors, batteries, microprocessor, electronics, etc) may take the form of a coiled ribbon flex circuit, with the components being located on the exterior or interior surface of the ribbon and with the leads coupled to the ribbon.

Any one of the devices described herein is preferably able to communicate via wireless telemetry to an instrument outside of the patient's body. This is commonly referred to as device interrogation and/or programming and allows the physician to monitor the state and performance of the device. It also allows the physician to reconfigure the device in the case of programmable settings.

The circuitry used for device interrogation and/or programming can be included in any of the device embodiments, with the device telemetry antenna either encapsulated within the device enclosure(s) or as part of a ribbon component set of the type shown in FIG. 8A. The circuitry may include a circuit that will respond in the presence of a magnetic field, which is a feature also known in the implantable device industry. These types of communication means are intended to allow the device to communicate the device's status to the physician. For example, the status information may include the state of the battery system, and whether or not a therapeutic energy delivery had occurred or not. The communication might also identify the parameters the device used, including a stored electrogram, to allow reconstruction of the delivery episode by the instrument. The telemetry feature may also be used to program certain features governing function of the device, such as the threshold heart rate in beats per minute which, when detected by the device, will cause the device to provide appropriate energy therapy.

Retention Devices

The intravascular system further includes a mechanism for retaining the device in the patient's vasculature, such as in the superior vena cava 3a, inferior vena cava 3b, or the left or right subclavian 2a, 2b (see FIG. 1). Although various means may be used to retain the device within the vasculature, one example of a retention device is the tubular retention sleeve or anchor 16d of the type illustrated with device 12d in FIG. 2F and as shown in greater detail in FIGS. 9A and 9B. The retention device is described as a separate component from the device 12d, but it will be appreciated that the anchor 16d or other retention device may be integral with the device 12d.

The anchor 16d may include features that give some structural stability to cause the anchor to radially support the device against a vessel wall. For example, a mesh, band or other framework 126 (FIG. 9B) formed of shape memory (e.g. nickel titanium alloy, nitinol or shape memory polymer) elements or stainless steel, Eligoy, or MP35N wires or structures may be used. The anchor 16d is preferably provided with a smooth polymeric barrier 128 that is both anti-proliferative and anti-thrombogenic and that thereby prevents endothelial growth and thrombus formation on the anchor. Examples of materials for the polymeric barrier include, but are not limited to ePTFE, or other fluoropolymers, silicone, non-woven nylon, or biomimetic materials.

Layers of barrier material on the interior and exterior surfaces of the framework preferably form the polymeric barrier 128, although it will be appreciated that the framework 126 and barrier 128 may be combined in a variety of ways to prevent thrombus formation and endothelialization on the anchor walls. As one alternative (or in addition to the polymeric barrier), the anchor material could include surfaces for eluting non-coagulative, anti-platlet (e.g. IIBIIIA glycoprotein receptor blockers), anti-proliferative, and/or anti-inflammatory substances.

Figure 9A:
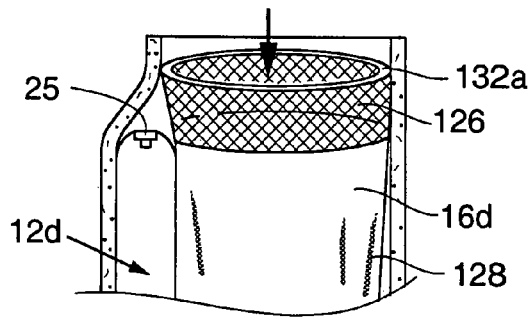
FIG. 9A is a perspective view schematically illustrating use of an anchor to anchor an intravascular electrophysiological device within a vessel.

The framework 126 may extend through the entire length of the anchor, or it may be included in only a portion of the anchor, such as at the proximal and distal end regions as shown in FIG. 9A, leaving the intermediate region 130 between them with no structural reinforcement. This arrangement may be preferable in that is allows the intermediate region to conform to the surface of the device 12d during use. As another alternative, the intermediate region may include some structural reinforcement, but less than is provided in the more rigid proximal and distal regions 126 so as to allow some conformability of the anchor to the device surface.

During implantation, the anchor 16d is compressed to a streamlined positioned for passage through the vasculature. The anchor 16d may be inserted into a positioning sheath to facilitate movement through the vasculature.

Typically the anchor will be deployed after the device has been positioned at a desired location within the vessel, although if the anchor and device are integral components they will be implanted simultaneously. The anchor is advanced to a position adjacent the device, released from the sheath (if used) and expanded to a radially expanded position as shown in FIG. 9A. The anchor may self-expand and/or it may be expanded using an inflation tool such as a balloon passed into the anchor's central lumen and subsequently inflated. When the anchor is expanded, its radial force engages the device 12d and secure the device 12d against the vessel wall. As shown, the force of the anchor against the device may cause the vessel to distend outwardly due to the vessel's compliance. Blood flowing through the vessel passes through the tubular interior of the anchor as indicated by arrows in FIG. 9A. Because the device 12d occupies the distension in the vessel, the presence of the device causes minimal (if any) obstruction to blood flowing through the vessel.

It is desirable to minimize passage of blood between the anchor 16d and the device 12d so as to minimize the chance of thrombus formation and endothelialization around the device 12d. For this reason, the rims 132a, 132b surrounding the anchor's proximal and distal openings are preferably designed to make sealing contact against the surrounding vessel tissue (and against the lead 15d) as shown in FIG. 9A so as to direct all blood flow into the interior of the anchor. For example, rims 132a, 132b may be formed of a thicker and more pliable material such as silicone or polyurethane-siloxane, or the rims may be supplemented with compliant members that seal against the lead and surrounding tissue. As another example, a swellable hydrogel which expands when placed in contact with fluids including blood, may be included on the anchor's ends to optimize sealing. Ideally, these barriers will form a seal with the adjacent tissue, however it is sufficient that the barriers prevent a substantial amount of blood from passing between the exterior of the anchor and the device, without necessarily forming an impermeable seal.

As will be described below, additional anchoring devices such as anchor 16e (FIG. 2F) similar to the anchor 16d may also be used to anchor leads within the vasculature.

Figure 9C:
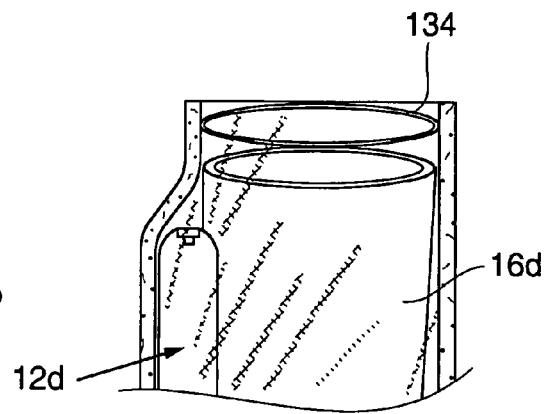
FIG. 9C is a perspective view similar to FIG. 9A but further illustrating use of a liner within the vessel.
Figure 9B:
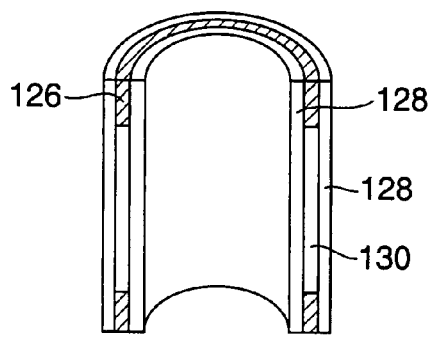
FIG. 9B is cross-sectional perspective view showing a portion of the anchor of FIG. 9A.

As discussed, it is desirable to minimize endothelial growth onto the anchor, since endothelial growth onto the anchor 16d can make it difficult to separate the anchor and device 12d from the vessel tissue during explantation. Referring to FIG. 9C, a tubular liner 134 may be deployed within the vessel prior to implantation of the device 12d and anchor 16d. Liner 134 may be similar in design to the anchor 16d, but is preferably longer than either the device 12d or anchor 16d so that the liner contacts the vessel wall but the device and anchor 16d do not. If used with the FIG. 8A embodiment of the device 12i, which includes coiled ribbon 112, the liner 134 is preferably longer than the combined length of the device enclosure and coil 112. The liner 134 helps to reduce the risk of trauma to the vessel tissue during explantation of the device and/or anchor 16d.

During implantation, the liner 134 is deployed in the desired anatomic location before the device is moved into place. The steps for deploying the liner 134 may be similar to those described above for deploying the anchor 16d. Once the liner 134 is in place, the device is deployed, followed by the anchor 16d, in the same manner as described elsewhere. Over time the liner may become endothelialized, particularly at its edges. However, the endothelial growth is self-limiting to the edge or rim of the liner due to increasing distance from a sustaining blood supply and should not reach the inner retaining anchor 16d. Thus, when it is necessary to explant the device 12d for servicing (such as to replace a battery for example) the inner anchor 16d may be grabbed by a surgical instrument with the outer liner 134 acting as a protective layer for the vessel. The liner 134 may be left in place following removal of the anchor 16d and device 12d. If the device 12d (or a replacement) is to be later re-implanted, it may be returned to its original location within the liner 134.

In an alternative implantation method using the liner 134, the device 12d may be "sandwiched" between the liner 134 and anchor 16d before implantation by placing the device inside the liner, then placing the anchor in a compressed position within the liner, and then expanding the anchor to engage the device between the sleeve and anchor. The three components are then compressed into a positioning sheath and introduced as described elsewhere.

Figure 10A:
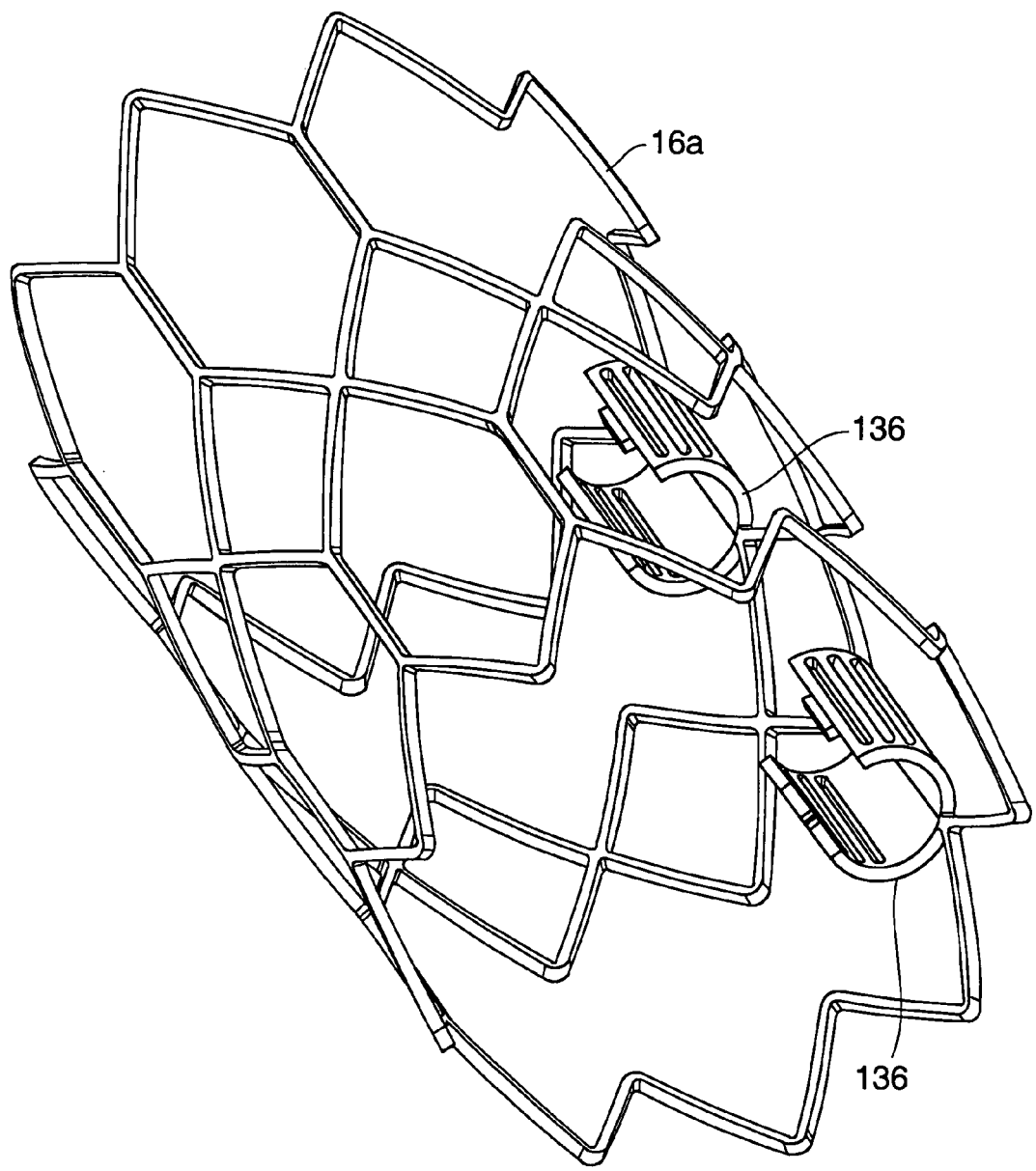
FIG. 10A is a perspective view of an anchor suitable for use with the systems of FIGS. 2A-2F.

FIGS. 10A though 10E illustrate an alternative anchor 16a of the type shown with the systems of FIGS. 2A through 2C. The anchor 16a is beneficial in that it is implanted integrally with the device, and thus does not require a separate implantation step.

Referring to FIG. 10A, anchor 16a includes structural features that allow the anchor to radially engage a vessel wall. For example, a band, mesh or other framework formed of one or more shape memory (e.g. nickel titanium alloy, nitinol, thermally activated shape-memory material, or shape memory polymer) elements or stainless steel, Elgiloy, or MP35N elements may be used. The anchor may include anti-proliferative and anti-thrombogenic coatings, although in this embodiment the anchor structure 16a is preferably provided to promote tissue ingrowth to as to enhance anchor stability within the vessel. The anchor may also have drug delivery capability via a coating matrix impregnated with one or more pharmaceutical agents.

Figure 10B:
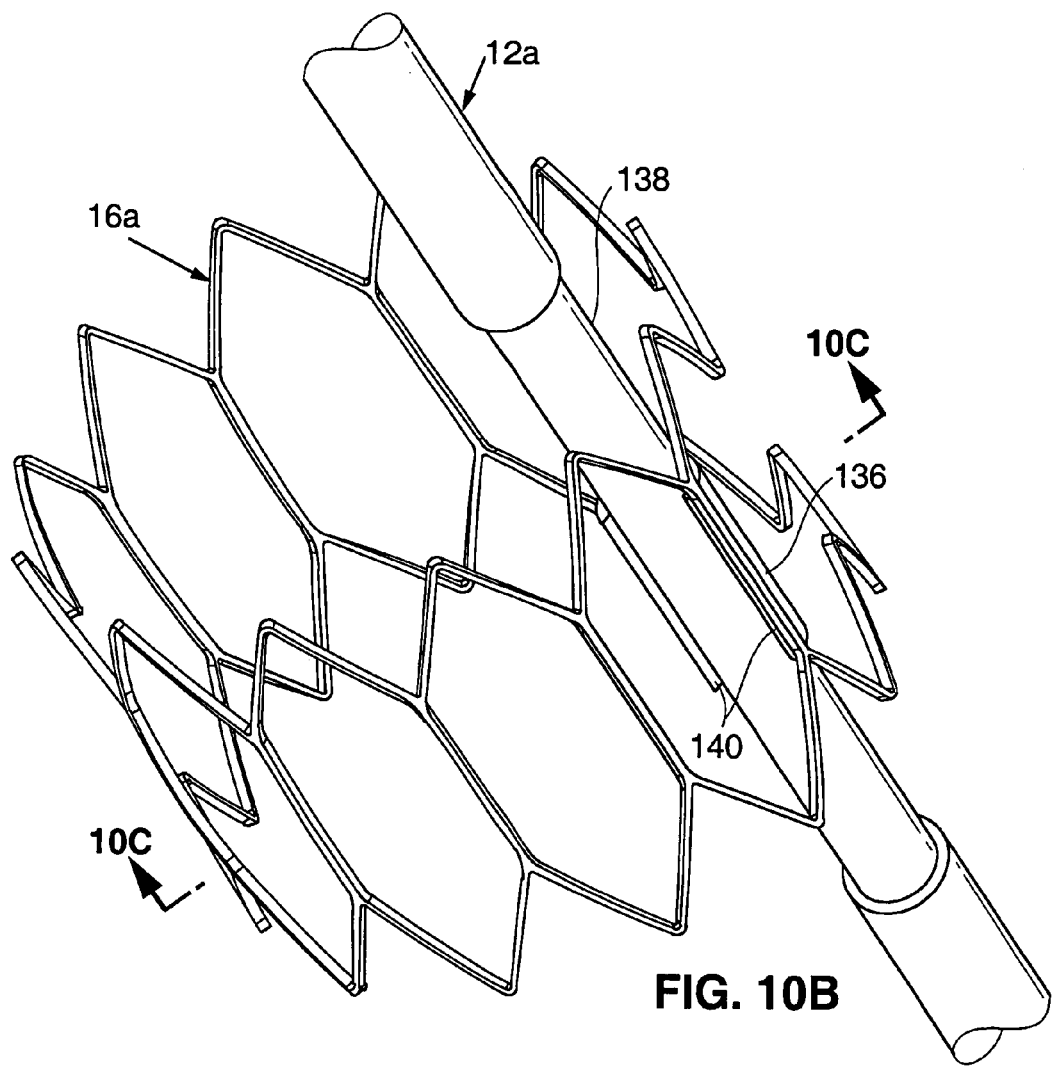
FIG. 10B is a perspective view showing the anchor of FIG. 10A attached to an implantable electrophysiological device and in the expanded position.

FIG. 10B shows one anchor 16a attached to a device 12a, although naturally one, two or more such anchors may alternatively be used. In one embodiment, anchor 16a is attached to the implant 12a by a collar 136, or other suitable connection. The implant 12d may include a recessed portion 138 that allows the exterior of the anchor to sit flush with the exterior of the implant 12a when the anchor is its compressed position. The recessed portion should have smooth contours in order to discourage thrombus formation on the device.

Figure 10C:
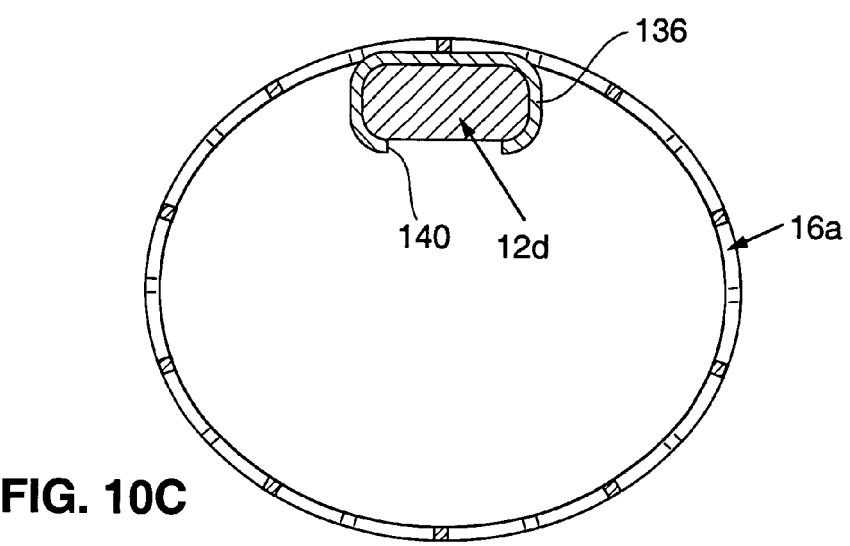
FIG. 10C is a cross-sectional end view of the device shown in FIG. 10B.

The anchor 16a and device 12a may be detachably connected to the recessed portion using methods that allow the anchor 16a and the implant 12a to be separated in situ, for permanent or temporary removal of the implant 12a. A detachable connection between the anchor 16a and implant 12a may utilize a snap fit between the collar 136 and implant 12a. As shown in FIG. 10C, both the collar 16a and the recessed portion 138 of the implant may include an elliptical cross-section. If it becomes necessary to remove the medical implant from the patient's body, the medical implant may be torqued about its longitudinal axis, causing the body of the implant to cam the edges of the collar 136 to a slightly opened position, thereby allowing the implant to be passed between the edges 140 of the collar 136. In an alternative embodiment, a clevis pin-type connection may be made between the anchor 16a and the device 12a. Such a connection would be provided with a remotely actuated mechanism for releasing the clevis pin connection to thus permit separation of the device and the anchor.

The anchor may be configured such that the device 12a and anchor 16a share a longitudinal axis, or such that the axes of device 12a and anchor 16a are longitudinally offset.

Figures 10D, 10E:
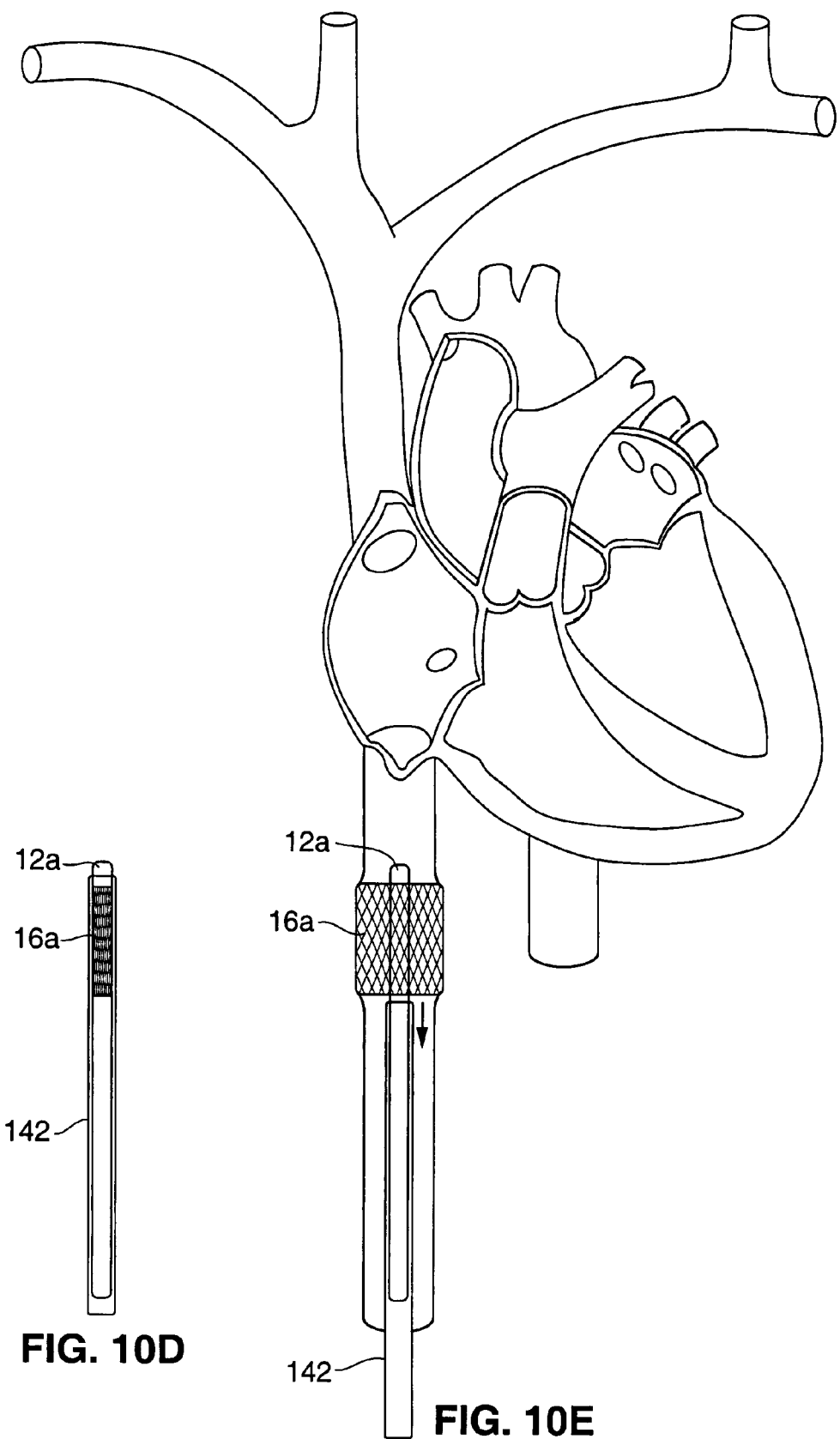
FIG. 10D is a side elevation view of a device showing the anchor of FIG. 10B positioned on a device and compressed by a sheath.
FIG. 10E is similar to FIG. 10D but shows retraction of the sheath to permit expansion of the anchor within a blood vessel.

Referring to FIG. 10D, a retractable sheath 142 may be slidably positioned over the anchor 16a and implant 12a so as to retain the anchor in its compressed position. Retraction of the sheath as indicated in FIG. 10E allows the anchor 16a to expand into contact with the surrounding walls of the vessel, thereby holding the medical implant in the desired location. Once deployed, the anchor 16a is preferably intimate to the vessel wall, which is distended slightly, allowing the vessel lumen to remain approximately continuous despite the presence of the anchor and thus minimizing turbulence or flow obstruction.

Implantation Methods

Several methods for implanting intravascular electrophysiological systems are shown in FIGS. 11A through 15E. These implantation methods are preferably carried out under fluoroscopic visualization. Although the methods described in connection with FIGS. 11A through 15E introduce the device into the venous system via the femoral vein, the device and components may alternatively be introduced into the venous system via that subclavian vein or the brachiocephalic veins, or into the arterial system using access through one of the femoral arteries. Moreover, different components of the intravascular systems may be introduced through different access sites. For example, a device may be separately introduced through the femoral vein and a corresponding lead may be introduced via the subclavian vein.

First Exemplary Method

Figures 11A, 11B:
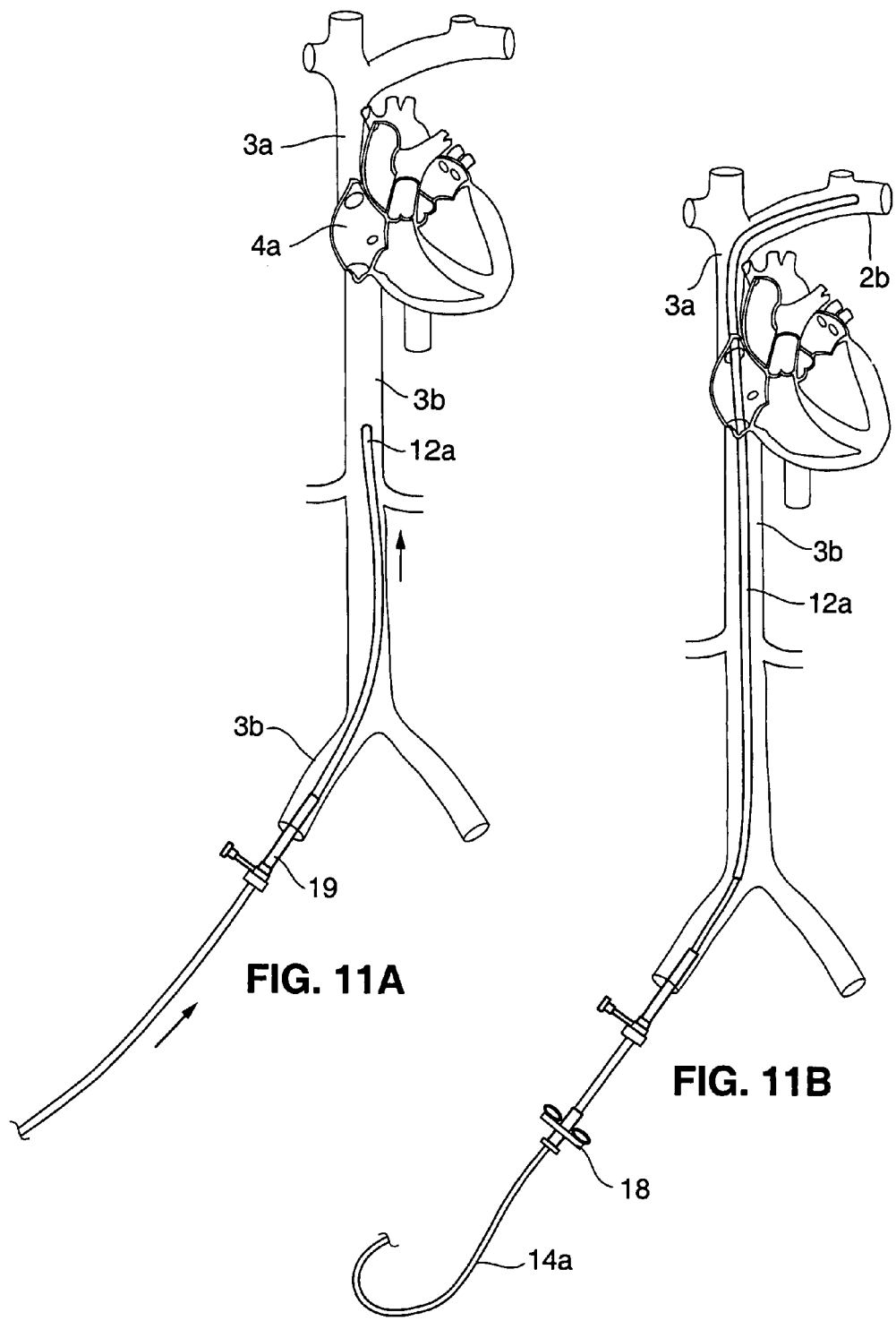

FIGS. 11A through 11F illustrate a method for implanting the system 10a of FIG. 2A. First, a small incision is formed in the femoral vein and the introducer 19 is inserted through the incision into the vein to keep the incision open during the procedure. Next, the device 12a is passed into the introducer 19, and pushed in a superior direction through the inferior vena cava 3b ("IVC"), through the right atrium 4a towards the superior vena cava 3a ("SVC"). With an end of the device 12a still remaining outside the body, mandrel 18 and lead 14a are attached to the exposed end of the device 12a as shown in FIG. 11B. Pressure is applied against the mandrel 18 to advance the device 12a into the left subclavian vein ("LSV") 2b.

Referring to FIG. 11C, once the device 12a is in the target position, the anchor 16a is expanded into contact with the walls of the inferior vena cava 3b. The mandrel 18 is detached from the device 12a and removed from the body.

A steerable guidewire or stylet 144 is attached to the free end 146 of the lead 14a or inserted into a lumen in the lead 14a and is used to carry the free end 146 of the lead through the introducer 19 and into the IVC 3b such that the lead 14a folds over on itself as shown in FIG. 11E. The free end 146 is steered into the right ventricle 7a ("RV") using the stylet 144 and is fixed in place using a helical screw member at the free end 146 or another attachment feature. The stylet 144 is removed, leaving the lead 14a positioned in the right ventricle 7a as shown in FIG. 11F. As an alternative, the free end 146 of lead 14a may be steered into the middle cardiac vein.

Second Exemplary Method

FIGS. 12A through 12E illustrate implantation of the device 12b of FIG. 2B. As with the first exemplary method, this method positions a portion of the device in the left subclavian vein 2b and a lead in the right ventricle 7a (or, alternatively, the middle cardiac vein). However, the method of FIGS. 12A through 12E orients the device 12b of FIG. 2B such that the lead 14b is positioned at the superior end of the device 12b as opposed to the inferior end of the device.

Referring to FIG. 12A, lead 14b is first passed into the introducer 19 and steered into the right ventricle 7a using steerable stylet 144. The lead 14b is then rotated by torquing its free end 150 to fix a helical tip (not shown) on the lead 14b into tissue of the right ventricle as shown in FIG. 12B. A handle 148 may be attached to the free end 150 for this purpose.

Figure 12C:
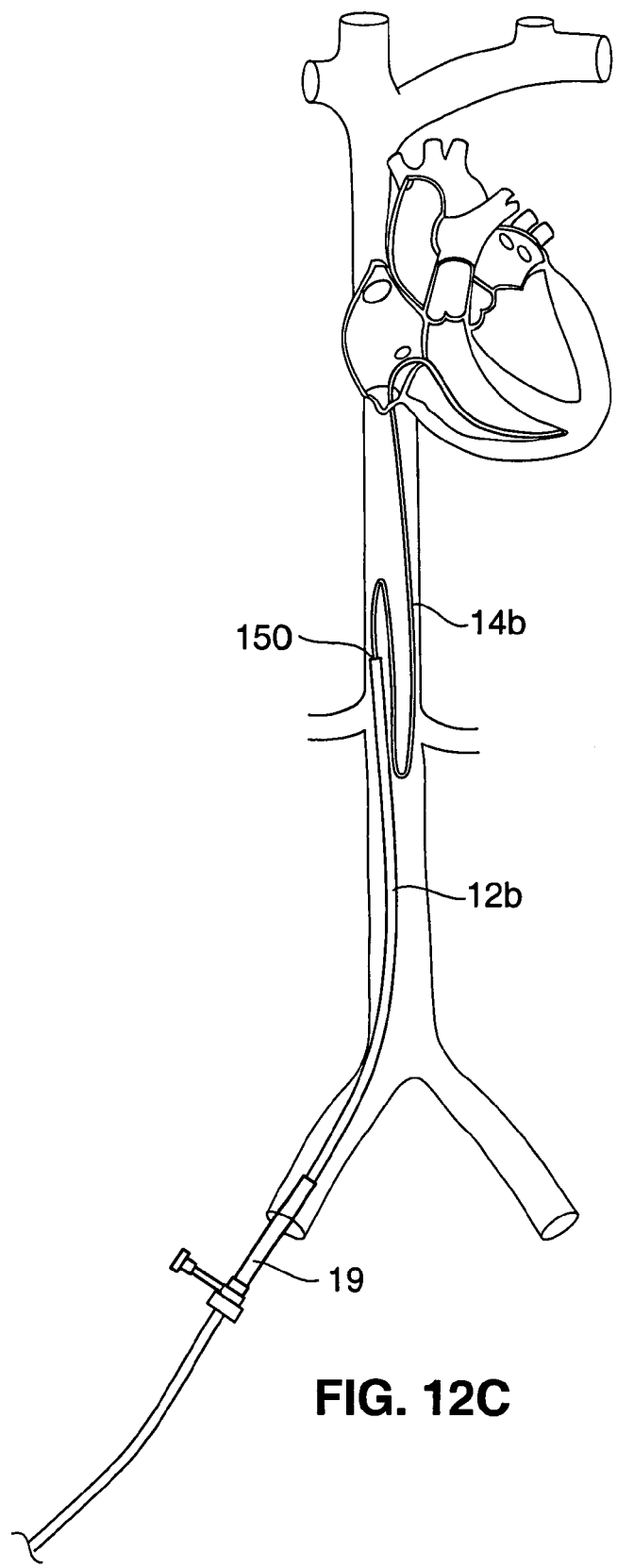

The device 12b is then attached to the free end 150 of lead 14b, which is positioned outside the body. Next, the device is advanced into the vasculature as shown in FIG. 12C. Mandrel 18 is attached to the inferior end of the device 12b and is used to advance the device 12b fully into the vasculature as shown in FIG. 12D. Since the lead 14b will be provided with extra length be ensure that there will be sufficient slack in the lead, some of the lead slack may remain in the IVC 3b. It may thus be necessary to advance the device 12b beyond its target position to drive any slack in the lead 14b beyond the target location. Once the lead has advanced beyond the target anchor location, the mandrel 18 is withdrawn slightly to retract the device 12b into its intended position. The anchor 16a is deployed and the mandrel 18 is removed from the body, leaving the device and lead in place as shown in FIG. 12E.

Third Exemplary Method

Figures 13A, 13B:
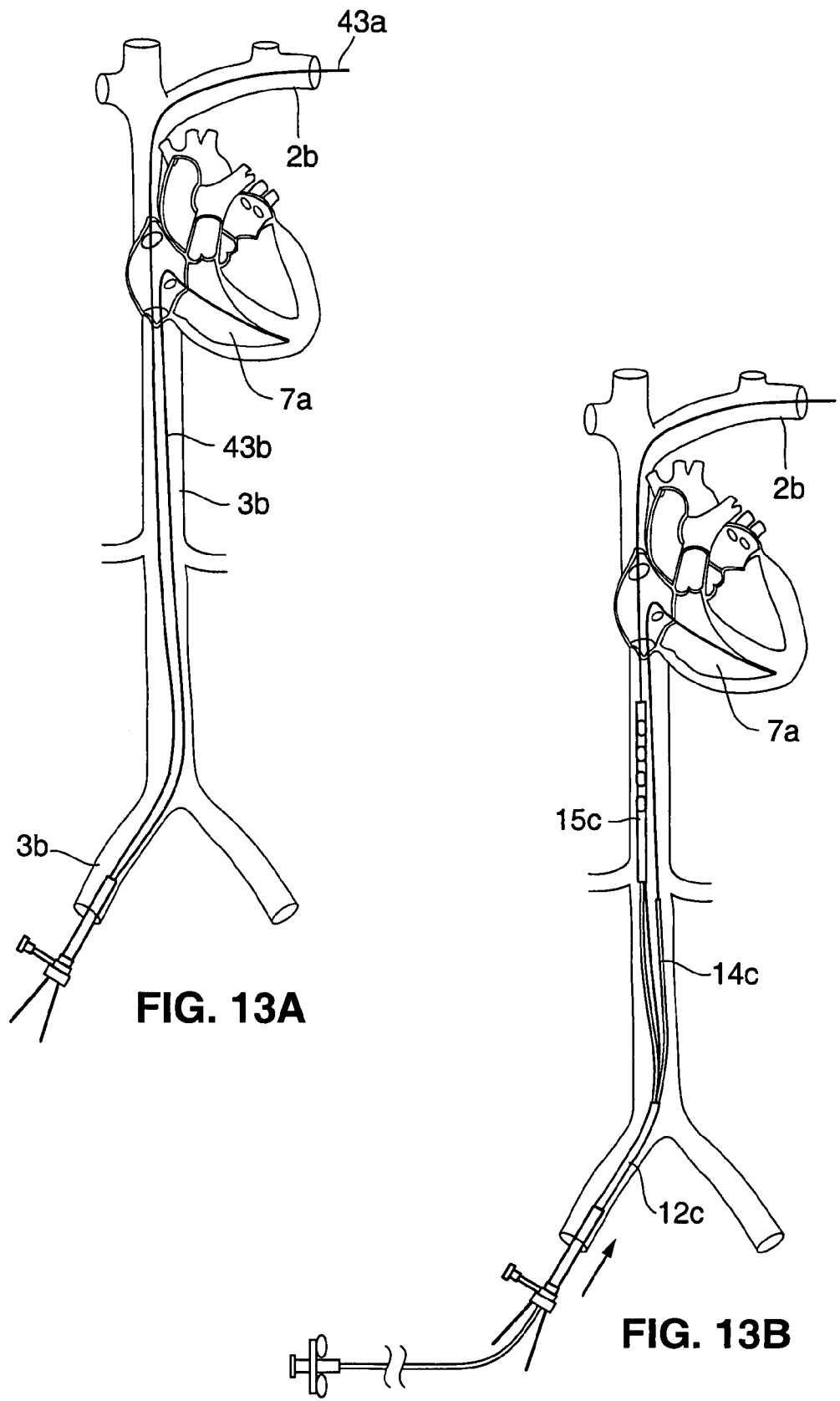
FIGS. 13A-13C are a sequence of drawings schematically illustrating implantation of the system of FIG. 2C.
Figure 13C:
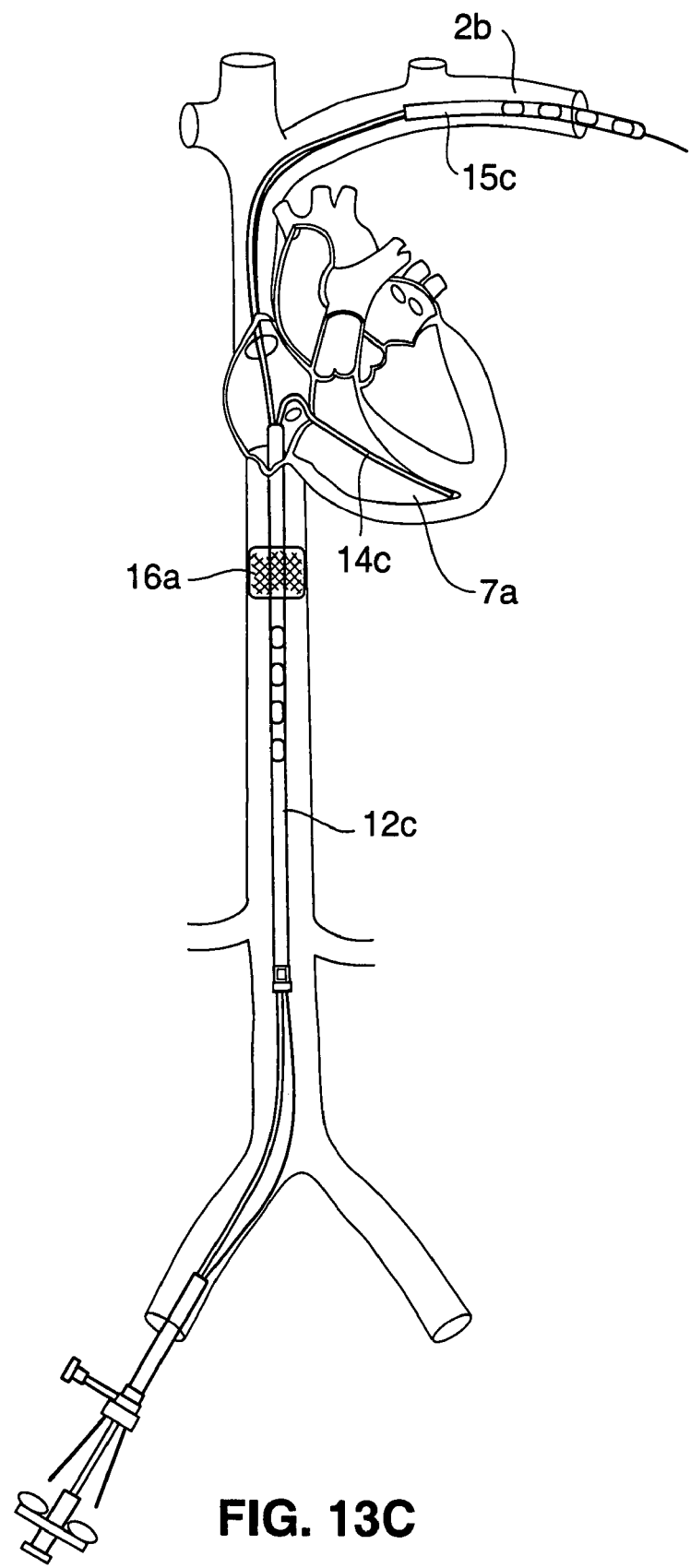

FIGS. 13A through 13C illustrate implantation of the bifurcated system of FIG. 2C. As with prior methods, a small incision is first formed in the femoral vein and the introducer sheath 19 is inserted through the incision into the vein to keep the incision open during the procedure. Next, guidewires 43a, 43b are passed through the sheath 19 and into the inferior vena cava 3b. Guidewire 43a is steered under fluoroscopy into the left subclavian vein 2b and guidewire 43b is guided into the right ventricle 7a of the heart.

Next, as shown in FIG. 13B, the lead 15c is threaded over guidewire 43a and lead 14c is threaded over guidewire 43b. Positioning mandrel 18 is attached to the proximal end of the device 12c. The leads 14c, 15c and then the device 12c are then passed through the sheath 19 and into the IVC 3b. The leads are sufficiently rigid that pushing on the mandrel 18 to advance the device causes advancement of the leads over their respective guidewires. Advancement of the mandrel 18 is continued until the lead 15c is disposed in the desired position within the LSV 2b, and the lead 14c is within the right ventricle 7a as shown in FIG. 13C.

Finally, the device 12c is anchored in place by releasing the anchor 16a to its expanded position as shown in FIG. 13C. The anchor expands into contact with the surrounding vessel wall, thereby preventing migration of the device 12c. If desired, lead 15c may be anchored in the LSV 2b using another suitable anchor. The mandrel 18 is detached from the device 12c, and the mandrel 18 and introducer sheath 19 are withdrawn from the body.

Figure 13D:
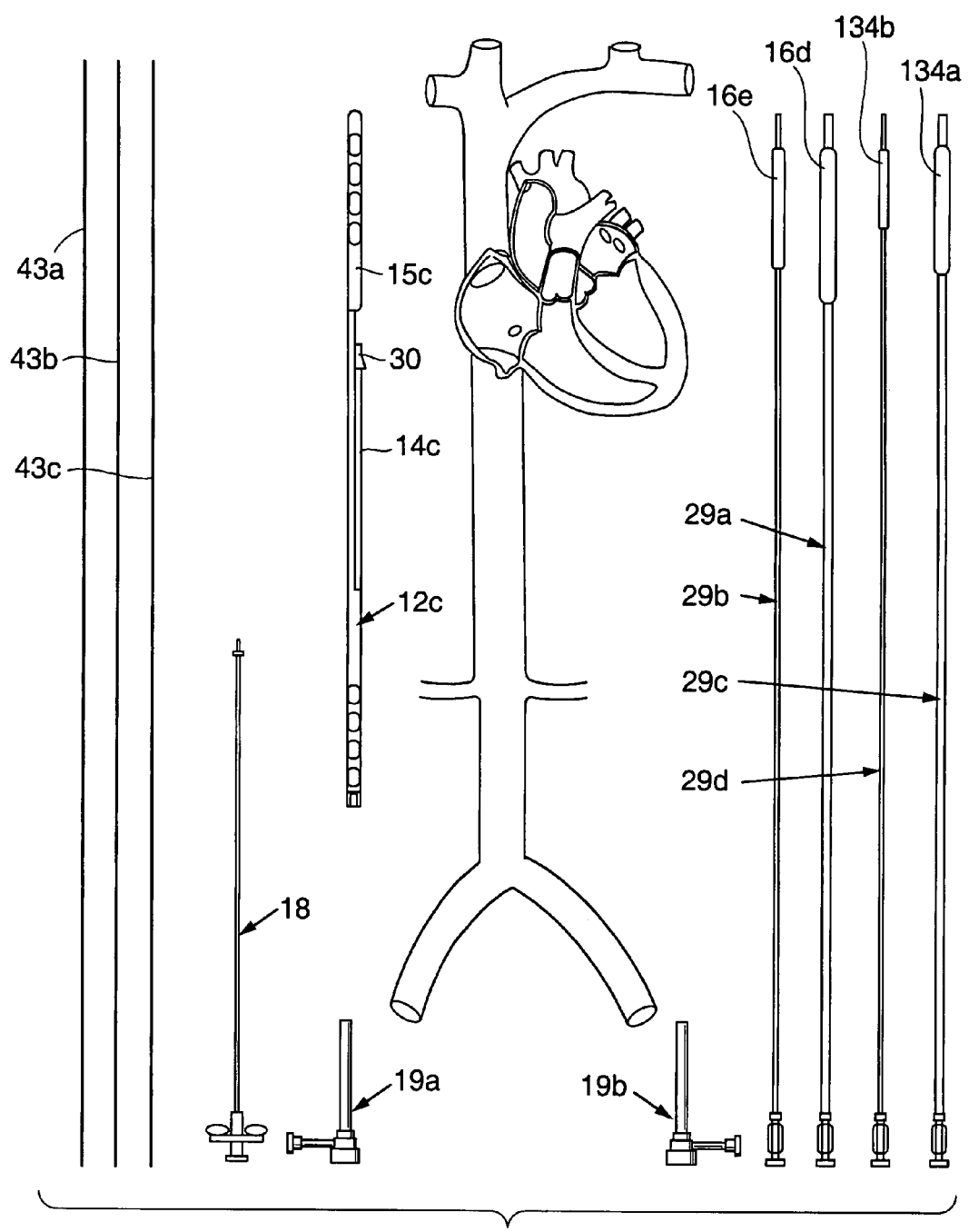
FIGS. 13D-13I show a modification to the implantation method of FIGS. 13A-13C to include steps for implanting separately-implantable retention anchors and liners.

A variation on the third exemplary method uses a system that uses a separately deployable anchor 16d rather than an integrated anchor to retain the device 12d. Referring to FIG. 13D, a delivery catheter 29a is provided for carrying the anchor 16d through the vasculature. A compressive sheath (similar to sheath 142 shown in FIG. 10D) may be used to maintain the retention device 16d in the streamlined or compressed position for implantation and is removable to release the sleeve to the expanded position. If a retention device is also to be used for the LSV lead 15c, a second delivery catheter 29b may be provided for introducing the second retention device 16e.

Optional liners 134a,b are provided for minimizing endothelial growth onto the retention devices by forming a lining between the vessel tissue and the retention sleeves 16d, 16e. As described above in connection with FIG. 9C, each liner may have a design similar to that of the retention devices but it is preferably long enough prevent the implant device, retention device, or lead from contacting the vessel wall. Delivery catheters 29c, 29e are provided for introducing the liners 134a, 134b into the vessels.

Figures 13E, 13F:
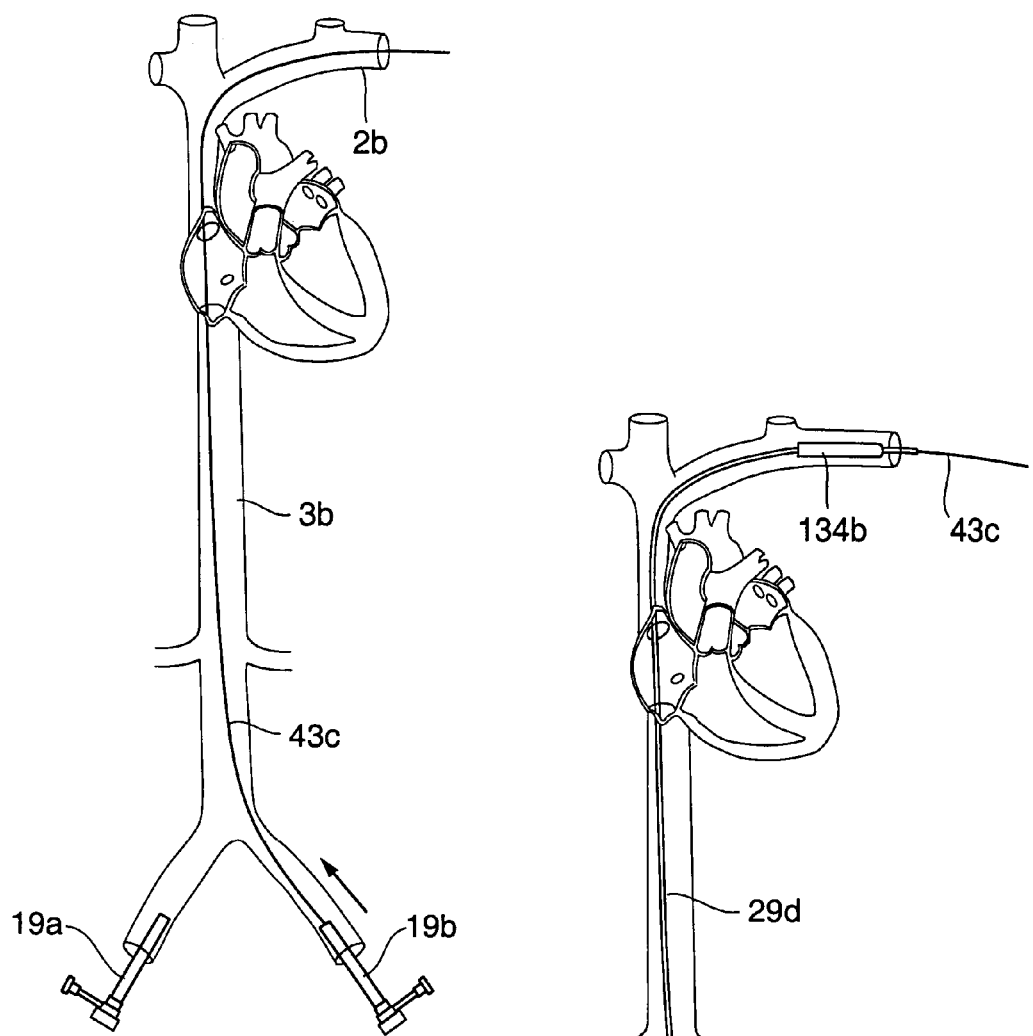

Referring to FIG. 13E, according to this variation, small incisions are formed in each femoral vein and the introducer sheaths 19a, 19b are inserted through the incisions. Next, guidewire 43c is passed through the sheath 19b in the right femoral vein, and into the left subclavian vein 2b. Delivery catheter 29d is passed over the guidewire 43c and guided under fluoroscopy into the left subclavian vein ("LSV") 2b as shown in FIG. 13F. Liner 134b is expanded and released from the catheter, and the catheter 29d is withdrawn. Next, the catheter 29c is passed over the guidewire 43c and guided into the inferior vena cava 3b. Liner 134a is released and expanded within the IVC to the position shown in FIG. 13G.

Figure 13G:
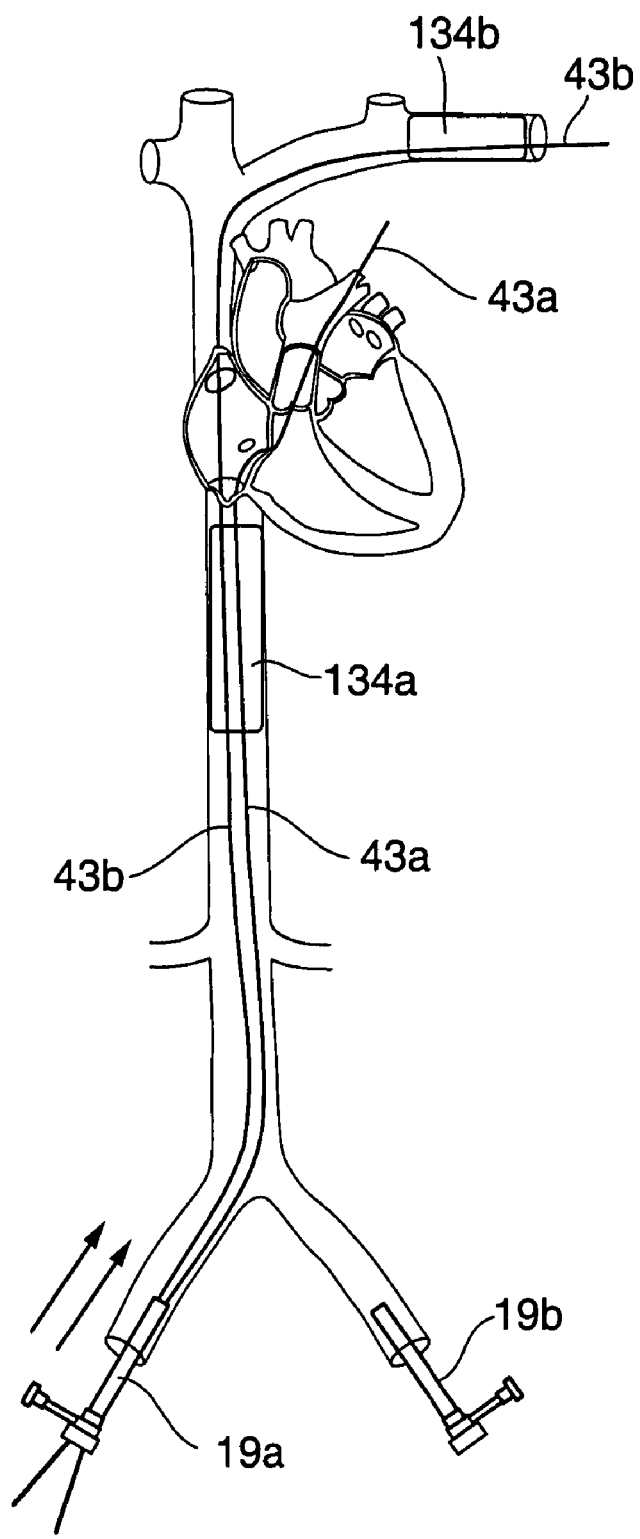

Next, guidewires 43a, 43b are inserted into introducer 19a. Guidewire 43b is under fluoroscopy into the LSV 2b and guidewire 43a is guided into the heart, through the right ventricle and into the pulmonary vein as shown in FIG. 13G. The leads 15c, 14c are threaded over the guidewires 43a, 43b as described above, and the mandrel 18 is attached to the device 12c. The mandrel 18 is advanced until the lead 15c is disposed in the desired position within the LSV, and the lead 14c has tracked guidewire 43a into the pulmonary vein. If a breakaway retention mechanism 30 (FIG. 2C) is used to hold the leads 15c, 14c in a streamlined configuration, its components release at this point, due to the divergent paths of the respective guidewires and leads.

The next step involves backing the lead 14c out of the pulmonary vein and directing it onto the right ventricle. This is accomplished by withdrawing the mandrel 18 (FIG. 13H) to retract the system slightly until the lead 14c and guidewire 43b slip out of the pulmonary vein and drop into the right ventricle 7a. The mandrel 18 is again advanced or rotated as described previously to seat the lead 14c within the right ventricular apex.

Figures 13H, 13I:
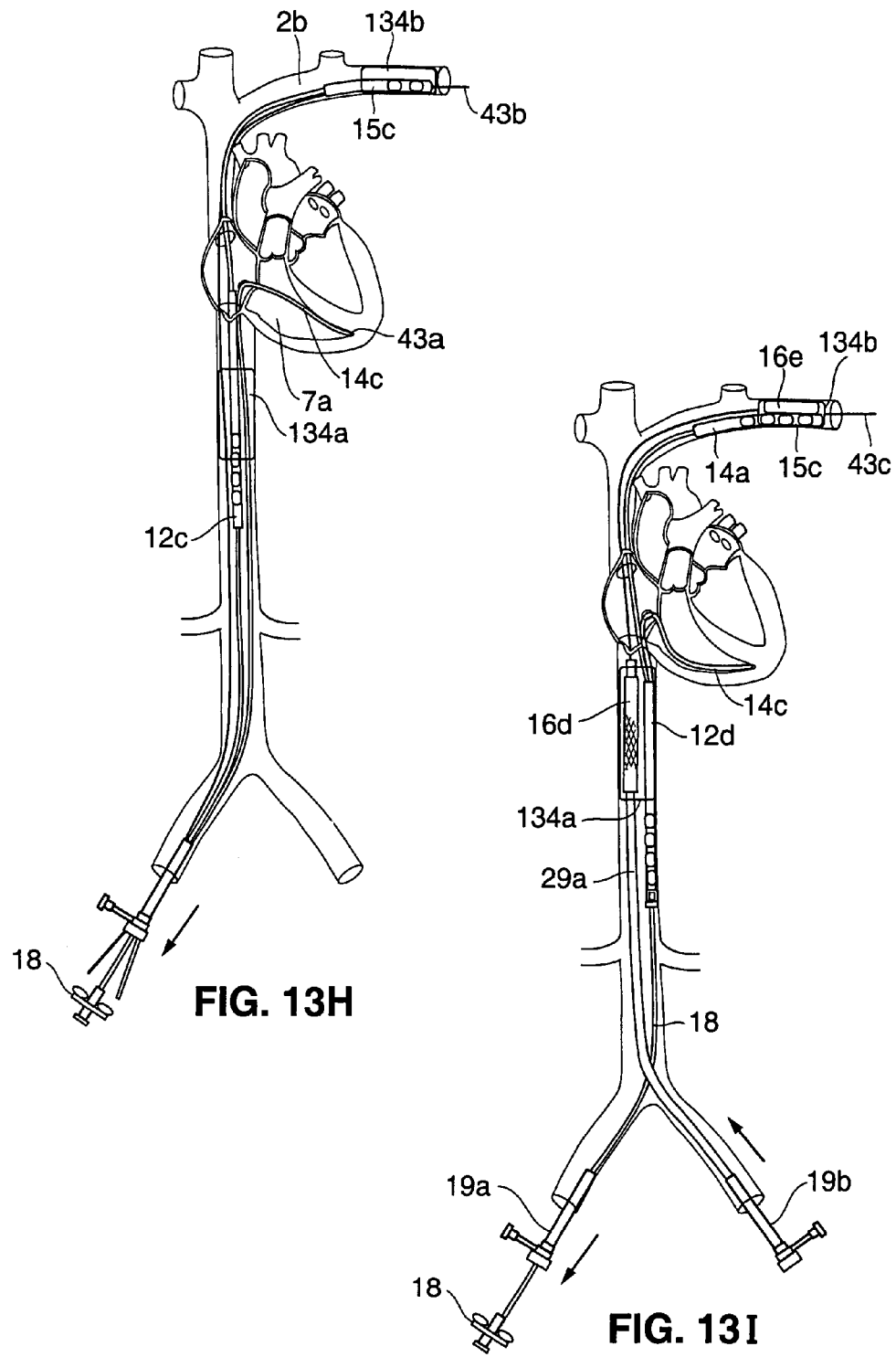

Next, if an anchor is to be used for the LSV lead 15c, guidewire 43c is passed through introducer sheath and into the LSV 2b, and delivery catheter 29b (FIG. 13D), with retention device 16e on it, is passed over the guidewire 43c and used to position the sleeve 16e adjacent to the lead 15c. The sleeve is expanded and released from the catheter 29b, leaving the lead 15c sandwiched between the liner 134b and retention sleeve 16e as shown in FIG. 13J. The retention device 16d is positioned in similar fashion by threading delivery catheter 29a over guidewire 43a, and advancing the retention device 16d into position adjacent to device 12c as shown in FIG. 13I. The retention device 16d is released and expanded into contact with the vessel wall, thereby retaining the device 12c.

Over time the liners may become endothelialized, particularly at their edges. However, the endothelial growth is self-limiting to the edge or rim of the liner due to increasing distance from a sustaining blood supply and should not reach the retaining sleeves. Thus, if it becomes necessary to explant the device 12d permanently or for servicing (such as to replace a battery for example) the retention sleeve 134a may be grabbed by a surgical instrument with the outer liner acting as a protective layer for the vessel. The liner may be left in place following removal of the retention sleeve and device 12d. If the device 12d (or a replacement) is to be later re-implanted, it may be returned to its original location within the liner.

Fourth Exemplary Method

Implantation of the device 12i of FIG. 8A will next be described with reference to FIGS. 14A through 14F. Prior to implantation, positioning mandrel 18 is attached to the proximal end of the device 12i and the ribbon coil 112 is wrapped around the mandrel 18. At least a portion of the device, and particularly the ribbon coil 112, is enclosed within a sleeve 142 (shown in a partially withdrawn position in FIG. 14A) to compress the coil 112 to the streamlined position for passage through the vasculature. The device is advanced through an introducer sheath (see sheath 19 of FIG. 2A) and pushed using mandrel 18 into the vasculature to the desired location.

Turning to FIG. 14B, once the device 12i has been advanced by mandrel 18 to the desired position, the sleeve 142 is withdrawn, allowing the ribbon coil 58a to spring to its expanded condition in contact with the vessel walls. The expanded coil may take the form shown in FIG. 14B, or it may spiral into overlapping layers to shorten its longitudinal dimension. A balloon catheter may be introduced into the vessel and expanded within the coil if needed for full expansion.

Figure 15A:
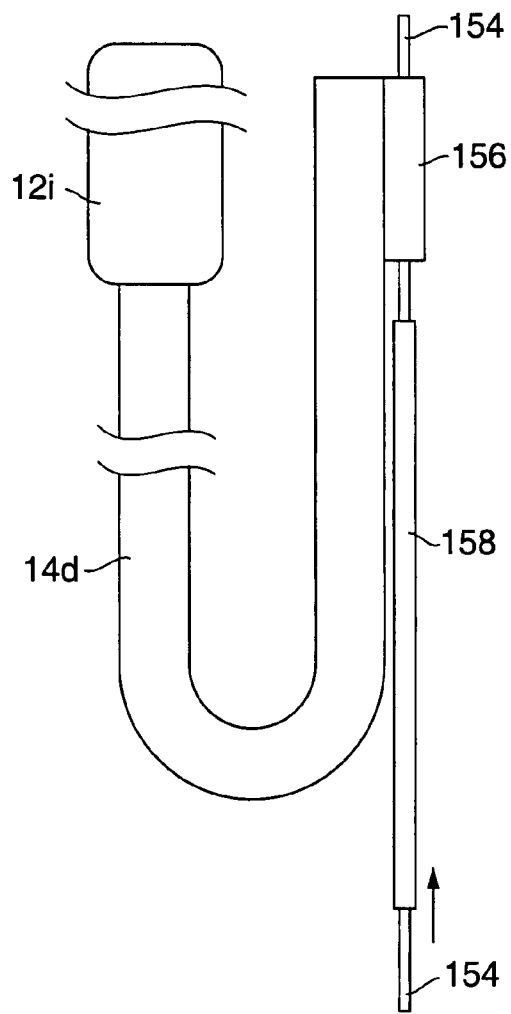
FIG. 15A is a plan view of a device similar to the devices of FIGS. 3A-3D and 8A-8B but slightly modified to include a cuff on the lead for receiving a guidewire.

At this point in the procedure, the device is anchored at the target location. A steerable guidewire 154 is threaded through the lead 14d near the lead's free end as shown in FIG. 15A and is passed through the introducer sheath into the vein and steered to the desired location. The lead preferably includes a cuff 156 for receiving the guidewire for this purpose. A pusher 158 is then threaded over the guidewire and advanced into contact with the cuff 156. Because cuff 156 is attached to the lead 14d, advancing pusher 158 pushes the lead 14d to the target site.

If the target lead location is within a vessel such as the left subclavian vein 2b as shown in FIG. 16A, and anchoring of the lead is desired, the lead is held in place while a sheath (similar to sheath 152 of FIG. 14D) having an anchor (see 16d of FIG. 14D) positioned inside it is moved into position in parallel with a distal portion of the lead. The sheath is withdrawn, releasing anchor 16d into the vessel. The anchor self-expands or is expanded, causing the anchor to radially compress the lead against the vessel wall.

If the target lead location is within a chamber of the heart, it may be secured at the target site using conventional securing means such as a helical fixation tip or tines on the distal end of the lead.

If a second lead is to be deployed, the procedure is repeated for that lead.

If further anchoring of the device 12i is desired beyond that provided by coil 58a, an integral anchor similar to anchor 16a of FIGS. 10E and 10E may be used, or a separate anchor 16d of the type shown in FIG. 9A may be used. FIGS. 14C-14F illustrate one method for anchoring the device using anchor 16*d*. Although these figures illustrate anchoring of device 12*i*, they are equally applicable to deployment of other devices within the vasculature, including the devices 12, 12*a*, and 12*b* and 12*c* as well as leads.

FIG. 14C shows the device 12*i* of FIG. 14A (attached to mandrel 18) after it has been advanced into the vessel and after the ribbon coil 58*a* has been released to the expanded position. Once the device 12*i* is in the desired position, a sheath 152 with the anchor 16*d* inside it is positioned in parallel with the device 12*i* while the device 12*i* is held in place using the mandrel 18. The sheath 152 is withdrawn as shown, releasing anchor 16*d* into the vessel. As discussed in connection with FIG. 9A, although the sheath 152 facilitates placement of the anchor, it should be considered optional.

Figure 14E:
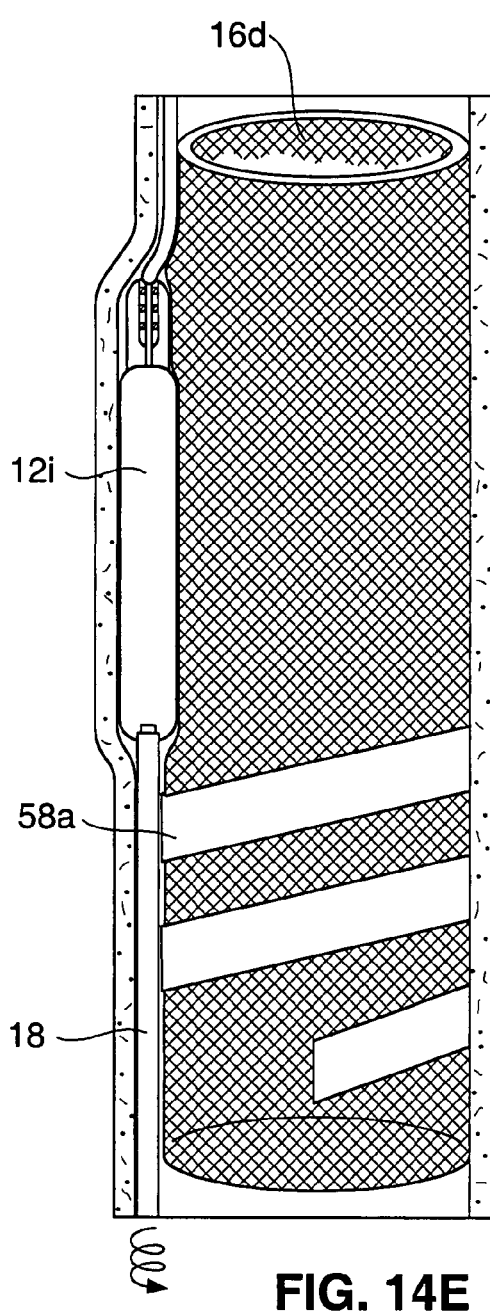
Figure 14F:
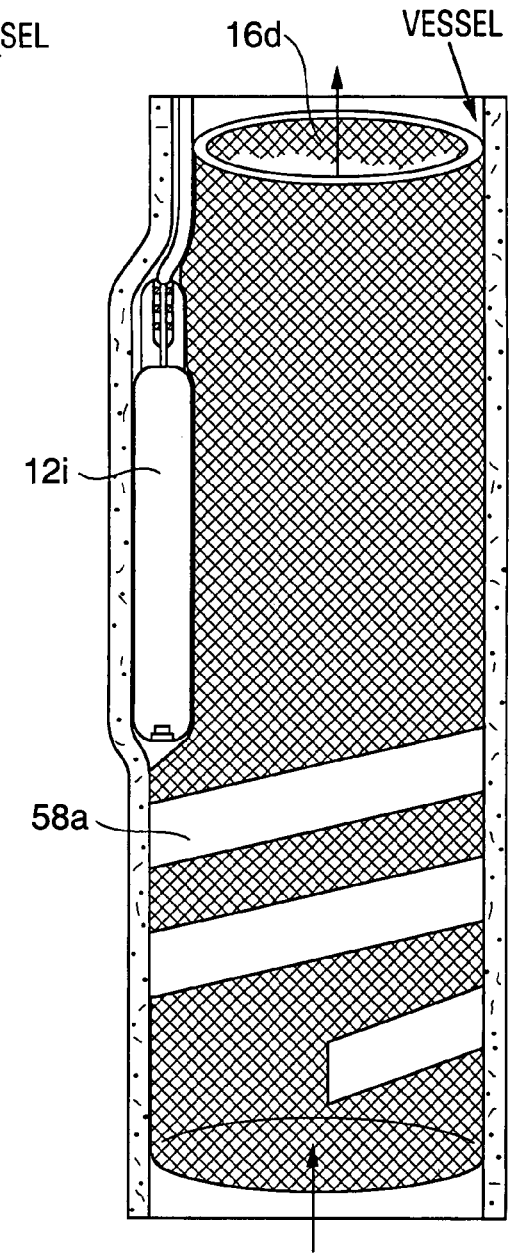

The anchor self-expands or is expanded using an expansion device such as a balloon (not shown) inflated within the anchor's central lumen, causing the anchor to radially engage the device 12*i* against the vessel wall. See FIG. 14E. Once the anchor is deployed, the mandrel 18 is detached from the device 12*i* and withdrawn from the body, leaving the device 12*i* and anchor 16*d* in the vessel as shown in FIG. 14F.

Fifth Exemplary Method

According to a yet another implantation method, implantation of the device (e.g. device 12*d* of FIG. 2F or the device 12*i* of FIG. 8A) involves first positioning the lead(s) at the desired location (i.e. in a vessel or in a chamber of the heart) and then positioning the device at the appropriate position. As with the method described with respect to FIG. 15A, this method of lead implantation preferably uses over-the-wire techniques that are widely used for cardiac lead placement. Using the over-the-wire procedure, an introducer sheath is inserted into the femoral vein (of elsewhere in the vasculature) and a steerable guidewire is inserted into the introducer sheath. With the aid of fluoroscopy, the physician guides the wire to the intended lead location. For example, for positioning a system in the configuration shown in FIG. 16A, the guidewire would be directed to the patient's left subclavian vein 2*b*, whereas for positioning in the configuration of FIG. 17B, the guidewire would be directed to the right ventricle 7*a*.

Figure 16C:
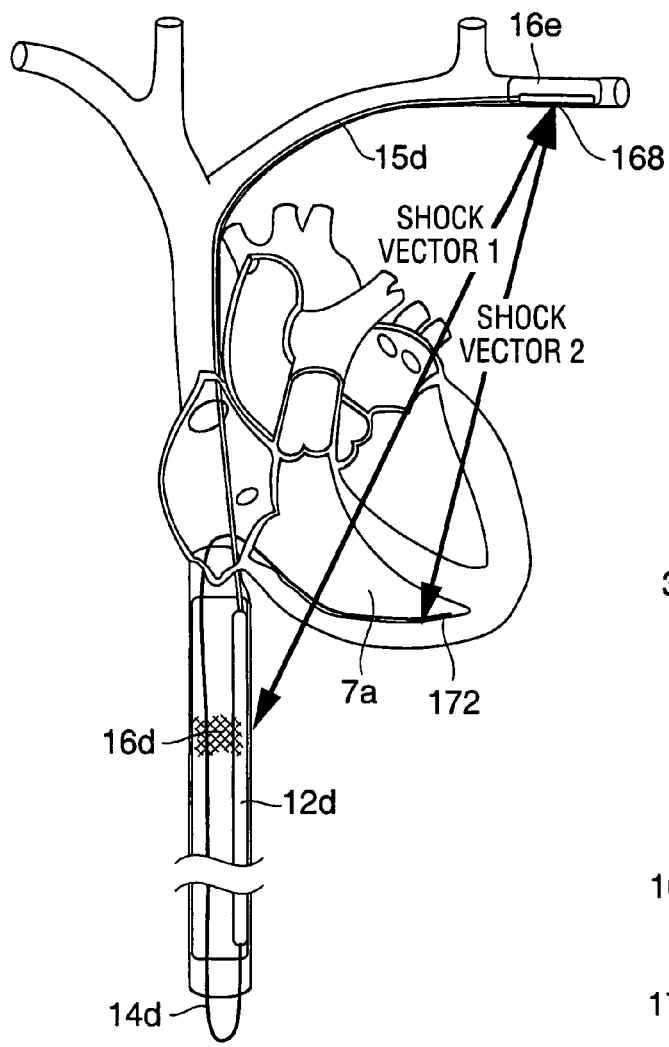
FIGS. 16A-20 schematically illustrate various applications of intravascular electrophysiological systems.
Figure 17A:
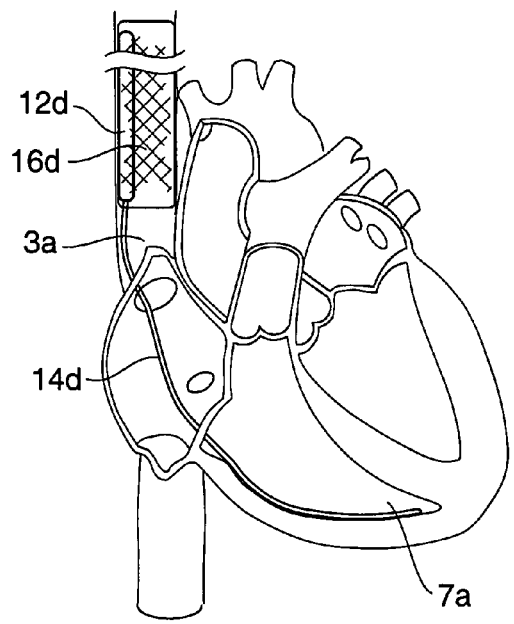
Figure 17B:
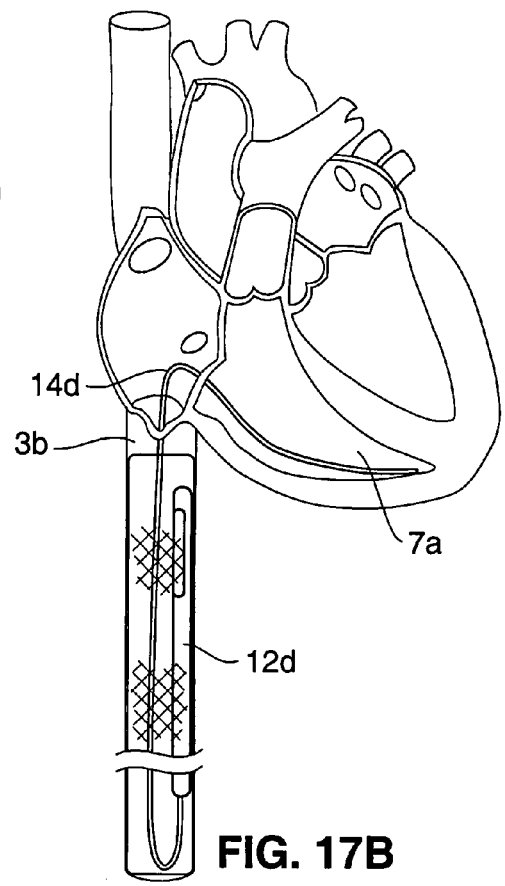

Next, the lead (e.g. lead 14*d* or 15*d* of FIG. 2F, or lead 15*d* of FIG. 16A, or lead 14*d* of FIG. 17B is threaded over the wire and pushed by the physician to the desired location. The lead is anchored at the desired location as described in connection with the first exemplary method. If a second lead is to be implanted, the process is repeated for the second lead.

Implantation of the device 12*d* begins once the distal end of the lead has been placed or anchored at the target location. At this point the proximal end of the lead preferably extends outside the body from the introducer sheath, which remains in the open vein. If the lead is provided as a separate component from the device, the lead is next attached to the device 12*d*.

Next, a positioning (e.g. mandrel 18 of FIG. 2F) is attached to the proximal end of the device 12*d*. Device 12*d* is advanced into the introducer sheath, and pushed using mandrel 18 (preferably under fluoroscopic visualization) to the desired location. Once at the desired location, device 12*d* is anchored in place using anchor 16*d* (FIG. 2F) as described in connection with the prior embodiments.

The positioning sheath, mandrel, and introducer sleeve are withdrawn from the patient.

Sixth Exemplary Method

The next example of an implantation method is similar to the prior example, but differs in that the leads and device are simultaneously advanced using the over-the-wire technique. As such, the sixth example is particularly useful for devices having pre-attached leads.

Figure 15B:
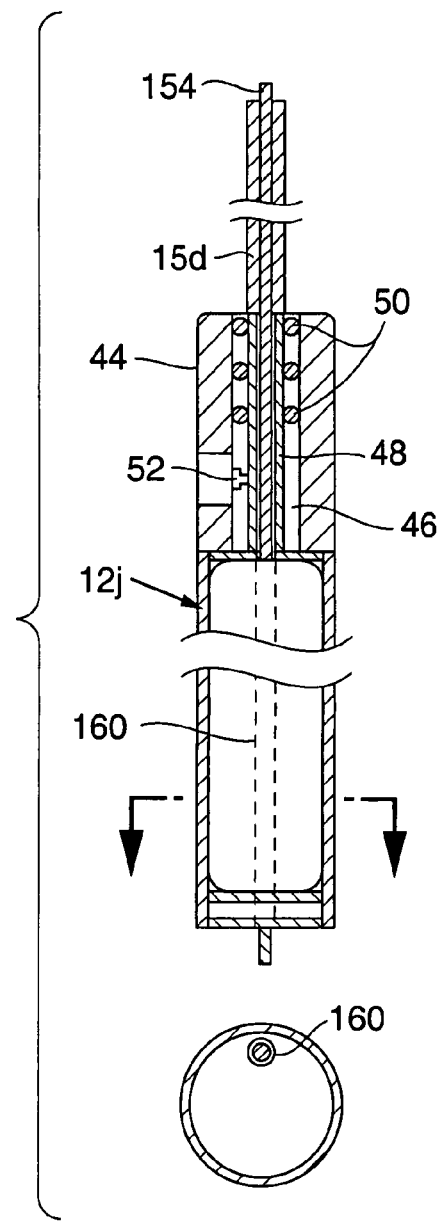
FIG. 15B is a plan view of a device similar to the devices of FIGS. 3A-3D and 8A-8B but slightly modified to include a bore in the device for receiving a guidewire.
Figure 15C:
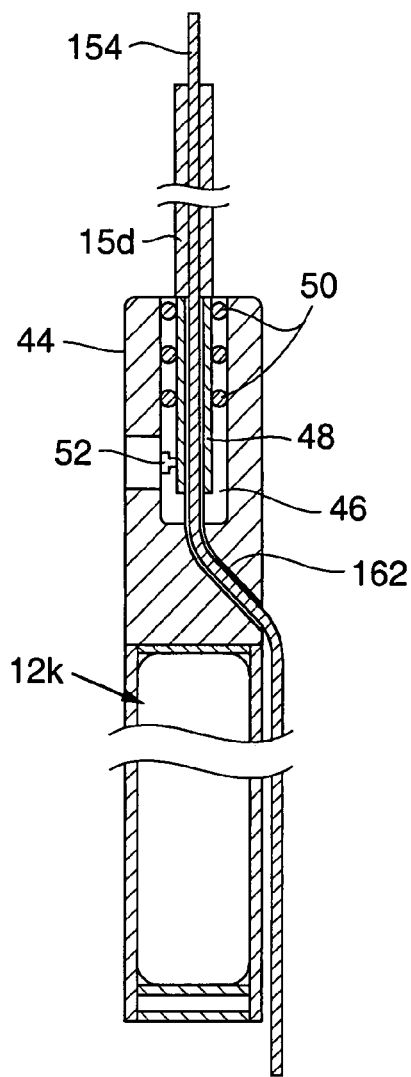
FIG. 15C is a plan view similar to FIG. 15B showing an alternative configuration for receiving a guidewire.

For this example, the lead and/or device is modified to allow the lead to be advanced over a guidewire even though it is attached to the device. Thus, as shown in FIG. 15B the body of the device 12*j* may be provided with a bore 160 that receives the same guidewire 154 that also extends through the lead 15*d*. Alternatively, a channel 162 may extend through a portion of the device 12*k* as shown in FIG. 15C. In this configuration, the guidewire 154 extends through the lead, into the channel 162, and then runs along the exterior of the device 12*k*. As yet another example, shown in FIGS. 15D and 15E, the lead 15*d* is modified to include a cuff 164 that receives the guidewire 154 externally of the lead, allowing the guidewire to run alongside the device 12*l*. It should be noted that although FIGS. 15A and 15B show o-ring seals 50 and a set screw 52, these features may be eliminated if the lead and device are provided to be integral with one another.

According to the sixth example, an introducer sheath is inserted into the femoral vein and a steerable guidewire 154 is inserted into the introducer sheath. The physician guides the guidewire to the intended lead location as described above.

Next, the lead 15*d* is threaded over the guidewire. If the FIG. 15B configuration is used, the proximal end of the guidewire 154 is threaded through the lead 15*d* and then passes through the bore in device 12*j*. If the FIG. 15C configuration is used, the proximal end of the guidewire passes from the lead into channel 162 in the device header, and then exits the device 12*k*. In either case, the lead is passed into the introducer sheath. The mandrel 18 (not shown in FIGS. 15A through 15D) is preferably attached to the device body and used to push the device and lead over the guidewire through the vasculature. Once the lead has reached the desired location, it is anchored at the desired location as described in connection with the first exemplary method. The mandrel 18 is used to maneuver the device to the target device position, and the device is anchored in place using the anchor as described above.

Figure 15D:
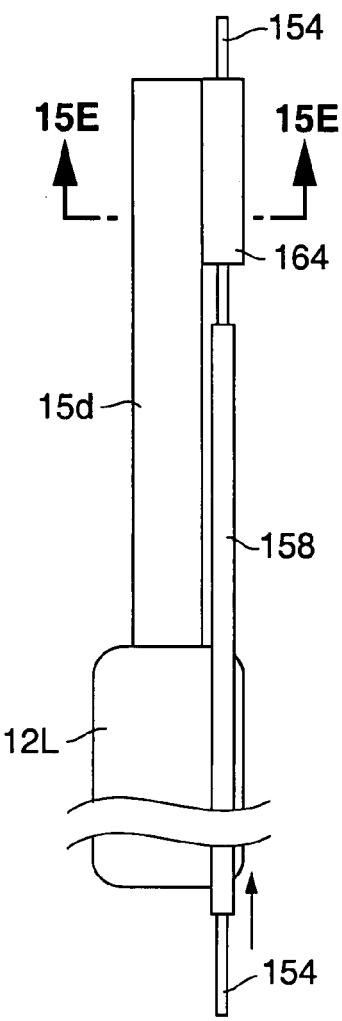
FIG. 15D is a plan view similar to FIG. 15A showing an alternative use of the FIG. 15A device and lead.
Figure 15E:
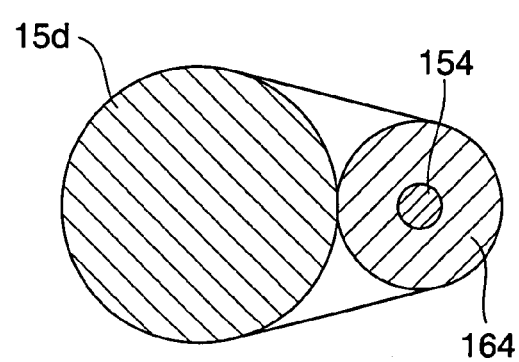
FIG. 15E is a cross-section view of the lead of FIG. 15D taken along the plane designated 15E-15E in FIG. 15D.

If the FIG. 15D configuration is used, the distal portion of the guidewire is threaded through cuff 164, and the mandrel (not shown) is attached to the device. The lead is passed into the introducer sheath. A pusher 158 is likewise threaded over the guide wire and advanced into contact with cuff 164. The pusher 158 is further advanced to push the lead to the desired location, at which time the lead is anchored as described. The mandrel is used to advance the device to the appropriate device position, and the device is then anchored in place.

Seventh Exemplary Method

A seventh example of an implantation method utilizes steps from prior examples and is useful for device configurations such as the FIG. 2F configuration in which leads 15*d*, 14*d* extend from opposite ends of the device. According to the seventh example, the superior lead 15*d* and device 12*d* are first implanted using the procedure of the sixth example (FIGS. 15B, C and D), thus leaving the inferior lead 14*d* extending out the incision in the femoral vein. Lead 14*d* is then carried into the vein and pushed to the desired position using the procedure illustrated in FIG. 15A and described as part of the fourth exemplary method.

Eighth Exemplary Method

An eighth example may be used to implant a device having a pre-attached lead. First, incisions are formed in the patient's subclavian 2*b* and in the femoral vein and introducer sheaths are inserted into each vessel. A guidewire is passed into the introducer sheath in the subclavian, through the right atrium to the left superior vena cava 3*a* and out the introducer sheath in the femoral vein. The end of the guidewire extending out the femoral vein is attached to the lead, and is then withdrawn at the subclavian incision, thereby pulling the lead into the subclavian and drawing the device that is attached to the lead into the inferior vena cava. The mandrel 18 may be used as described above to facilitate "fine-tuning" of the device position. The lead and/or device are anchored as described above.

Ninth Exemplary Method

Figure 17C:
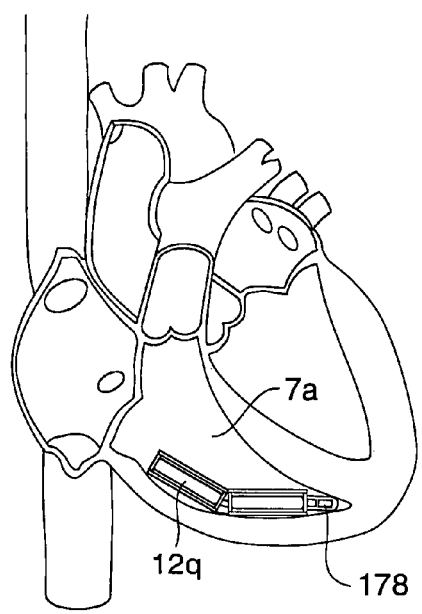

A "leadless" embodiment shown in FIG. 17C may be provided with a bore or similar means for receiving a guidewire, in which case it may be implanted by first directing a guidewire through the subclavian or inferior vena cava to the right ventricle, threading the device over the guide wire, and then pushing the device (e.g. using mandrel 18) to the ventricle. Alternatively, the device may be advanced through a hollow catheter having its distal end positioned in the right ventricle.

Applications

Intravascular electrophysiological systems of the type described herein are adaptable for use in a variety of applications, including single chamber atrial or ventricular pacing, dual chamber (atrial and ventricular) pacing, bi-atrial pacing for the suppression of atrial fibrillation, bi-ventricular pacing for heart failure patients, cardioversion for ventricular tachycardia, ventricular defibrillation for ventricular fibrillation, and atrial defibrillation. The system may be adapted to perform multiple functions for use in combinations of these applications. The system may be implanted for permanent use, or it may be implanted for temporary use until more permanent interventions can be used.

In general, the system is responsive to fast and/or irregular heartbeats detected using sensing electrodes positioned on the device body and/or leads. Typically, at least two primary sensors will be positioned across the heart so as to provide a macroscopic view of the electrical activity of the heart. Common locations for these primary sensors will include a position below the heart such as the inferior vena cava 3b, and a position above the heart such as the superior vena cava 3a or the left subclavian vein 2b. Data obtained from these sensors may be optionally supplemented with localized data from more closely spaced sensors at particular areas of interest, such as the right atrium. This data can bring into focus the nature of the abnormal activity detected by the primary sensors, and can allow the system to be programmed to differentiate between electrical activity requiring delivery of corrective defibrillation or pacing pulses, and electrical activity that can resolve without intervention.

The system should be programmed to deliver sufficient energy to disrupt the aberrant electrical activity and restore the heart to its normal rhythm. Energy pulses of approximately 1 J to 50 J may be used for ventricular defibrillation, whereas pulses in the range of 0.1 J to 40 J may be needed for atrial defibrillation. Pacing pulses may be delivered in the range of 0.1 to 10 Volts, with 0.1 to 2.0 millisecond pulse widths. The system may be programmed to deliver a specific amount of energy or to determine the appropriate energy level.

FIGS. 16A through 20 illustrate some of these applications, some configurations of the system that are suitable for each application, and shock vectors deliverable to the heart as a result of the configurations. The intravascular electrophysiological device embodiments and associated anchors and other components may be used for the described applications, although numerous alternative forms of electrophysiological devices and anchoring mechanisms may also be used without departing from the scope of the invention.

The applications that follow reference placement of the device in the venous system, although the device and/or electrodes may alternatively be placed within the arterial system (such as to allow generation of defibrillation vectors from the aortic arch to the descending aorta) if warranted. Moreover, while this section describes certain electrode combinations that can produce shock vectors across the heart, these combinations are given by way of example and are not intended to limit the scope of the claims. Generally speaking, the system may be implanted to include electrodes in any vessel and/or chamber of the heart arranged to distribute energy through the heart in a manner sufficient to control the aberrant electrical activity of the heart.

More specifically, FIGS. 16A through 20 show electrodes in various combinations positioned in the left subclavian vein, inferior vena cava, left ventricle, right ventricle, right atrium, middle cardiac vein, and coronary sinus, however defibrillation electrodes may be positioned within other vessels, including but not limited to the pulmonary vein, hepatic vein, renal vein, axillary vein, lateral thoracic vein, internal thoracic vein, splenic vein. These locations may provide particularly good substitutes for lead placement in the right ventricle for several reasons. For example, when used in combination with electrodes in the left subclavian and in the inferior vena cava, electrodes in these alternate locations result in shock vectors that satisfactorily surround the heart. Additionally, electrode placement within a vein can be more stable, even in the absence of an anchor, than electrode placement in the heart, and so avoiding lead placement within the heart can thus simplify the implantation procedure.

FIGS. 16A and 16B show components of the FIG. 2F system 10d as used as an implanted cardioverter defibrillator (ICD) for treatment of ventricular fibrillation. In this configuration, device 12d is anchored in the inferior vena cava 3b using anchor 16d.

A defibrillation lead 15d is positioned and optionally anchored within the patient's left subclavian. An anchor 16e similar to the anchor 16d may be used for this purpose. Anchor 16e may be smaller than anchor 16d since the lead 15d it anchors is relatively lighter than the device anchored by anchor 16d, and because the anchor 16a is positioned within the smaller-diameter left subclavian.

As discussed previously, the lead 15d may include a coiled section 166 as shown in FIG. 16B to permit elongation of the effective length of the lead in response to longitudinal tension.

Referring again to FIG. 16A, lead 15d includes a high voltage electrode surface 168 through which the defibrillation pulse is delivered. During defibrillation, the defibrillation shock vector flows between electrode surface 168 on the lead and the electrode surface 170 on the device 12d as indicated by arrows. Orienting the electrode 170 towards the heart as shown in FIG. 16A contributes to focusing of the defibrillation current. Moreover, because the anchor 16d functions as an insulator, it helps to minimize conduction of the high voltage current away from the heart and thus also facilitates current focusing. Configuring the system to focus the current can reduce the amount of defibrillation energy needed to defibrillate the patient, since less energy is lost to surrounding tissue, and allows a smaller capacitor to be used within the system. This is beneficial in that it reduces the overall size of the device 12d and further ensures that the device profile will not interfere with blood flow within the vessel.

Although electrode surface 170 is shown positioned towards one side of the device, it may take other forms. For example, the electrode surface may instead extend around the device body to form a band. Focusing is facilitated in this embodiment by positioning the anchor 16d against the side of the device that is furthest from the heart (as is also done in the FIG. 16A application), so as to thereby minimize conduction of the high voltage current from the electrode 170 away from the heart.

In the FIG. 16A application, electrical activity of the heart may be sensed between the high voltage electrode 168 or another electrode on the lead 15d and the electrode 170 on device 12d. Device 12d may alternatively include one or more separate sensing electrodes (not shown) on its surface for detecting electrical activity of the heart.

FIG. 16C illustrates a second application for the FIG. 2F system. This application is similar to the first application in that it uses the device 12d as an implantable cardioverter defibrillator ("ICD"), but it further includes a pacing or defibrillation lead 14d positioned in the right ventricle 7a. Pacing lead 14d may be a conventional lead, which includes one or more sensing and pacing electrodes 172. For example, a bi-polar lead of a type commonly used for ICD's and pacemakers may be used, in which case sensing could be carried out between two spaced-apart electrodes on the lead. If a smaller lead is desired, it may be provided with a single sensing electrode and sensing could be accomplished between the single electrode and an exposed electrode (see electrode 170, FIG. 16A) on device 12d. It should be noted that although FIG. 16C shows the defibrillation lead 15d and the sensing lead 14d extending from opposite ends of the device 12d, both leads may instead extend from one end of the device.

For defibrillation, the FIG. 16C arrangement may be configured such that the shock vector applied to the heart extends from the defibrillation electrode 168 and a location on the device 12d as indicated by arrows. Alternatively, a high voltage lead may be used as the lead 14d, in which case the device could also be configured to apply the shock vector between electrode 168 and the electrode 172 on lead 14d.

Figure 16D:
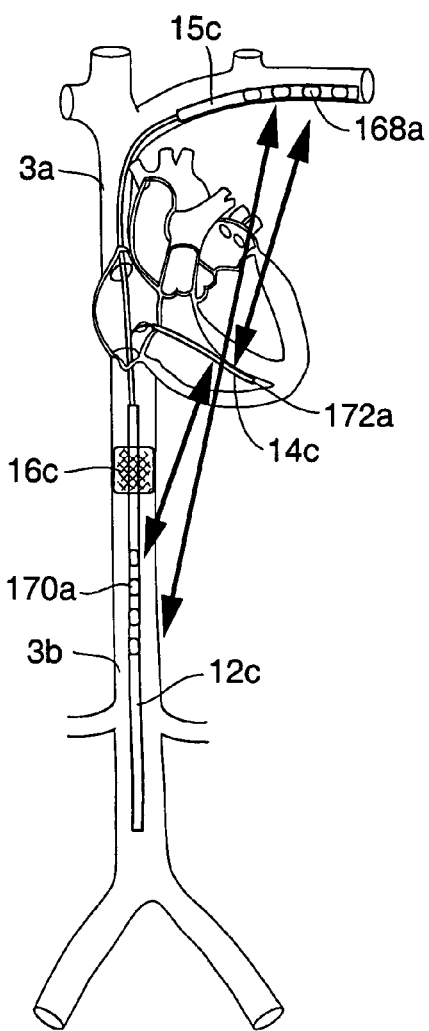

FIG. 16D illustrates shock vector patterns that may be delivered using the FIG. 2C system. As shown, shock vectors may be delivered between electrodes 168a on lead 15c in the LSV and electrodes 170a on device 12c, and between LSV electrodes 168a and RV electrodes 172a. Shock vectors may also be applied between the RV electrodes 172a and the electrodes 170a on device 12c. All, or any subset, of the illustrated shock vectors may be applied simultaneously, sequentially, or in various combinations. For example, the system may be programmed to deliver energy only between the electrodes 168a in the left subclavian and the electrodes 172a in the right ventricle. Naturally, other embodiments including those of FIGS. 11F and 12E can be used to obtain similar shock vectors. As discussed previously, the RV electrodes 172a (in this as well as the other embodiments utilizing RV electrodes) may instead be positioned in the middle cardiac vein, hepatic vein, renal vein, axillary vein, lateral thoracic vein and splenic vein. Moreover, the device body 12c may be positioned in the superior vena cava 3a rather than the inferior vena cava 3b, allowing for delivery of alternative shock vectors between its electrodes 170a and the electrodes 168a, 172a in the left subclavian and right ventricle, respectively.

Figure 16F:
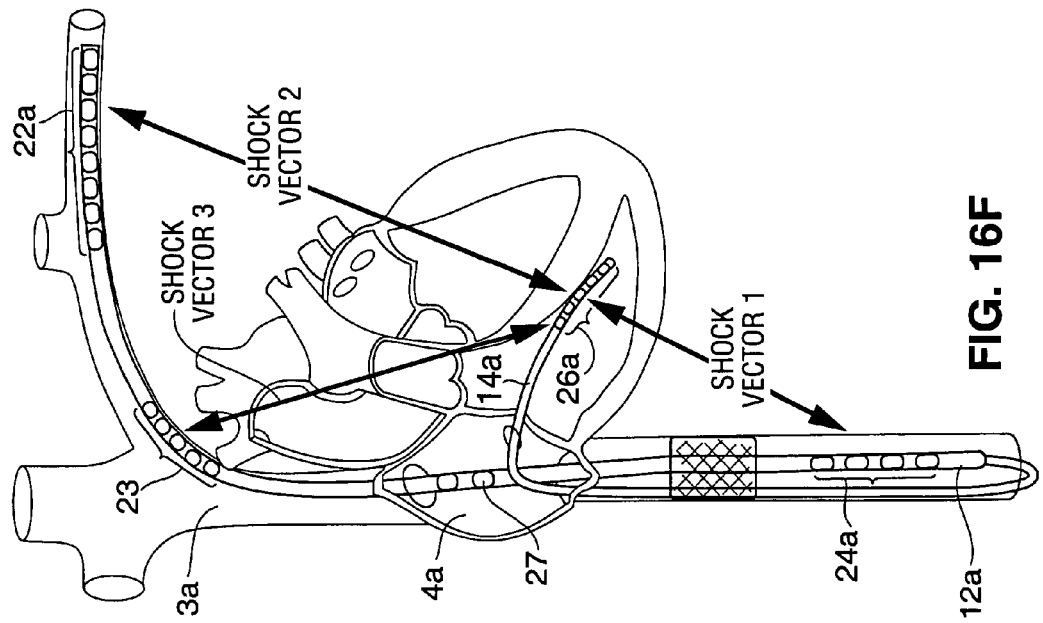
Figure 16E:
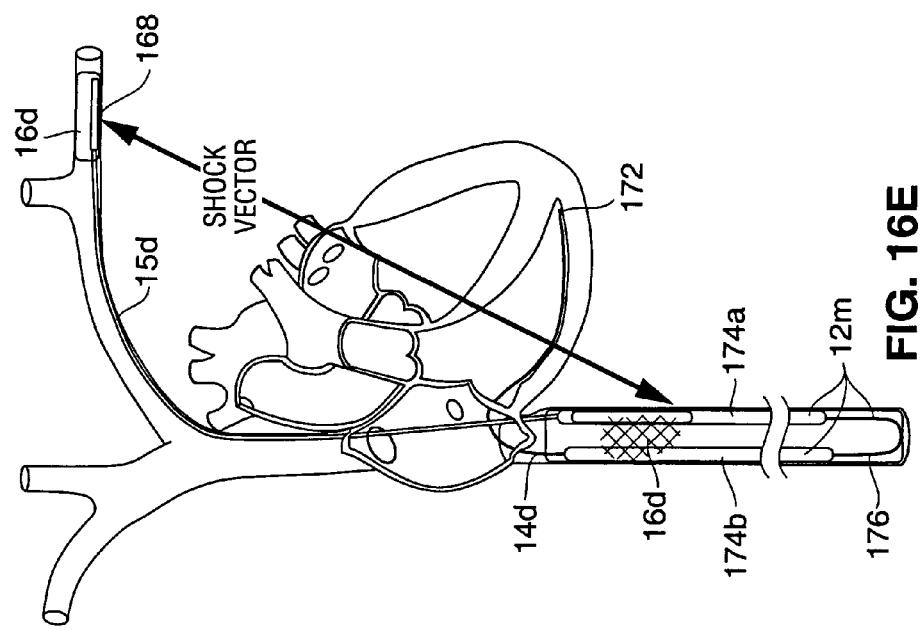

A fourth application is shown in FIG. 16E. The fourth application is largely similar to the third application, but uses a device 12m that is divided into two separate housings 174a, 174b. For example, housing 174a may contain the components needed for defibrillation (e.g. the electronics, capacitors and the batteries) while housing 174b contains the components associated with the sensing function (e.g. the electronics and associated batteries).

Dividing components into separate packages may provide several advantages. First, it allows for use of an anchor having a shorter longitudinal dimension, which facilitates placement of the anchor in a location where it will not obstruct blood flow into/from peripheral vasculature. The separate packages can be anchored by a single anchor 16d as shown in FIG. 16E, or the packages may be positioned in series in the vessel and separate anchors may be used for each.

Second, battery life may be optimized by using separate batteries for pacing and defibrillation—thereby supporting each function with a battery type most suitable for the function and optimizing battery life. For example, one or more batteries having chemistries of the type used for pacemaker batteries (typically lithium iodide batteries which can come in very small sizes due to their high energy density) may be used for the low current pacing and sensing function. Batteries having chemistries similar to typical implantable defibrillator batteries, which are faster charging and which can produce larger current surges than pacing batteries, (e.g. LSOV) may be separately used for the defibrillation function. Third, as discussed previously, physically isolating the sensing components from the defibrillation components can improve electrical sensing performance during device charging.

An inter-device cable 176 provides communication between the components of the housings 174a, 174b, although other forms of communication (e.g. wireless RF, infrared, acoustic, telemetric) might also be used. As yet another alternative, the structural framework of the anchor 16d may be used as a conductor or antenna for this purpose.

FIG. 16F shows device 12a of FIG. 11F as modified to include an additional array 23 of defibrillation electrodes positionable near the superior vena cava 3a, as well as sensing electrodes 27 positioned to detect supraventricular (or atrial) tachycardia. Supraventricular tachycardia is significantly less life threatening than ventricular tachycardia, and does not require treatment using the large shocks needed to treat ventricular tachycardia. The presence of sensing electrodes 27 in the right atrium gives the system a local reading of electrical activity within the atria. This allows the system to differentiate between supraventricular tachycardia and episodes of ventricular tachycardia that will be detected using the primary sense electrodes positioned above and below the heart, such as in the inferior vena cava 3b and the superior vena cava 3a or the left subclavian vein 2b. When abnormal electrical activity is detected by the primary sense electrodes, data from the electrodes 27 reflecting supraventricular tachycardia will trigger the system to forgo delivery of corrective shocks (or to trigger lower energy pulses to bring the heart out of the supraventricular tachycardia), thereby preserving battery life and preventing the discomfort that the patient might experience if the system were to treat the arrhythmia as a ventricular tachycardia and thus deliver a higher energy shock. In the event a ventricular tachycardia is detected, energy may be delivered along shock vectors extending between the LSV electrodes 22a and the RF electrodes 26a, and/or between the RV electrodes 26a and the IVC electrodes 24a, and/or the LSV electrodes 22a and the IVC electrodes 24a, and/or between the SVC electrodes 23 and the RV electrodes 26a.

Figure 16H:
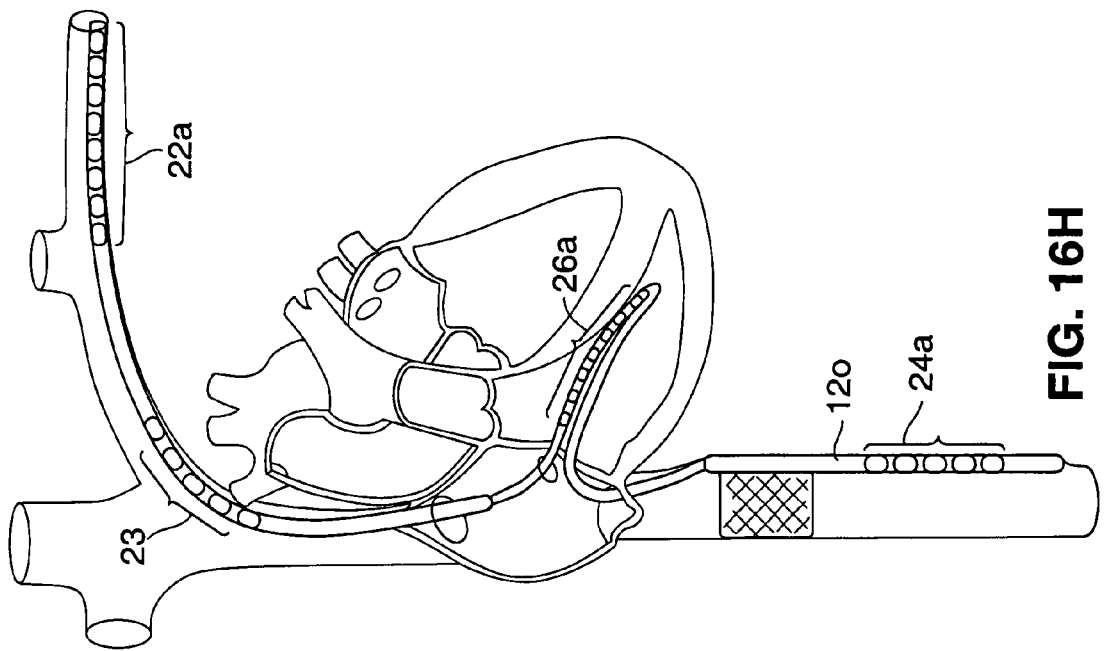
Figure 16G:
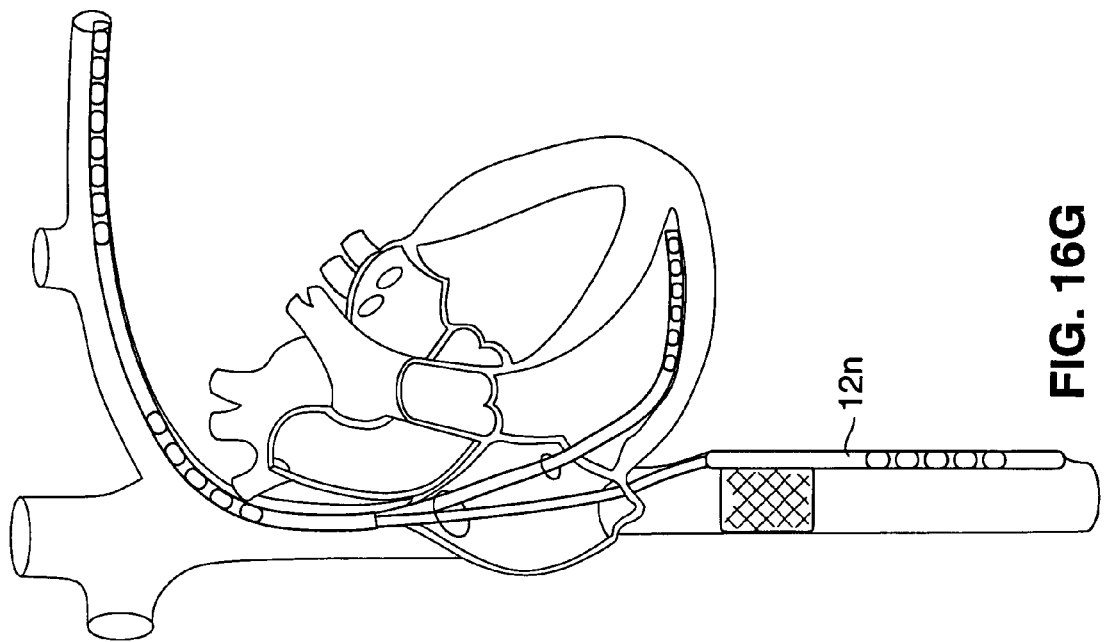

FIG. 16G shows an alternative configuration of a device 12n that is similar to the bifurcated device 12c of FIG. 2C but that is inverted such that the bifurcation is on the inferior end of the device 12n. Shock vectors similar to those shown in FIGS. 16D and 16F may be attained using the device 12n. As with prior devices, the device 12n may be introduced superiorly such as through the brachiocephalic vein or subclavian, or inferiorly through the inferior vena cava. FIGS. 16H and 16I shows additional configuration of devices designated 12o and 12p, respectively, which may be used to achieve similar shock vectors. In the FIG. 16I embodiment, some of the electrodes are shown in contact with the septal wall.

Figure 16J:
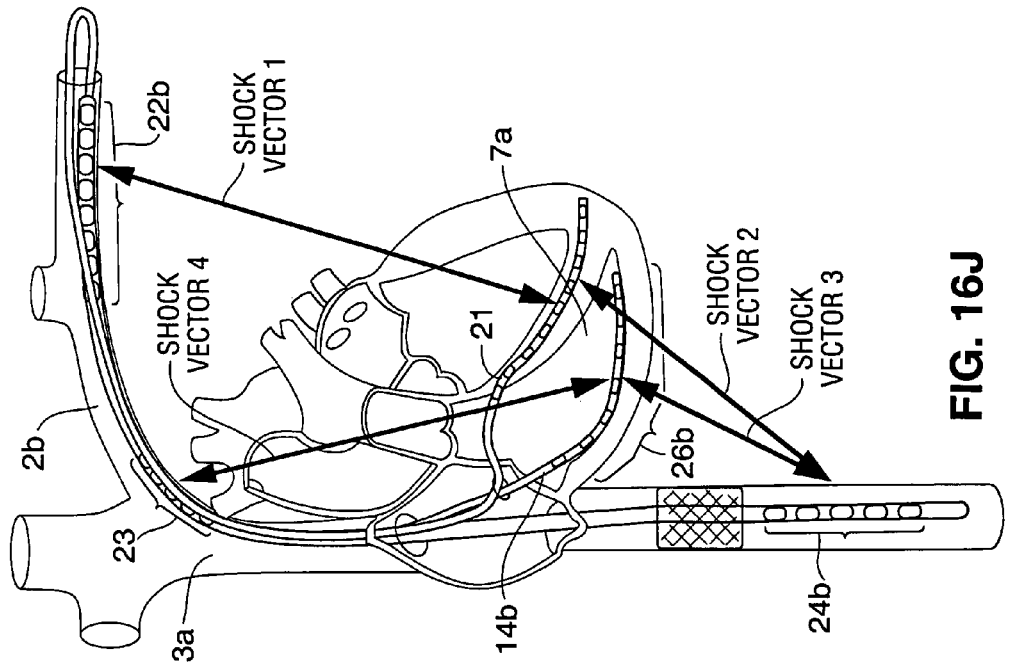
Figure 16I:
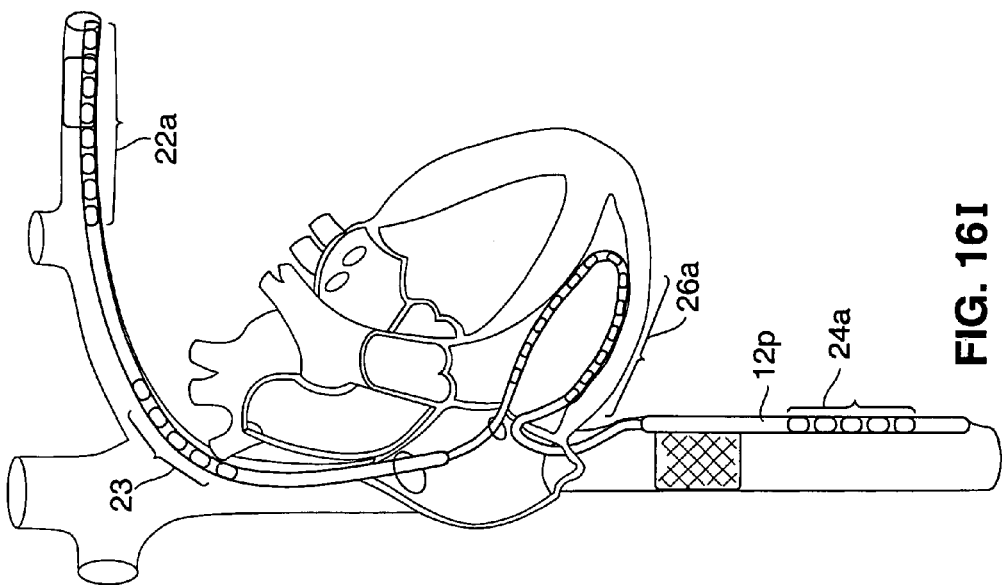

FIG. 16J shows the FIG. 12E/FIG. 2B device 12b as modified to include a second electrode lead 21 positionable in the middle cardiac vein, and to include an array 23 of electrodes 23 positionable within the superior vena cava 3a or within the left subclavian vein 2b. The electrodes 23 may be on the device 12b or on either of the leads 21, 14b. Shock vectors include those described with respect to prior embodiments, as well as vectors extending between middle cardiac vein lead 21 and the IVC electrodes 24b and/or the LSV electrodes 22b. It should be noted that the FIG. 16J configuration may be further modified to eliminate the RV lead 14b.

Figure 16K:
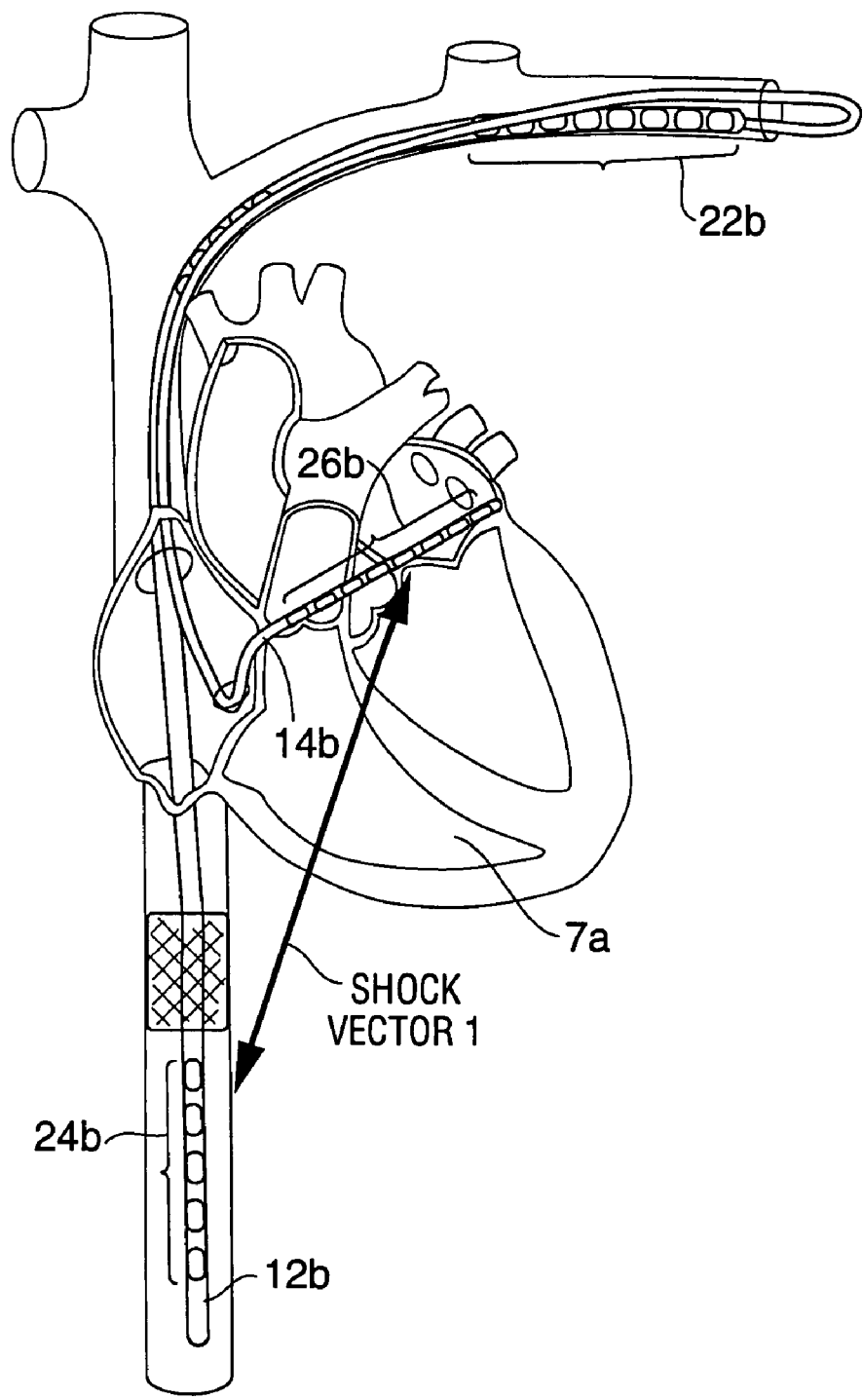

In yet another alternative shown in FIG. 16K, lead 14b may be positioned in the coronary sinus of the heart, thus enabling use of shock vectors extending between the electrodes 26b on the coronary sinus lead 14b and the IVC electrodes 24b on the device body 12b. A second lead may be connected to the device and placed in the right ventricle 7a to allow application of a shock vector between the coronary sinus and the right ventricle.

FIG. 17A shows an alternative application in which the FIG. 2F system is used for single-chamber ventricular pacing. As shown, device 12d is anchored by anchor 16d in the superior vena cava 3a. The distal end of pacing lead 14d is positioned in the right ventricle 7a. As shown in FIG. 17B, the device 12d and anchor 16d may alternatively be positioned within the inferior vena cava 3b. As yet another variation on this application shown in FIG. 16C, a leadless device 12q having a surface pacing electrode 178 is itself positioned within the right ventricle 7a.

Figure 18A:
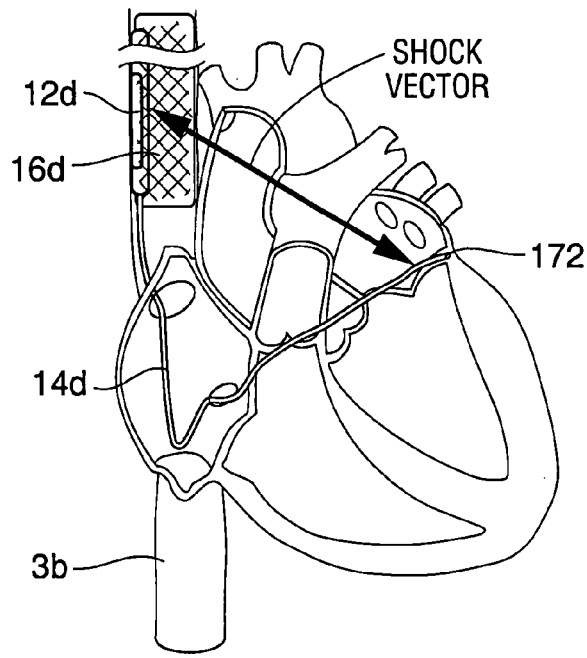
Figure 18B:
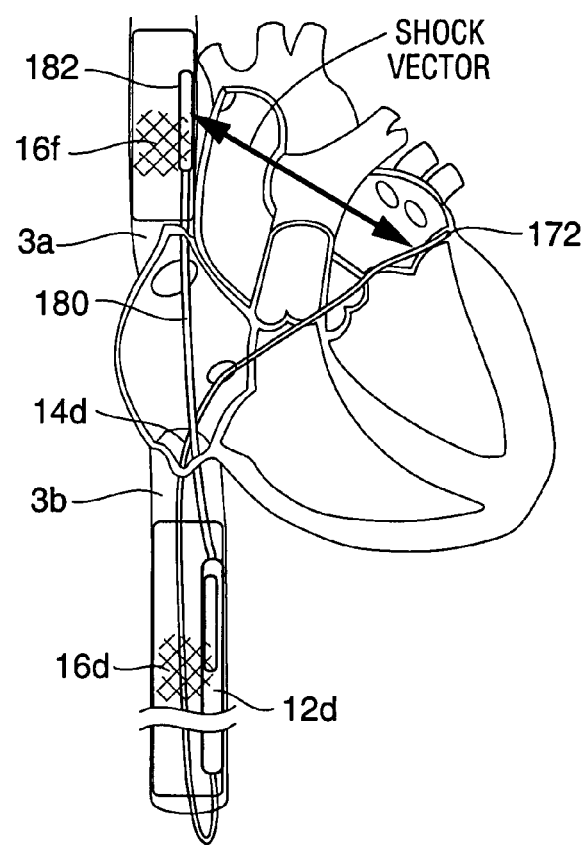

FIG. 18A shows an alternative application in which the FIG. 2F system is used to treat atrial fibrillation, with device 12d anchored by anchor 16d in the superior vena cava 3a, and a sensing/pacing lead 14d having electrode 172 extending through the coronary sinus. Using this embodiment, the shock vector extends between an exposed electrode on device 12d and electrode 172 within the coronary sinus. FIG. 18B shows an alternative to the FIG. 18A configuration for atrial fibrillation, in which the device 12d may be positioned in the inferior vena cava 3b and a high voltage electrode lead 180 placed in the superior vena cava 3a. Lead 180 may optionally be retained by an anchor 16f. In this variation, the cardioversion shock vector extends between a distal electrode on pacing lead 172 and a high voltage electrode 182 on lead 180. Other applications utilizing a coronary sinus electrode may employ shock vector patterns between the coronary sinus electrodes and electrodes in the right ventricle 7a, inferior vena cava, middle cardiac vein, the pulmonary vein, left hepatic vein, renal vein, axillary vein, lateral thoracic vein, internal thoracic vein, and splenic vein.

Figure 19A:
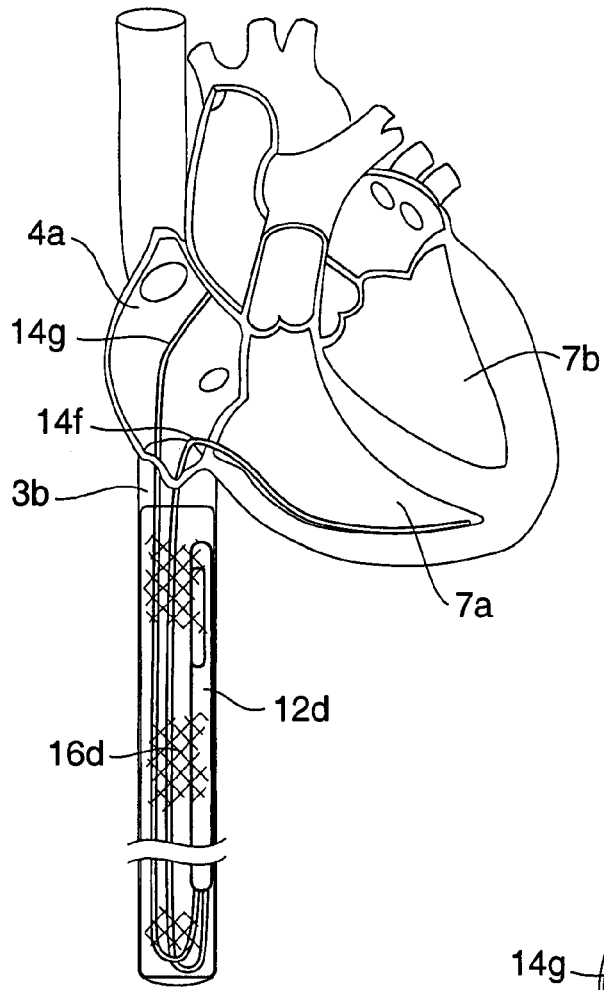
Figure 19B:
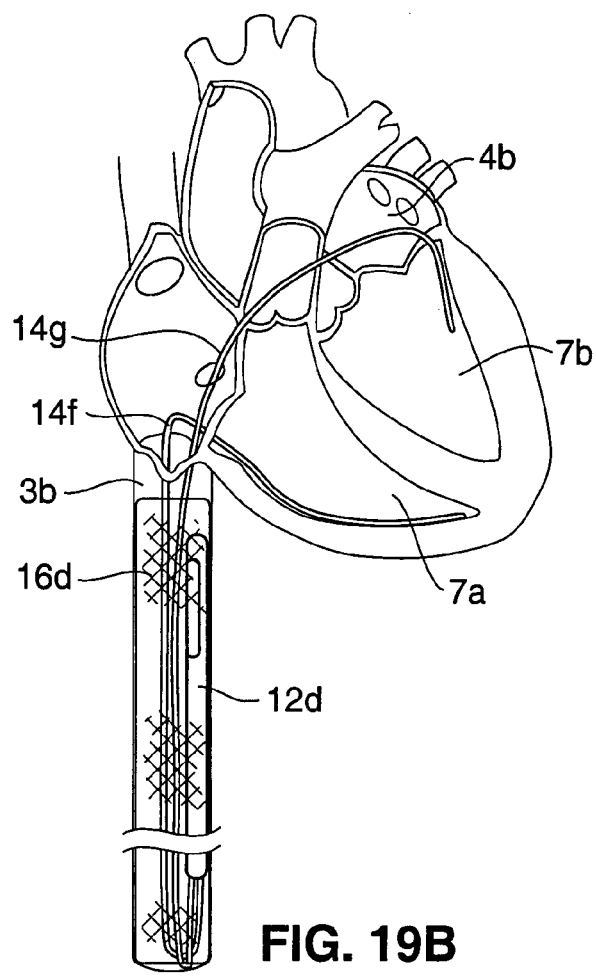

FIGS. 19A and 19B shows use of the FIG. 2F system as a dual chamber pacer having two pacing leads 14f, 14g. Device 12d is anchored in the inferior vena cava 3b using anchor 16d. The FIG. 19A embodiment is shown positioned for pacing the right and left ventricles. Ventricular pacing is performed by one of the pacing leads 14f which is positioned in the right ventricle 7a as shown, and atrial pacing is performed using another pacing lead 14g that is positioned in the right atrium 4a in contact with the intra-atrial septum. The FIG. 19B embodiment is shown positioned for bi-ventricular pacing, with each of the pacing leads 14f, 14g positioned in one of the ventricles 7a, 7b. Access to the left ventricle 7b may be attained trans-septally with a puncture or through a naturally occurring septal defect. A similar approach may be used to access the left atrium 4b in other applications requiring left atrial electrodes.

Figure 20:
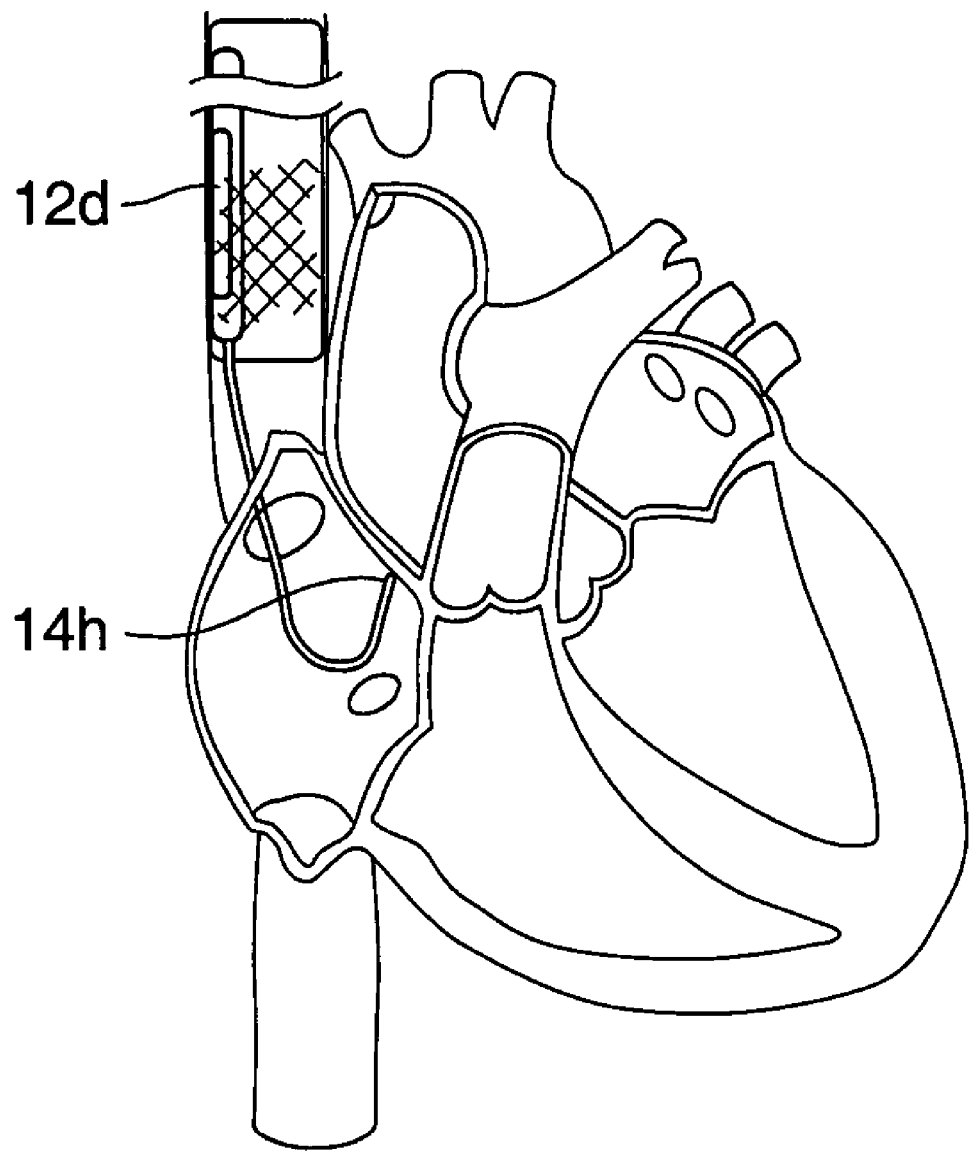

FIG. 20 shows use of the FIG. 2F system for atrial pacing. In this application, an atrial J-lead 14h is coupled to the device 12d and is positioned in contact with the intra-atrial septum.

Alternative Applications

It should be pointed out that many of the device configurations, components, retention devices and methods, implantation methods and other features are equally suitable for use with other forms of intravascular implants. Such implants might include, for example, artificial pancreas implants, diagnostic implants with sensors that gather data such as properties of the patient's blood (e.g. blood glucose level) and/or devices that deliver drugs or other therapies into the blood from within a blood vessel. More particularly, fully implantable intravascular systems may be used for administering drugs including hormones, chemotherapeutic agents, pharmaceuticals, synthetic, recombinant or natural biologics, and other agents within the body. Generally speaking, the systems include drug reservoirs and associated components (e.g. batteries, electronics, motors, pumps, circuitry, telemetric components, sensors) that are anchored in the vasculature and programmed to administer drugs into the bloodstream or directly into certain organs or tissues. Drug delivery microtubules may extend from the device body and into surrounding vessels in a similar way that the leads in the embodiments described above extend from the device body. These microtubules may be positioned within the vasculature to deliver drugs directly into the bloodstream, and/or they may extend from the device through the vascular into or near a body organ. For example, by directing drugs to a particular aortic branch (e.g. hepatic artery, renal artery, etc), an intravascular delivery device can achieve target delivery of therapeutic drugs to specific organs including the brain, liver, kidneys etc.

In some embodiments, such intravascular drug delivery systems may be controlled remotely using telemetry or via internal intelligence that may be responsive to in-situ sensing of biological, physical or biochemical parameters.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

What is claimed is:

1. A method for retaining a medical device within a blood vessel, comprising the steps of:
    providing an expandable retention device and an intravascular medical device;
    positioning the medical device in a blood vessel;
    placing at least a portion of the retention device in contact with the medical device;
    with the retention device in the compressed position, positioning the retention device in the blood vessel; and
    expanding the retention device to the expanded position to retain the medical device within the vessel wherein the medical device includes a pulse generator.

2. The method of claim 1, wherein the placing step includes coupling the medical device and the retention device prior to the positioning step.

3. The method of claim 1, wherein the placing step includes coupling the medical device and the retention device after the positioning step.

4. The method of claim 1, wherein the medical device and retention device are separated components, and wherein the placing and expanding steps include expanding the retention device into contact with the medical device within the vessel.

5. The method of claim 4, wherein the placing and expanding steps include:
   with the retention device in the compressed position, positioning the retention device in the vessel adjacent to the medical device; and
   expanding the retention device to the expanded position to engage the medical device between an exterior surface of the retention device and a surface of the vessel.

6. The method of claim 1, wherein the retention device is an expandable retention sleeve.

7. The method of claim 6, wherein the retention sleeve substantially minimizes blood flow between the retention sleeve and the medical device.

8. The method of claim 6, wherein the retention sleeve includes a tubular member having end sections and an intermediate section between the end sections, and wherein the method includes positioning the intermediate section adjacent to the device, and radially expanding at least a portion of the end sections into contact with the vessel.

9. The method of claim 1, wherein the method includes the step of positioning the retention device in the compressed position within a positioning sheath, and wherein the expanding step includes releasing the retention device from the positioning sheath.

10. The method of claim 9, wherein the expanding step includes causing the retention device to self-expand after being released from the positioning sheath.

11. The method of claim 1, wherein the expanding step includes positioning an expansion device within the retention device and expanding the expansion device.

12. The method of claim 11, wherein the expansion device is a balloon.

13. The method of claim 1, wherein the medical device is a pulse generator.

14. The method of claim 1, wherein the medical device is a lead.

15. The method of claim 1, further including the steps of positioning a liner within the vessel and positioning the medical device within the liner, and wherein the expanding step include expanding the retention device within the liner to engage the medical device between the retention device and the liner.

16. The method of claim 1, further including the step of promoting tissue growth into the structure of the retention device.

\* \* \* \* \*